United States Patent
Kwon et al.

(10) Patent No.: US 12,296,023 B2
(45) Date of Patent: May 13, 2025

(54) CHEMICALLY AND PHOTOCHEMICALLY INITIATED CELL MEMBRANE BLEBBING TO INDUCE CELL VESICLE PRODUCTION, MODIFICATIONS THEREOF, AND USES THEREOF

(71) Applicant: The Regents of the University of California, Oakland, CA (US)

(72) Inventors: Young Jik Kwon, Irvine, CA (US); Melissa Thone, Irvine, CA (US); Margaret Lugin, Irvine, CA (US); Dominique Antoinette Ingato, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 989 days.

(21) Appl. No.: 17/268,952

(22) PCT Filed: Aug. 16, 2019

(86) PCT No.: PCT/US2019/046968
§ 371 (c)(1),
(2) Date: Feb. 16, 2021

(87) PCT Pub. No.: WO2020/037303
PCT Pub. Date: Feb. 20, 2020

(65) Prior Publication Data
US 2021/0205469 A1    Jul. 8, 2021

Related U.S. Application Data

(60) Provisional application No. 62/735,830, filed on Sep. 24, 2018, provisional application No. 62/765,064, filed on Aug. 16, 2018, provisional application No. 62/765,102, filed on Aug. 16, 2018, provisional application No. 62/765,063, filed on Aug. 16, 2018, provisional application No. 62/765,034, filed on Aug. 16, 2018.

(51) Int. Cl.
| | |
|---|---|
| A61K 47/69 | (2017.01) |
| A61K 35/13 | (2015.01) |
| A61K 35/17 | (2015.01) |
| A61K 35/28 | (2015.01) |
| A61K 39/00 | (2006.01) |
| A61K 39/39 | (2006.01) |
| A61K 40/19 | (2025.01) |
| A61K 40/24 | (2025.01) |
| A61K 40/42 | (2025.01) |
| A61K 45/06 | (2006.01) |
| A61P 35/00 | (2006.01) |
| C12N 5/0775 | (2010.01) |
| C12N 5/0783 | (2010.01) |
| C12N 5/09 | (2010.01) |
| C12N 13/00 | (2006.01) |
| C12N 15/86 | (2006.01) |

(52) U.S. Cl.
CPC .......... *A61K 47/6917* (2017.08); *A61K 35/13* (2013.01); *A61K 35/17* (2013.01); *A61K 35/28* (2013.01); *A61K 39/39* (2013.01); *A61K 39/4622* (2023.05); *A61K 40/19* (2025.01); *A61K 40/24* (2025.01); *A61K 40/42* (2025.01); *A61K 45/06* (2013.01); *A61P 35/00* (2018.01); *C12N 5/0636* (2013.01); *C12N 5/0663* (2013.01); *C12N 5/0693* (2013.01); *C12N 13/00* (2013.01); *C12N 15/86* (2013.01); *A61K 2039/55588* (2013.01); *A61K 2239/31* (2023.05); *C12N 2501/999* (2013.01); *C12N 2740/10051* (2013.01); *C12N 2750/14143* (2013.01)

(58) Field of Classification Search
CPC .... A61K 47/6917; A61K 35/13; A61K 35/17; A61K 35/28; A61K 39/39; A61K 39/4615; A61K 39/4622; A61K 39/4644; A61K 45/06; A61K 2239/31; A61K 2039/55588; A61P 35/00; C12N 5/0636; C12N 5/0663; C12N 5/0693; C12N 13/00; C12N 15/86; C12N 2501/999; C12N 2740/10051; C12N 2750/14143
See application file for complete search history.

(56) References Cited

U.S. PATENT DOCUMENTS

| | | |
|---|---|---|
| 9,260,696 B2 | 2/2016 | Kaufman et al. |
| 2004/0022773 A1 | 2/2004 | Klingemann |
| 2007/0274953 A1 | 11/2007 | Berg et al. |

(Continued)

FOREIGN PATENT DOCUMENTS

| | | |
|---|---|---|
| CN | 108315305 A | 7/2018 |
| WO | 1997003703 A1 | 2/1997 |

(Continued)

OTHER PUBLICATIONS

Dudek et al., Immature, Semi-Mature, and Fully Mature Dendritic Cells: Toward a DC-Cancer Cells Interface that Augments Anticancer Immunity. Frontiers in Immunology 4(438):1-14 (Dec. 11, 2013).

(Continued)

*Primary Examiner* — Robert S Cabral
(74) *Attorney, Agent, or Firm* — Gavrilovich, Dodd & Lindsey LLP

(57) ABSTRACT

The disclosure provides methods to chemically and photochemically initiate cell membrane blebbing to induce cell vesicle production, modifications thereof, and uses thereof, including for drug delivery, gene therapy, cell-free cell therapy, and molecular therapy.

26 Claims, 34 Drawing Sheets

(56) References Cited

U.S. PATENT DOCUMENTS

| | | |
|---|---|---|
| 2009/0068141 A1 | 3/2009 | Parkhurst et al. |
| 2010/0143385 A1 | 6/2010 | Cook et al. |
| 2012/0177574 A1 | 7/2012 | Gho et al. |
| 2017/0112773 A1 | 4/2017 | Stachowiak et al. |

FOREIGN PATENT DOCUMENTS

| | | |
|---|---|---|
| WO | 2006087637 A2 | 8/2006 |
| WO | 2013158203 A1 | 10/2013 |
| WO | 2014138887 A1 | 9/2014 |
| WO | 2016133254 A1 | 8/2016 |
| WO | 2016193422 A1 | 12/2016 |
| WO | 2017161010 A1 | 9/2017 |
| WO | 2018102608 A1 | 6/2018 |
| WO | 2019128952 A1 | 7/2019 |
| WO | 2020180744 A1 | 2/2020 |
| WO | 20200373303 A1 | 9/2020 |

OTHER PUBLICATIONS

Mathews et al., Photochemical Internalization of Bleomycin for Glioma Treatment. Journal of Biomedical Optics 17(5):058001-1-9 (May 2012).

Park et al., Useful Tools for Biomolecule Isolation, Detection, and Identification: Acylhydrazone-Based Cleavable Linkers. Chemistry and Biology 16(7):763-772 (Jul. 31, 2009).

Scott et al., Plasma Membrane Vesiculation in 3T3 and SV3T3 Cells. Journal of Cell Science 35:229-243 (1979).

Thomas, Shane. Search History or PCTUS19/46968. Oct. 11, 2019.

Zeng et al., High Efficiency labeling of glycoproteins on living cells. Nature Methods 6(3):1-7 (Feb. 22, 2009).

Gyorgy et al., "Membrane vesicles, current state-of-the-art: emerging role of extracellular vesicles." Cell. Mol. Life Sci. 68:2667-2688 (2011).

Hagmann et al., "Regulation of Plasma Membrane Blebbing by the Cytoskeleton." Journal of Cellular Biochemistry 73:488-499 (1999).

Harrigan et al., "Accumulation of doxorubicin and other lipophilic amines into large unilamellar vesicles in response to transmembrane pH gradients" Biochimica et Biophysica Acta 1149 :329-338 (1993).

Hedlund et al., "Thermal- and Oxidative Stress Causes Enhanced Release of NKG2D Ligand-Bearing Immunosuppressive Exosomes in Leukemia/Lymphoma T and B Cells." PLoS One 6(2):e16899 (2011).

Hillaireau et al., "Nanocarriers' entry into the cell: relevance to drug delivery." Cell. Mol. Life Sci. 66:2873-2896 (2009).

Hinshaw et al., "Cytoskeletal and Morphologic Impact of Cellular Oxidant Injury." Am J Pathol 123(3):454-464 (1986).

Immordino et al., "Stealth liposomes: review of the basic science, rationale, and clinical applications, existing and potential." International Journal of Nanomedicine, 1(3) 297-315 (2006).

Ingato et al., "Cancer Cell-Derived, Drug-Loaded Nanovesicles Induced by Sulfhydryl-Blocking for Effective and Safe Cancer Therapy." ACS Nano 12:9568-9577 (2018).

Ishida et al., "PEGylated liposomes elicit an anti-PEG IgM response in a T cell-independent manner." Journal of Controlled Release 122:349-355 (2007).

Iyer et al., "Exploiting the enhanced permeability and retention effect for tumor targeting." Drug Discovery Today 11 (17/18):812-818 (2006).

Katsuda et al., "The therapeutic potential of mesenchymal stem cell-derived extracellular vesicles." Proteomics 13:1637-1653 (2013).

Keller et al., "Differences in Cortical Actin Structure and Dynamics Document That Different Types of Blebs Are Formed by Distinct Mechanisms." Experimental Cell Research 277:161-172 (2002).

Kesharwani et al., "A review of nanocarriers for the delivery of small interfering RNA." Biomaterials 33:7138-7150 (2012).

Kesimer et al., "Physical Characterization and profiling of airway epithelial derived exosomes using light scattering," Methods, 87:59-63 (2015).

Kim et al., "Exosomes Derived from IL-10-Treated Dendritic Cells Can Suppress Inflammation and Collagen-Induced Arthritis." J Immunol 174(10):6440-6448 (2005).

King et al., "Hypoxic enhancement of exosome release by breast cancer cells." BMC Cancer 12:421 (2012).

Kramer-Albers et al., "Oligodendrocytes secrete exosomes containing major myelin and stress-protective proteins: Trophic support for axons?" Proteomics Clin. Appl. 1:1446-1461 (2007).

Labeur et al., "Generation of Tumor Immunity by Bone Marrow-Derived Dendritic Cells Correlates with Dendritic Cell Maturation Stage." The Journal of Immunology, 162 (1) 168-175 (Jan. 1, 1999).

Lamichhane et al., "Emerging Roles for Extracellular Vesicles in Tissue Engineering and Regenerative Medicine." Tissue Engineering: Part B 21(1):45-54 (2015).

Landau et al., "The Effects of High Hydrostatic Pressure on Human Cells in Primary and Continuous Culture." Experimental Cell Research 23:538-548 (1961).

Lee et al., "Exosomes and microvesicles: extracellular vesicles for genetic information transfer and gene therapy." Human Molecular Genetics 21(1)R125-R134 (2012).

Lian et al., "Trends and Developments in Liposome Drug Delivery Systems." Journal of Pharmaceutical Sciences 90 (6):667-680 (2001).

Liu et al., "Murine Mammary Carcinoma Exosomes Promote Tumor Growth by Suppression of NK Cell Function." The Journal of Immunology 176(3):1375-85 (2006).

Llopis et al., "Measurement of cytosolic, mitochondrial, and Golgi pH in single living cells with green fluorescent proteins." Proc. Natl. Acad. Sci. USA vol. 95:6803-6808 (1998).

Lv et al., "Toxicity of cationic lipids and cationic polymers in gene delivery." Journal of Controlled Release 114:100-109 (2006).

Lyass et al., "Correlation of Toxicity with Pharmacokinetics of Pegylated Liposomal Doxorubicin (Doxil) in Metastatic Breast Carcinoma." Cancer 89(5):1037-1047 (2000).

Mace et al., "NK Cell Lytic Granules Are Highly Motile at the Immunological Synapse and Require F-Actin for Post-Degranulation Persistence." J Immunol 189(10):4870-4880 (2012).

Mackenzie et al., "Rapid Secretion of Interleukin-1B by Microvesicle Shedding." Immunity 8:325-835 (2001).

Maki et al., "Factors Regulating the Cytotoxic Activity of the Human Natural Killer Cell Line, NK-92." Journal of Hematotherapy & Stem Cell Research 10:369-383 (2001).

Martinez et al., "Transfer of differentiation signal by membrane microvesicles harboring hedgehog morphogens." Blood 108(9):3012-3020 (2006).

Mathivanan et al., "Exosomes: Extracellular organelles important in intercellular communication." Journal of Proteomics 73:1907-1920 (2010).

Mayer et al., "Uptake of adriamycin into large unilamellar vesicles in response to a pH gradient." Biochimica et Biophysica Acta 857:123-126 (1986).

Medvedev et al., "Regulation of Fas and Fas-Ligand Expression in NK Cells by Cytokines and the Involvement of Fas-Ligand in NK/LAK Cell-Mediated Cytotioxicity." Cytokine 9(6):394-404 (1997).

Miller, J.S., "Therapeutic applications: natural killer cells in the clinic." Hematology Am Soc Hematol Educ Program. 247-53 (2013).

Mitran et al., "Multiscale Computation of Cytoskeletal Mechanics During Blebbing." Cellular and Biomolecular Mechanics and Mechanobiology pp. 345-371 (2010).

Miyoshi et al., "Calpain Activation in Plasma Membrane Bleb Formation During tert-Butyl Hydroperoxide-Induced Rat Hepatocyte Injury." Gastroenterology 110:1897-19 (1996).

Momen-Heravi et al., "Current methods for the isolation of extracellular vesicles." Biological Chemistry 394(10) 1253-1262 (2013).

Monleon et al., "Differential Secretion of Fas Ligand- or APO2 Ligand/TNF-Related Apoptosis-Inducing Ligand-Carrying Microvesicles During Activation-Induced Death of Human T Cells." The Journal of Immunology 67(12):6736-44 (2001).

Muralidharan-Chari et al., "Microvesicles: mediators of extracellular communication during cancer progression." Journal of Cell Science 123:1603-1611 (2010).

Niu et al., "Preparation and Characterization of Doxorubicin Liposomes." Methods in Molecular Biology 624:211-219 (2010).

(56) References Cited

OTHER PUBLICATIONS

Norman et al., "Cell Blebbing and Membrane Area Homeostasis in Spreading and Retracting Cells." Biophysical Journal 99:1726-1733 (2010).
Obregon et al., "Exovesicles from Human Activated Dendritic Cells Fuse with Resting Dendritic Cells, Allowing Them to Present Alloantigens." The American Journal of Pathology 169(6):2127-2136 (2006).
Ohno et al., "Systemically Injected Exosomes Targeted to EGFR Deliver Antitumor MicroRNA to Breast Cancer Cells." Molecular Therapy 21(1):185-191 (2013).
Parolini et al., "Microenvironmental pH Is a Key Factor for Exosome Traffic in Tumor Cells" Journal of Biological Chemistry 284(49):34211-34222 (2009).
Pascucci et al., "Paclitaxel is incorporated by mesenchymal stromal cells and released in exosomes that inhibit in vitro tumor growth: A new approach for drug delivery." Journal of Controlled Release 192:262-270 (2014).
Peche et al., "Induction of Tolerance by Exosomes and Short-Term Immunosuppression in a Fully MHC-Mismatched Rat Cardiac Allograft Model." American Journal of Transplantation 6:1541-1550 (2006).
Petros et al., "Strategies in the design of nanoparticles for therapeutic applications." Nature Reviews Drug Discovery 9:615-627 (2010).
Pornpattananangkul et al., "Stimuli-Responsive Liposome Fusion Mediated by Gold Nanoparticles." ACS Nano. 4(4):1935-1942 (2010).
Portney et al., "Nano-oncology: drug delivery, imaging, and sensing." Anal Bioanal Chem 384:620-630 (2006).
Rafelski et al., "Crawling Toward a Unified Model of Cell Motility: Spatial and Temporal Regulation of Actin Dynamics." Annu. Rev. Biochem. 73:209-39 (2004).
Armandola, Emma, Search Report, Application No. 19850465.6, European Patent Office, May 11, 2022.
Ingato et al., "Cancer Cell-Derived, Drug-Loaded Nanovesicles Induced by Sulfhydryl-Blocking for Effective and Safe Cancer Therapy", ACS Nano, Aug. 21, 2018, vol. 12, No. 9, pp. 9568-9577.
Lu et al., "Recent advances on extracellular vesicles in therapeutic delivery: Challenges, solutions, and opportunities", European Journal of Pharmaceutics and Biopharmaceutics, Jul. 21, 2017, vol. 119, pp. 381-395.
Tian et al., "Surface functionalized exosomes as targeted drug delivery vehicles for cerebral ischemia therapy", Biomaterials, Oct. 4, 2017, vol. 150, pp. 137-149.
Baharlou, Simin, International Preliminary Report on Patentability and Written Opinion for PCT/US19/46968, The International Bureau of WIPO, Feb. 25, 2021.
Enderle et al., "Characterization of RNA from Exosomes and Other Extracellular Vesicles Isolated by a Novel Spin Column-Based Method." Plos One 10(8): e0136133.
Evans et al., "Physical Properties of Surfactant Bilayer Membranes: Thermal Transitions, Elasticity, Rigidity, Cohesion, and Colloidal Interactions." Journal Physical Chemistry 91:4219-4228 (1987).
Fang et al., "Tumor-derived exosomal miR-1247-3p induces cancer-associated fibroblast activation to foster lung metastasis of liver cancer." Nature Communications 9(191):1-13 (2018).
Fishkind et al., "Microinjection of the Catalytic Fragment of Myosin Light Chain Kinase into Dividing Cells: Effects on Mitosis and Cytokinesis." The Journal of Cell Biology 114(5):967-975 (1991).
Friedl et al., "Tumour-Cell Invasion and Migration: Diversity and Escape Mechanisms." Nature Reviews 3:362-374 (2003).
Fuhrmann et al., "Active loading into extracellular vesicles significantly improves the cellular uptake and photodynamic effect of porphyrins." Journal of Controlled Release 205:35-44 (2015).
Gangoda et al., "Cortactin enhances exosome secretion without altering cargo." The Journal of Cell Biology 214 (2):129-131.
Garay et al., "Antibodies against polyethylene glycol in healthy subjects and in patients treated with PEG-conjugated agents." Expert Opinion Drug Development 9(11):1319-23 (2012).
Gardiner et al., "Extracellular vesicle sizing and enumeration by nanoparticle tracking analysis." Journal of Extracellular Vesicles 2:(1):19671 (2013).
Gilleron et al., "Image-based analysis of lipid nanoparticle-mediated siRNA delivery, intracellular trafficking and endosomal escape." Nature Biotechnology 31:638-646 (2013).
Goodwin et al., "Single-Dose Toxicity Study of Hepatic Intra-arterial Infusion of Doxorubicin Coupled to a Novel Magnetically Targeted Drug Carrier." Toxicological Sciences 60:177-183 (2001).
Herberts et al., "Risk factors in the development of stem cell therapy." Journal of Translational Medicine 9(29):1-14 (2011).
Hogue, MJ. "The Effect of Hypotonic and Hypertonic Solutions on Fibroblasts of the Embryonic Chick Heart in vitro." Journal of Experimental Medicine 30(6):617-648 (1919).
Hood et al., "Maximizing Exosome Colloidal Stability Following Electroporation." Analytical Biochemistry 448:41-49 (2014).
Hoshino et al., "Tumour exosome integrins determine organotropic metastasis." Nature 527(7578): 329-335 (2015).
Hsu et al., "Regulation of exosome secretion by Rab35 and its GTPase-activating proteins TBC1D10A-C." Journal of Cell Biology 189(2):223-232 (2010).
Hung et al. "Stabilization of Exosome-targeting Peptides via Engineered Glycosylation." The Journal of Biology Chemistry 290(13):8166-8172 (2015).
Hung et al., "A platform for actively loading cargo RNA to elucidate limiting steps in EV-mediated delivery." Journal of Extracellular Vescicles 5:31027 (2016).
Ibrahim et al., "Exosomes as Critical Agents of Cardiac Regeneration Triggered by Cell Therapy." Stem Cell Reports 2:606-619 (2014).
Im et al., "Label-free detection and molecular profiling of exosomes with a nano-plasmonic sensor." Nat Biotechnol. 32(5):490-495 (2014).
Ingato et al., "Good things come in small packages: Overcoming challenges to harness extracellular vesicles for therapeutic delivery." Journal Controlled Release 241:174-185 (2016).
Ishida et al. "Accelerated blood clearance of PEGylated liposomes upon repeated injections: Effect of doxorubicin-encapsulation and high-dose first injection." Journal of Controlled Release 115:251-258 (2006).
Israelachivilli et al., "Theory of Self-Assembly of Hydrocarbon Amphiphiles into Micelles and Bilayers." J. Chem. Soc., Faraday Trans. 2 72:525-1568 (1976).
Jang et al., "Bioinspired Exosome-Mimetic Nanovesicles for Targeted Delivery of Chemotherapeutics to Malignant Tumors." ACS Nano 7(9):7698-7710 (2013).
Jeyaram et al., "Preservation and Storage Stability of Extracellular Vesicles for Therapeutic Applications." AAPS J 20(1):1-13 (2017).
Jimenez et al., "Endothelial cells release phenotypically and quantitatively distinct microparticles in activation and apoptosis." Thrombosis Research 109:175-180 (2003).
Jo et al., "Microfluidic fabrication of cell-derived nanovesicles as endogenous RNA carriers." Lab Chip 14(7):1261-9 (2014).
Johnstone et al., "Vesicle Formation during Reticulocyte Maturation." The Journal of Biological Chemistry 262(19):9412-9420 (1987).
Kadiu et al., "Biochemical and Biologic Characterization of Exosomes and Microvesicles as Facilitators of HIV-1 Infection in Macrophages." The Journal of Immunology 189(2):744-54 (2012).
Kanwar et al., "Microfluidic device (ExoChip) for On-Chip isolation, quantification and characterization of circulating exosomes." Lab Chip 14(11):1891-900 (2014).
Kastelowitz et al., "Exosomes and Microvesicles: Identification and Targeting By Particle Size and Lipid Chemical Probes." Chembiochem 15(7): 923-928 (2014).
Katakowski et al., "Exosomes from marrow stromal cells expressing miR-146b inhibit glioma growth." Cancer Lett. 335(1):201-204 (2013).
Kessler et al., "Interference by Lipids in the Determination of Protein Using Bicinchoninic Acid." Analytical Biochemistry 159:138-142 (1986).
Kim et al., "Large-scale generation of cell-derived nanovesicles." 6(20):12056-64 (2014).

(56) References Cited

OTHER PUBLICATIONS

King et al., "Bioreactor Development for Stem Cell Expansion and Controlled Differentiation." Curr Opin Chem Biol. 11(4): 394-398 (2007).

Kooijmans et al., "Display of GPI-anchored anti-EGFR nanobodies on extracellular vesicles promotes tumour cell targeting." Journal of Extracellular Vesicles 5:31053 (2016).

Kosaka et al., "Secretory Mechanisms and Intercellular Transfer of MicroRNAs in Living Cells" The Journal of Biological Chemistry 285(23):17442-17452 (2010).

Lai et al., "Exosome secreted by MSC reduces myocardial ischemia/reperfusion injury." Stem Cell Research 4:214-222 (2010).

Lai et al., "Dynamic Biodistribution of Extracellular Vesicles In Vivo Using a Multimodal Imaging Reporter." Stem Cell Research 4:214-222 (2010).

Lammmers et al., "Drug targeting to tumors: Principles, pitfalls and (pre-) clinical progress." Journal of Controlled Release 161:175-187 (2012).

Lamparski et al., "Production and characterization of clinical grade exosomes derived from dendritic cells." Journal of Immunological Methods 270:211-226 (2002).

Lauf et al., "A Chloride Dependent K+ Flux Induced by N-ethylmaleimide in Genetically Low K+ Sheep and Goat Erythrocytes." Biochemical and Biophysical Research Communications 92(4):1422-1428 (1980).

Lee et al., "Acoustic Purification of Extracellular Microvesicles." ACS Nano 9(3): 2321-2327 (2015).

Lener et al., "Applying extracellular vesicles based therapeutics in clinical trials—an ISEV position paper." Journal of Extracellular Vesicles 4:30087 (2015).

Li et al., "Exosomes Derived from Hypoxic Oral Squamous Cell Carcinoma Cells Deliver miR-21 to Normoxic Cells to Elicit a Prometastatic Phenotype." Cancer Res 76(7):1770-1780 (2016).

Liu et al., "Targeted exosome-mediated delivery of opioid receptor Mu siRNA for the treatment of morphine relapse." Scientific Reports 5:17543 (2015).

Llorente et al., "Molecular lipidomics of exosomes released by PC-3 prostate cancer cells." Biochimica et Biophysica Acta 1831:1302-1309 (2013).

Mahaweni et al., "Tumour-derived exosomes as antigen delivery carriers in dendritic cell-based immunotherapy for malignant mesothelioma." Journal of Extracellular Vesicles 2:22492 (2013).

Mause et al., "Protagonists of a Novel Communication Network for Intercellular Information Exchange." Microparticles 107(9):1047-57 (2010).

Mills et al., "Apoptotic Membrane Blebbing Is Regulated by Myosin Light Chain Phosphorylation." The Journal of Cell Biology 140(3):627-636 (1998).

Momen-Heravi et al., "Current methods for the isolation of extracellular vesicles." Biol Chem 394(10):1253-1262 (2013).

Momen-Heravi et al., "Exosome-mediated delivery of functionally active miRNA-155 inhibitor to macrophages." Nanomedicine 10(7):1517-1527 (2014).

Momparler et al., "Effect of Adriamycin on DNA, RNA and Protein Synthesis in Cell-free Systems and Intact Cells." Cancer Research 36:2891-2895 (1976).

Montecalvo et al., "Mechanism of transfer of functional microRNAs between mouse dendritic cells via exosomes." Blood 119(3):756-766.

Munagala et al., "Bovine milk-derived exosomes for drug delivery." Cancer Lett. 371(1): 48-61 (2016).

Nakamishi et al., "Bioactive Nanocarbon Assemblies: Nanoarchitectonics and Applications." Nanotechnology 9(3):378-394 (2014).

Nasongkla et al., "cRGD-Functionalized Polymer Micelles for Targeted Doxorubicin Delivery." Angew. Chem. Int. Ed. 43:6323-6327 (2004).

Nikam et al., "Nanoparticles—An Overview." International Journal of Research and Development in Pharmacy and Life Sciences 3(5): 1121-1127 (2014).

O'Brien et al., "miR-134 in extracellular vesicles reduces triple-negative breast cancer aggression and increases drug sensitivity." Oncotarget, 6(32):32774-32788 (2015).

Ohara et al., "Effective delivery of chemotherapeutic nanoparticles by depleting host Kupffer cells." Int. J. Cancer: 131:2402-2410 (2012).

Akao et al., "Microvesicle-mediated RNA Molecule Delivery System Using Monocytes/Macrophages." Molecular Therapy. 19(2):395-399 (2011).

Akers et al., "Biogenesis of extracellular vesicles (EV): exosomes, microvesicles, retrovirus-like vesicles, and apoptotic bodies." J Neurooncol 113:1-11 (2013).

Albanese et al., "Biologically Active Fas Antigen and Its Cognate Ligand Are Expressed on Plasma Membrane-Derived Extracellular Vesicles." Blood. 91(10):3862-3874 (May 15, 1998).

Allen et al., "Drug Delivery Systems: Entering the Mainstream." Science 303:1818 (2004).

Alvarez-Erviti et al., "Delivery of siRNA to the mouse brain by systemic injection of targeted exosomes." Nature Biotechnology 29(4):341-347 (2011).

Armeanu et al., "Natural Killer Cell-Mediated Lysis of Hepatoma Cells via Specific Induction of NKG2D Ligands by the Histone Deacetylase Inhibitor Sodium Valproate." Cancer Res 65(14):6321-6329 (2005).

Bailey et al., "The Role of Sulphydryl Groups in the Interaction of Myosin and Actin." Biochimica Et Biophysica Acta 1:506-516 (1947).

Baj-Kryworzeka et al., "Tumour-derived microvesicles carry several surface determinants and mRNA of tumour cells and transfer some of these determinants to monocytes." Cancer Immunol Immunother 55:808-818 (2006).

Bangham et al., "Negative Staining of Phospholipids and their Structural Modification by Surface-active Agents as observed in the Electron Microscope." J. Mol. Biol. 8:660-668 (1964).

Barry et al., "Determining the Effects of Lipophilic Drugs on Membrane Structure by Solid-State NMR Spectroscopy: The Case of the Antioxidant Curcumin." J. Am. Chem. Soc. 131:4490-4498 (2009).

Boron et al., "Intracellular pH Transients in Squid Giant Axons Caused by $CO_2$, $NH_3$, and Metabolic Inhibitors." The Journal of General Physiology 67:91-112 (1976).

Bosma et al., "The SCID Mouse Mutant: Definition, Characterization, and Potential Uses." Ann. Rev. Immunol. 9:323-50 (1991).

Braicu et al., "Exosomes as divine messengers: are they the Hermes of modern molecular oncology?" Cell Death and Differentiation 22:34-45 (2015).

Braunsmann et al., "High-speed force mapping on living cells with a small cantilever atomic force microscope." Review of Scientific Instruments 85:073703 (2014).

Brown et al., "Gene delivery with synthetic (non viral) carriers." International Journal of Pharmaceutics 229:1-21 (2001).

Bruno et al., "Microvesicles Derived from Mesenchymal Stem Cells Enhance Survival in a Lethal Model of Acute Kidney Injury." PLoS One 7(3):e33115 (2012).

Caby et al., "Exosomal-like vesicles are present in human blood plasma." International Immunology. 17(7):879-887 (2005).

Cai et al., "Activated T Cell Exosomes Promote Tumor Invasion via Fas Signaling Pathway." J Immunol 188(12):5954-5961 (2012).

Camussi et al., "Exosome/microvesicle-mediated epigenetic reprogramming of cells." Am J Cancer Res 1(1):98-110 (2011).

Cantaluppi et al., "Microvesicles derived from endothelial progenitor cells protect the kidney from ischemia-reperfusion injury by microRNA-dependent reprogramming of resident renal cells." Kidney International 82:412-427 (2012).

Chaput et al., "Exosome-based immunotherapy." Cancer Immunol Immunother 53:234-239 (2004).

Chaput et al., "Exosomes: immune properties and potential clinical implementations." Semin Immunopathol 33:419-440 (2011).

Charras et al., "Non-equilibration of hydrostatic pressure in blebbing cells." Nature Letters 435:365-369 (2005).

Charras et al., "Reassembly of contractile actin cortex in cell blebs." The Journal of Cell Biology, 175,(3): 477-490. (2006).

(56) References Cited

OTHER PUBLICATIONS

Charras et al., "Blebs lead the way: how to migrate without lamellipodia." Nature Reviews 9:730-736 (2008).
Chen et al., "Microfluidic isolation and transcriptome analysis of serum microvesicles." Lab Chip 10:505-511 (2010).
Cocucci et al., "Shedding microvesicles: artefacts no more." Trends in Cell Biology 19(2):43-51 (2009).
Cullis et al., "Generating and loading of liposomal systems for drug-delivery applications." Advanced Drug Delivery Reviews 3:67-282 (1989).
Dalle-Donne et al., "The Actin Cytoskeleton Response to Oxidants: From Small Heat Shock Protein Phosphorylation to Changes in the Redox State of Actin Itself." Free Radical Biology & Medicine, 31(12):1624-1632, (2001).
De Jong et al., "Cellular stress conditions are reflected in the protein and RNA content of endothelial cell-derived exosomes." J Extracell Vesicles 1 (Apr. 16, 2012).
Distler et al., "Microparticles as Regulators of Inflammation." Arthritis & Rheumatism 52(11):3337-3348 (2005).
Dolo et al., "Enrichment and localization of ganglioside GD3 and caveolin-1 in shed tumor cell membrane vesicles." Biochimica et Biophysica Acta 1486:265-274 (2000).
Edwards et al., "Spontaneous Vesicle Formation at Lipid Bilayer Membranes." Biophysical Journal 71:1208-1214 (1996).
El Andaloussi et al.,"Extracellular vesicles: biology and emerging therapeutic opportunities." Nature Reviews 12:347-357 (2013).
El Aneed, Anas. "An overview of current delivery systems in cancer gene therapy." Journal of Controlled Release 94 1-14 (2004).
Elmore, Susan. "Apoptosis: A Review of Programmed Cell Death." Toxicol Pathol. 35(4):495-516 (2007).
Erickson, Harold P. "Size and Shape of Protein Molecules at the Nanometer Level Determined by Sedimentation, Gel Filtration, and Electron Microscopy." Biological Procedures Online 11(1):32-51 (2009).
Fackler et al., "Cell motility through plasma membrane blebbing." J. Cell Biol. 181(6):879-884 (2008).
Fang et al., "The EPR effect: Unique features of tumor blood vessels for drug delivery, factors involved, and limitations and augmentation of the effect." Advanced Drug Delivery Reviews 63:136-151 (2011).
Faure et al., "Exosomes are released by cultured cortical neurones." J. Mol. Cell. Neurosci. 31:642-648 (2006).
Fevrier et al., "Exosomes: endosomal-derived vesicles shipping extracellular messages." Current Opinion in Cell Biology 16:415-421 (2004).
Fox et al., "Formaldehyde Fixation." The Journal of Histochemistry and Cytochemistry 33(8):845-853 (1985).
Fritze et al., "Remote loading of doxorubicin into liposomes driven by a transmembrane phosphate gradient." Biochimica et Biophysica Acta 1758:1633-1640 (2006).
Fuhrmann et al., "Cell-derived vesicles for drug therapy and diagnostics: Opportunities and challenges." Nano Today 10:397-409 (2015).
Gabizon et al., "Dose Dependency of Pharmacokinetics and Therapeutic Efficacy of Pegylated Liposomal Doxorubicin (DOXIL) in Murine Models." Journal of Drug Targeting 10 (7):539-548 (2002).
Ganta et al., "A review of stimuli-responsive nanocarriers for drug and gene delivery." Journal of Controlled Release 126:187-204 (2008).
Gatti et al., "Microvesicles derived from human adult mesenchymal stem cells protect against ischaemia—reperfusion-induced acute and chronic kidney injury." Nephrol Dial Transplant 26:1474-1483 (2011).
Gesierich et al., "Systemic Induction of the Angiogenesis Switch by the Tetraspanin D6.1A/CO-029." Cancer Res 66:(14):7083-7094 (2006).
Giacca et al., "Virus-mediated gene delivery for human gene therapy." Journal of Controlled Release 161: 377-388 (2012).
Gupta et al., "Dietary antioxidant curcumin inhibits microtubule assembly through tubulin binding." FEBS Journal 273:5320-5332 (2006).
Toledano et al., "Reconstructed Stem Cell Nanoghosts: A Natural Tumor Targeting Platform." Nano Lett. 13:3248-3255 (2013).
Tominaga et al., "A novel platform for cancer therapy using extracellular vesicles." Advanced Drug Delivery Reviews 95:50-55 (2015).
Tricarico et al., "Biology and biogenesis of shed microvesicles." Small Gtpases 8(4):220-232 (2017).
Turiak et al., "Proteomic characterization of thymocyte-derived microvesicles and apoptotic bodies in BALB/c mice." Journal of Proteomics 74:2025-2033 (2011).
Van Der Pol et al., "Optical and non-optical methods for detection and characterization of microparticles and exosomes." Journal of Thrombosis and Haemostasis 8:2596-2607 (2010).
Van Deun et al., "The impact of disparate isolation methods for extracellular vesicles on downstream RNA profiling." Journal of Extracellular Vesicles 3:24858 (2014).
Verhoef et al., "Questioning the Use of PEGylation for Drug Delivery." Drug Deliv Transl Res. 3(6):499-503 (2013).
Viaud et al., "Dendritic Cell-Derived Exosomes for Cancer Immunotherapy: What's Next?" Cancer Research 70 (4):1281-5 (2010).
Villarroya-Beltri et al., "ISGylation controls exosome secretion by promoting lysosomal degradation of MVB proteins."
Vion et al., "Shear Stress Regulates Endothelial Microparticle Release." Circulation Research 112(10):1323-1333 (2013).
Voldman, J. "Electrical Forces For Microscale Cell Manipulation." Annu. Rev. Biomed. Eng. 8:425-54 (2006).
Xu et al., "Extracellular vesicle isolation and characterization: toward clinical application." The Journal of Clinical Investigation 126(4):1152-1162 (2016).
Yamashita et al., "Effects of Exosome Isolation Methods on Physicochemical Properties of Exosomes and Clearance of Exosomes from the Blood Circulation." Eur J Pharm Biopharm 98:1-8 (2016).
Yang et al. "Current Advances of Lanthanide Ion (Ln3+)-Based Upconversion Nanomaterials for Drug Delivery." Chemical Society Reviews 44:1416-1448 (2015).
Yeatts et al., "Bioreactors to Influence Stem Cell Fate: Augmentation of Mesenchymal Stem Cell Signaling Pathways via Dynamic Culture Systems." Biochim Biophys Acta. 1830(2): 2470-2480 (2013).
Yu et al., "Exosomes Secreted from GATA-4 Overexpressing Mesenchymal Stem Cells Serve as a Reservoir of Anti-Apoptotic microRNAs for Cardioprotection." Int J Cardiol. 182: 349-360 (2015).
Yuan et al., "Macrophage Exosomes as Natural Nanocarriers for Protein Delivery to Inflamed Brain." Biomaterials. 142:1-12 (2017).
Yuana et al., "Co-isolation of extracellular vesicles and high-density lipoproteins using density gradient ultracentrifugation." Journal of Extracellular Vesicles 3:23262 (2014).
Zaborowski et al., "Extracellular Vesicles: Composition, Biological Relevance, and Methods of Study." BioScience 65(8):783-797 (2015).
Zhang et al., "Comparison of ultracentrifugation and density gradient separation methods for isolating Tca8113 human tongue cancer cell line-derived exosomes." Oncology Letters 8: 1701-1706 (2014).
Zhang et al., "Exosome and Exosomal MicroRNA: Trafficking, Sorting, and Function." Genomics Proteomics Bioinformatics 13:17-24 (2015).
Zhang et al., "Focus on Extracellular Vesicles: Therapeutic Potential of Stem Cell-Derived Extracellular Vesicles." Int. J. Mol. Sci. 17(174):1-11 (2016).
Zhao et al., "A Simple Way to Enhance Doxil® Therapy: Drug Release from Liposomes at the Tumor Site by Amphiphilic Block Copolymer." J Control Release 168(1):61-69 (2013).
Zhao et al., "Fixation-induced cell blebbing on spread cells inversely correlates with phosphatidylinositol 4,5-bisphosphate level in the plasma membrane." FEBS Open Bio 4:190-199 (2014).

(56) References Cited

OTHER PUBLICATIONS

Zollinger et al., "Cytologic Studies with the Phase Microscope I. The Formation of "Blisters" on Cells in Suspension (Potocytosis), With Observations on the Nature of the Cellular Membrane." Am J Pathol. 24(3):545-567 (1948).
Ratajczak et al., "Embryonic stem cell-derived microvesicles reprogram hematopoietic progenitors: evidence for horizontal transfer of mRNA and protein delivery." Leukemia 20:847-856 (2006).
Reagan et al., "Mesenchymal Stem Cell Tumor-Homing: Detection Methods in Disease Model Systems." Stem Cells. 29(6):920-927 (2011).
Ridley, A.J. "Life at the Leading Edge." Cell 145:1012-1022 (2011).
Riteau et al., "Exosomes Bearing HLA-G are Released by Melanoma Cells." Human Immunology 64:1064-1072 (2003).
Savina et al., "Exosome Release Is Regulated by a Calcium-dependent Mechanism in K562 Cells." The Journal of Biological Chemistry 278(22):20083-20090 (2003).
Scott, R.E., "Plasma Membrane Vesiculation: A New Technique for Isolation of Plasma Membranes." Science 194 (4266):743-5 (1976).
Scott et al., "Undifferentiated and differentiated L6 myoblast plasma membranes. I: Comparison of the morphology of plasma membrane vesiculation and the factors influencing the vesiculation process," Cell Differentiation, 7(6):325-334 (1978).
Sezgin et al., "Elucidating membrane structure and protein behavior using giant plasma membrane vesicles." Nature Protocols, 7(6): 1042-1051 (2012).
Silva et al., "Cell-derived vesicles as a bioplatform for the encapsulation of theranostic nanomaterials." Nanoscale, 5:11374-11384 (2013).
Simon et al., "Intracellular pH and the control of multidrug resistance." Proc. Natl. Acad. Sci. USA 91:1128-1132 (1994).
Simpson et al., "Extracellular Microvesicles: The need for Internationally Recognized Nomenclature and Stringent Purification Criteria." J. Proteomics Bioinform 5:2 (2012).
Skog et al., "Glioblastoma microvesicles transport RNA and protein that promote tumor growth and provide diagnostic biomarkers." Nat Cell Biol. 10(12):1470-1476 (2008).
Skokos et al., "Mast Cell-Derived Exosomes Induce Phenotypic and Functional Maturation of Dendritic Cells and Elicit Specific Immune Responses In Vivo." The Journal of Immunology 170(6):3037-3045 (2003).
Smith et al., "Extracellular Vesicles Commercial Potential as Byproducts of Cell Manufacturing for Research and Therapeutic Use." BioProcess International 13:1-13 (2015).
Smith et al., "In Vitro T-Cell Generation From Adult, Embryonic, and Induced Pluripotent Stem Cells: Many Roads to One Destination." Stem Cells 33:3174-3180 (2015).
Smyth et al., "Biodistribution and delivery efficiency of unmodified tumor-derived exosomes." Journal of Controlled Release 199:145-155 (2015).
Steinherz et al., "Antileukemia Activity of a Natural Killer Cell Line against Human Leukemias." Clinical Cancer Research. 4:2859-2868 (1998).
Stoorvogel et al., "The Biogenesis and Functions of Exosomes." Traffic 3:321-330 (2002).
Sun et al., "A Novel Nanoparticle Drug Delivery System: The Anti-inflammatory Activity of Curcumin Is Enhanced When Encapsulated in Exosomes." Molecular Therapy 18(9):1606-1614 (2010).
Szajnik et al., "Tumor-Derived Microvesicles Induce, Expand and Up-Regulate Biological Activities of Human Regulatory T Cells (Treg)" PLoS One 5(7):e11469 (2010).
Tan et al., "Cell or Cell Membrane-Based Drug Delivery Systems." Theranostics 5(8)863-881 (2015).
Taverna et al., "Exosomal shuttling of miR-126 in endothelial cells modulates adhesive and migratory abilities of chronic myelogenous leukemia cells." Molecular Cancer 13:169 (2014).
Taylor et al., "Apoptosis: controlled demolition at the cellular level." Molecular Cell Biology 9:231-241 (2008).
Thery et al., "Exosomes: Composition, Biogenesis and Function." Immunology 2:569-579 (2002).
Thery, C. "Isolation and Characterization of Exosomes from Cell Culture Supernatants and Biological Fluids." Curr Protoc Cell Biol. Chapter 3:Unit 3.22 (2006).
Thery et al., "Membrane vesicles as conveyors of immune responses." Immunology 9:581-593 (2009).
Thomas et al., "Progress and problems with the use of viral vectors for gene therapy." Nature Reviews Genetics, 4:346-358 (2003).
Thomas, S. International Search Report and Written Opinion for PCT/US17/64062. (Feb. 23, 2018).
Thureson-Klein et al., "Morphological effects of osmolarity on purified noradrenergic vesicles." Journal of Neurocytology 4(5):609-627 (1975).
Tian et al., "A doxorubicin delivery platform using engineered natural membrane vesicle exosomes for targeted tumor therapy." Biomaterials 35:2383e2390 (2014).
Tinevez et al., "Role of cortical tension in bleb growth." Proceedings in the National Academy of Sciences 106(44):18581-18586 (2009).
Torgerson et al., "The actin-myosin cytoskeleton mediates reversible agonist-induced membrane blebbing." Journal of Cell Science 111:2911-2922 (1998).
Valadi et al., "Exosome-mediated transfer of mRNAs and microRNAs is a novel mechanism of genetic exchange between cells." Nature Cell Biology 9(6) (2007).
Van Den Boorn et al., "SiRNA delivery with exosome nanoparticles." Nature Biotechnology 29(4):325-326 (2011).
Van_Dommelen et al., "Microvesicles and exosomes: Opportunities for cell-derived membrane vesicles in drug delivery." Journal of Controlled Release 161:635-644 (2012).
Vivier et al., "Functions of Natural Killer Cells." Nature Immunology 9(5):503-510 (2008).
Vlassov et al., "Exosomes: Current knowledge of their composition, biological functions, and diagnostic and therapeutic potentials." Biochimica et Biophysica Acta 1820:940-948 (2012).
Wahlgren et al., "Plasma exosomes can deliver exogenous short interfering RNA to monocytes and lymphocytes." Nucleic Acids Research. 40(17):e130 (2012).
Warren et al., "NK cells and apoptosis." Immunology and Cell Biology 77:64-75 (1999).
Weiss, Marie-France. Supplementary European Search Report for EP17875424. Jun. 24, 2020.
Wennerberg et al., "Doxorubicin sensitizes human tumor cells to NK cell- and T-cell-mediated killing by augmented TRAIL receptor signaling." Int. J. Cancer. 133:1643-1653 (2013).
Whitford et al., "Continuous Production of Exosomes Utilizing the Technical Advantages of Hollow-Fiber Bioreactor Technology." Genetic Engineering & Biotechnology News. 35(16) (2015).
Wysoczynski et al., "Lung cancer secreted microvesicles: Underappreciated modulators of microenvironment in expanding tumors." Int. J. Cancer. 125:1595-1603 (2009).
Young, Lee. International Search Report and Written Opinion for PCT/US20/20539. (Jul. 17, 2020).
Zeng et al., "Determination of the lowest concentrations of aldehyde fixatives for completely fixing various cellular structures by real-time imaging and quantification." Histochem Cell Biol 139:735-749 (2013).
Zhang et al., "Comparison in the effects of IL-2, IL-12, IL-15 and IFNα on gene regulation of granzymes of human NK cell line NK-92." International Immunopharmacology. 8:989-996 (2008).
Zhao et al., "Magnetite nanoparticles as smart carriers to manipulate the cytotoxicity of anticancer drugs: magnetic control and pH-responsive release." J. Mater. Chem., 22:15717 (2012).
Abels et al., "Introduction to Extracellular Vesicles: Biogenesis, RNA Cargo Selection, Content, Release, and Uptake." Cell Mol Neurobiol 36:301-312 (2016).
Abramowicz et al., "Proteomic analysis of exosomal cargo: the challenge of high purity vesicle isolation." Molecular Biosystems 12:1407-1419 (2016).
Admyre et al., "Direct exosome stimulation of peripheral human T cells detected by ELISPOT." Eur. J. Immunol. 36:1772-1781 (2006).
Albanese et al., "The Effect of Nanoparticle Size, Shape, and Surface Chemistry on Biological Systems." Annu. Rev. Biomed. Eng. 14:1-16 (2012).

(56) References Cited

OTHER PUBLICATIONS

Alhasan et al., "Exosome Encased Spherical Nucleic Acid Gold Nanoparticle Conjugates As Potent MicroRNA Regulation Agents." Small. 10(1): 86-192. (2014).
Alvarez et al., "Comparison of protein, microRNA, and mRNA yields using different methods of urinary exosome isolation for the discovery of kidney biomarkers." Kidney International 82:1024-1032 (2012).
Andaloussi et al., "Extracellular vesicles: biology and emerging therapeutic opportunities." Nature Reviews Drug Discovery 12:347-357 (2013).
Ariga et al., "Bioinspired Nanoarchitectonics as Emerging Drug Delivery Systems." New Journal of Chemistry 38:5120-5121 (2013).
Arslan et al., "Mesenchymal stem cell-derived exosomes increase ATP levels, decrease oxidative stress and activate PI3K/Akt pathway to enhance myocardial viability and prevent adverse remodeling after myocardial schemia/reperfusion injury." Stem Cell Research 10:301-312 (2013).
Aspe et al., "Enhancement of Gemcitabine sensitivity in adenocarcinoma by novel exosome-mediated delivery of the Survivin-T34A mutant." Journal of Extracellular Vesicles 3(1):23244 (2014).
Aubertin et al., "Massive release of extracellular vesicles from cancer cells after photodynamic treatment or chemotherapy." Scientific Reports 6:35376 (2016).
Bartolini et al., "Recombinant outer membrane vesicles carrying Chlamydia muridarum HtrA induce antibodies that neutralize chlamydial infection in vitro." Journal of Extracellular Vesicles 2(1):20181 (2013).
Benedikter et al., "Redox-dependent thiol modifications: implications for the release of extracellular vesicles." Cellular and Molecular Life Sciences 75:2321-2337 (2018).
Bhatnagar et al., "Exosomes released from macrophages infected with intracellular pathogens stimulate a proinflammatory response in vitro and in vivo." Blood 110(9):3234-3244 (2007).
Blanco et al., "Principles of nanoparticle design for overcoming biological barriers to drug delivery." Nat Biotechnol. 33(9):941-951 (2015).
Bobrie et al., "Diverse subpopulations of vesicles secreted by different intracellular mechanisms are present in exosome preparations obtained by differential ultracentrifugation." Journal of Extracellular Vesicles 1(1):18397 (2012).
Bosch et al., "Trehalose prevents aggregation of exosomes and cryodamage." Scientific Reports 6:36162 (2016).
Bunker et al., "Rational design of liposomal drug delivery systems, a review: Combined experimental and computational studies of lipid membranes, liposomes and their PEGylation." Biochimica et Biophysica Acta 1858:2334-2352 (2016).
Carvalho et al., "Doxorubicin: The Good, the Bad and the Ugly Effect." Current Medicinal Chemistry 16:3267-3285 (2019).
Charras et al., "Life and Times of a Cellular Bleb." Biophysical Journal vol. 94:1836-1853 (2008).
Chen et al., "Collateral Damage in Cancer Chemotherapy: oxidative stress in nontargeted tissues." Molecular Intervention 7(3):146-156 (2007).
Chen et al., "Chemokine-Containing Exosomes Are Released from Heat-Stressed Tumor Cells via Lipid Raft-Dependent Pathway and Act as Efficient Tumor Vaccine." Journal of Immunology 186:2219-2228 (2011).
Cheng et al., "Exosomes carrying mycobacterial antigens can protect mice against an M. tuberculosis Infection." 43(12):3279-3290 (2013).
Christianson et al., "Cancer cell exosomes depend on cell-surface heparan sulfate proteoglycans for their internalization and functional activity." PNAS 110(43):17380-17385(2013).
Clayton et al., "Induction of heat shock proteins in B-cell exosomes." Journal of Cell Science 118(16):3631-3638 (2005).
Colino et al., "Exosomes from Bone Marrow Dendritic Cells Pulsed with Diphtheria Toxoid Preferentially Induce Type 1 Antigen-Specific IgG Responses in Naive Recipients in the Absence of Free Antigen." J Immunol 177:3757-3762 (2006).

Colombo et al., "Biogenesis, Secretion, and Intercellular Interactions of Exosomes and Other Extracellular Vesicles." Annu. Rev. Cell Dev. Biol.. 30:255-89 (2014).
Conde-Vancells et al., "Characterization and Comprehensive Proteome Profiling of Exosomes Secreted by Hepatocytes." J Proteome Res. 7(12): 5157-5166 (2008).
Crescitelli et al., "Distinct RNA profiles in subpopulations of extracellular vesicles: apoptotic bodies, microvesicles and exosomes." Journal of Extracellular Vesicles 2(1):20677 (2013).
Daraee et al., "Application of liposomes in medicine and drug delivery." Artificial Cells, Nanomedicine, and Biotechnology 44: 381-391 (2016).
Del Cacho et al., "Induction of Protective Immunity against Eimeria tenella, Eimeria maxima, and Eimeria acervulina Infections Using Dendritic Cell-Derived Exosomes." Infection and Immunity 80(5):1909-1916 (2012).
Dodson et al., "Challenges in the translation and commercialization of cell therapies." BMC Biotechnology 15:70 (2015).
Dragovic et al., "Sizing and phenotyping of cellular vesicles using Nanoparticle Tracking Analysis." Nanomedicine: Nanotechnology, Biology, and Medicine 7:780-788 (2011).
Gudbergsson et al., "Systematic review of factors influencing extracellular vesicle yield from cell cultures." Cytotechnology 68:579-592 (2016).
Hadla et al., "Exosomes increase the therapeutic index of doxorubicin in breast and ovarian cancer mouse models." Nanomedicine 11(18):2431-41 (2016).
Haney et al., "Exosomes as Drug Delivery Vehicles for Parkinson's Disease Therapy." J Control Release 207:18-30 (2015).
Hannun Y. "Apoptosis and the Dilemma of Cancer Chemotherapy." Blood 89(6):1845-1853 (1997).
He et al., "Integrated immunoisolation and protein analysis of circulating exosomes using microfluidic technology." Lab Chip 14:3773-80 (2014).
Heathman et al., "The translation of cell-based therapies: clinical landscape and manufacturing challenges." Regen. Med. 10(1):49-64 (2015).
Ostrowski et al., "Rab27a and Rab27b control different steps of the exosome secretion pathway." Nature Cell Biology 12:19-30 (2010).
Pegtel et al., "Functional delivery of viral miRNAs via exosomes." PNAS 107(14): 6328-6333 (2010).
Piffoux et al., "Extracellular vesicles for personalized medicine: the input of physically triggered production, loading and theranostic properties." Adv Drug Deliv Rev 138:247-258 (2019).
Prabaharan et al., "Gold nanoparticles with a monolayer of doxorubicin-conjugated amphiphilic block copolymer for tumor-targeted drug delivery." Biomaterials 30:6065-6075 (2009).
Prokop et al., "Nanovehicular Intracellular Delivery Systems." J Pharm Sci. 97(9): 3518-3590 (2008).
Rabouille, C. "Pathways of Unconventional Protein Secretion." Trends in Cell Biology 27(3):230-240 (2017).
Raiborg et al., "Protein sorting into multivesicular endosomes." Current Opinion in Cell Biology 15:446-455 (2003).
Rani et al., "Mesenchymal Stem Cell-derived Extracellular Vesicles: Toward Cell-free Therapeutic Applications." Mol Ther. 23(5): 812-823 (2015).
Riazifar et al., "Stem Cell Extracellular Vesicles: Extended Messages of Regeneration." Annu. Rev. Pharmacol. Toxicol.57:125-54 (2017).
Robert et al., "High-Sensitivity Flow Cytometry Provides Access to Standardized Measurement of Small-Size Microparticles—Brief Report." Arterioscler Thromb Vasc Biol 32(4):1054-8 (2012).
Roux et al., "Membrane curvature controls dynamin polymerization." PNAS 107(9):4141-4146 (2010).
Rupert et al., "Determination of Exosome Concentration in Solution Using Surface Plasmon Resonance Spectroscopy." Analytical Chemistry 86:5929-5936 (2014).
Saari et al., "Microvesicle- and exosome-mediated drug delivery enhances the cytotoxicity of Paclitaxel in autologous prostate cancer cells." Journal of Controlled Release 220:727-737 (2015).
Sadauskas et al., "Kupffer cells are central in the removal of nanoparticles from the organism." Particle and Fibre Toxicology 4(10):1-7 (2007).

(56) References Cited

OTHER PUBLICATIONS

Sahay et al., "Endocytosis of Nanomedicines." J Control Release 145(3):182-195 (2010).
Sahay et al., "Efficiency of siRNA delivery by lipid nanoparticles is limited by endocytic recycling." Nat Biotechnol 31(7): 653-658 (2013).
Savina et al., "Rab11 Promotes Docking and Fusion of Multivesicular Bodies in a Calcium-Dependent Manner." Traffic 6:131-143 (2005).
Savla et al., "Tumor targeted quantum dot-mucin 1 aptamer-doxorubicin conjugate for imaging and treatment of cancer." Journal of Controlled Release 153:16-22 (2011).
Semple et al., "Interactions of liposomes and lipid-based carrier systems with blood proteins: Relation to clearance behaviour in vivo." Advanced Drug Delivery Reviews 32:3-17 (1998).
Shelke et al., "Importance of exosome depletion protocols to eliminate functional and RNA-containing extracellular vesicles from fetal bovine serum." Journal of Extracellular Vesicles 3:24783 (2014).
Shimoda et al., "Exosomes as nanocarriers for systemic delivery of the Helicobacter pylori virulence factor CagA." Scientific Reports 6:18346 (2016).
Shtam et al., "Exosomes are natural carriers of exogenous siRNA to human cells in vitro." Cell Communication and Signaling 11:88 (2013).
Simons et al., "Functional rafts in cell membranes." Nature 387:569-572 (1997).
Smith et al., "Measurement of Protein Using Bicinchoninic Acid." Analytical Biochemistry 150:76-85 (1985).
Soo et al., "Nanoparticle tracking analysis monitors microvesicle and exosome secretion from immune cells." Immunology 136:192-197 (2012).
Staykova et al., "Mechanics of surface area regulation in cells examined with confined lipid membranes." PNAS 108(22):9084-9088 (2011).
Suk et al., "PEGylation as a strategy for improving nanoparticle-based drug and gene delivery." Adv Drug Deliv Rev. 99(Pt A):28-51 (2016).
Takahashi et al., "Exosomes maintain cellular homeostasis by excreting harmful DNA from cells." Nature Communications 8(1):1-16 (2017).
Tang et al., "Mesenchymal Stem Cell Derived ExosomesThe Potential for Translational Nanomedicine." Academic Press, 2015.
Tauro et al., "Comparison of ultracentrifugation, density gradient separation, and immunoaffinity capture methods for isolating human colon cancer cell line LIM1863-derived exosomes." Methods 56:293-304 (2012).
Thanh et al., "Functionalisation of nanoparticles for biomedical applications." Nano Today 5:213-230 (2010).
Thone et al., "Extracellular blebs: Artificially-induced extracellular vesicles for facile production and clinical translation." Methods 177:135-145 (2020).
Tian et al., "Surface functionalized exosomes as targeted drug delivery vehicles for cerebral ischemia therapy." Biomaterials 150:137-149 (2018).
Wang et al., "Ciliated micropillars for the microfluidic-based isolation of nanoscale lipid vesicles." Lab Chip 13(15):2879-2882 (2013).
Wiklander et al., "Extracellular vesicle in vivo biodistribution is determined by cell source, route of administration and targeting." Journal of Extracellular Vesicles 4:26316 (2015).
Wilhelm et al., "Analysis of nanoparticle delivery to tumours." Nature Reviews Materials 1:6014 (2016).
Witwer et al., "Standardization of sample collection, isolation and analysis methods in extracellular vesicle research." Journal of Extracellular Vesicles 2:20360 (2013).
Wong et al., "Synthetically Functionalized Retroviruses Produced from the Bioorthogonally Engineered Cell Surface." Bioconjugate Chemistry 22(2):151-155 (2011).
Wubbolts et al., "Proteomic and Biochemical Analyses of Human B Cell-derived Exosomes." The Journal of Biological Chemistry 278(13):10963-10972 (2003).
Enderle et al., "Characterization of RNA from Exosomes and Other Extracellular Vesicles Isolated by a Novel Spin col. Based Method." PLOS ONE 10(8):e0136133 (2015).
Gangoda et al., "Cortactin enhances exosome secretion without altering cargo." The Journal of Cell Biology 214(2):129-131 (2016).
Villarroya-Beltri et al., "ISGylation controls exosome secretion by promoting lysosomal degradation of MVB proteins." Nature Communications 7:13588 (2016).

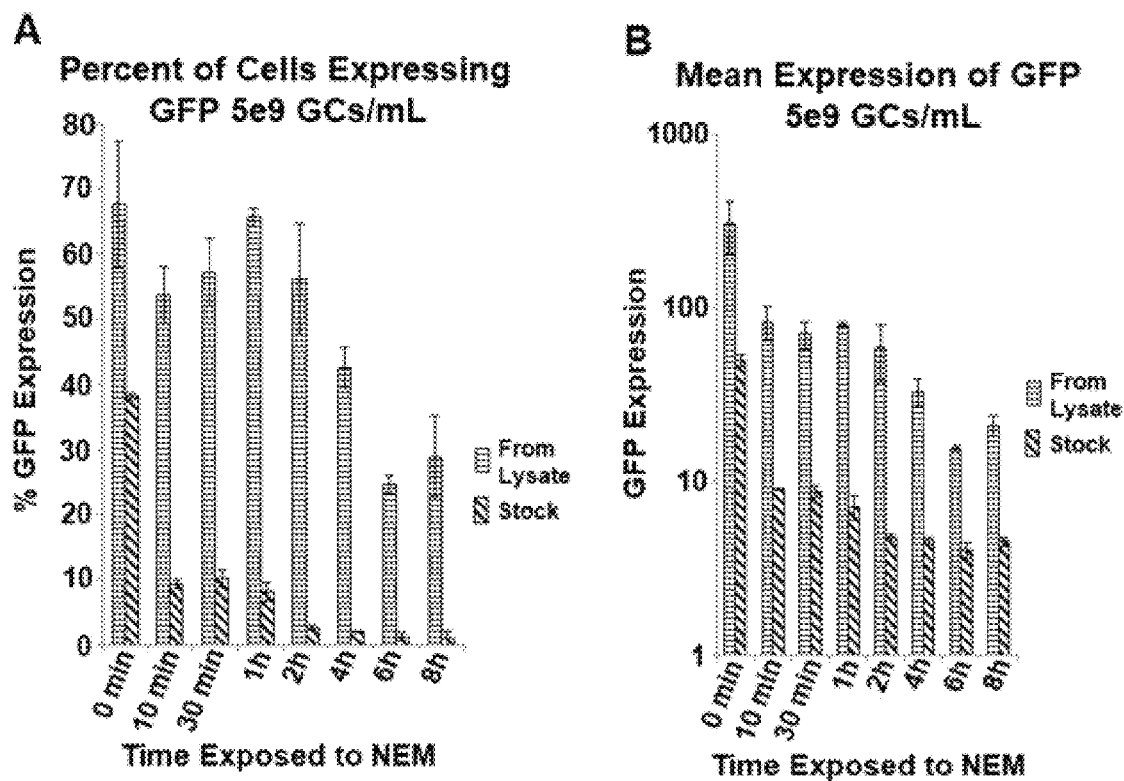
FIG. 38A-B
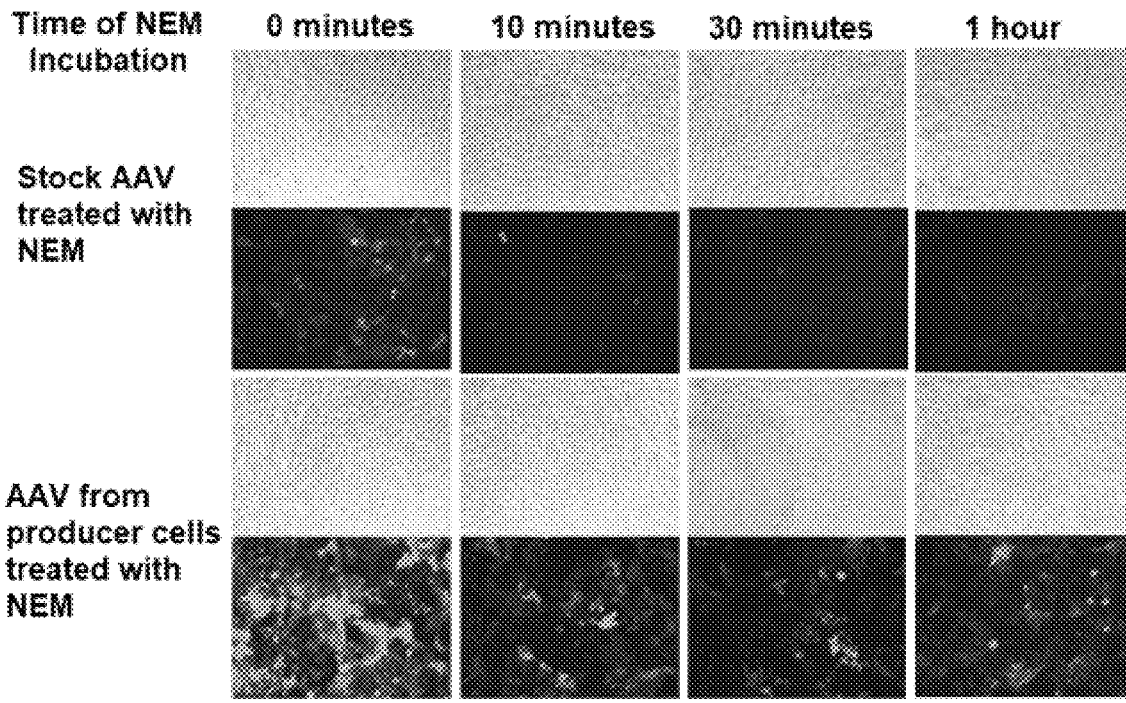
FIG. 39

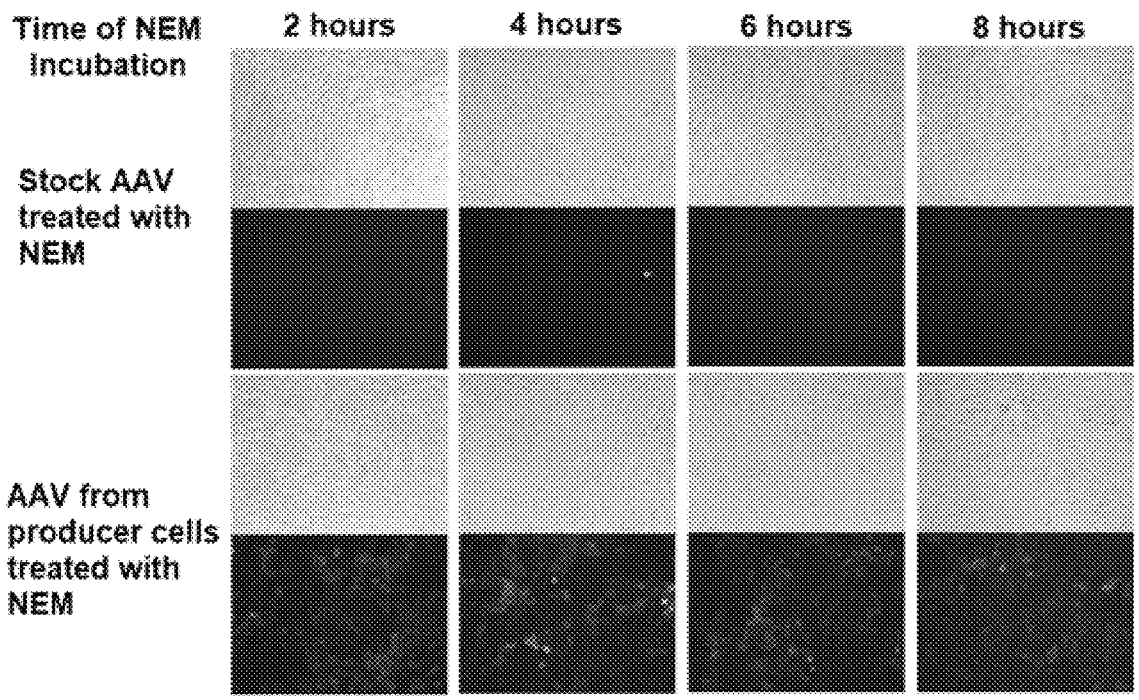
FIG. 40
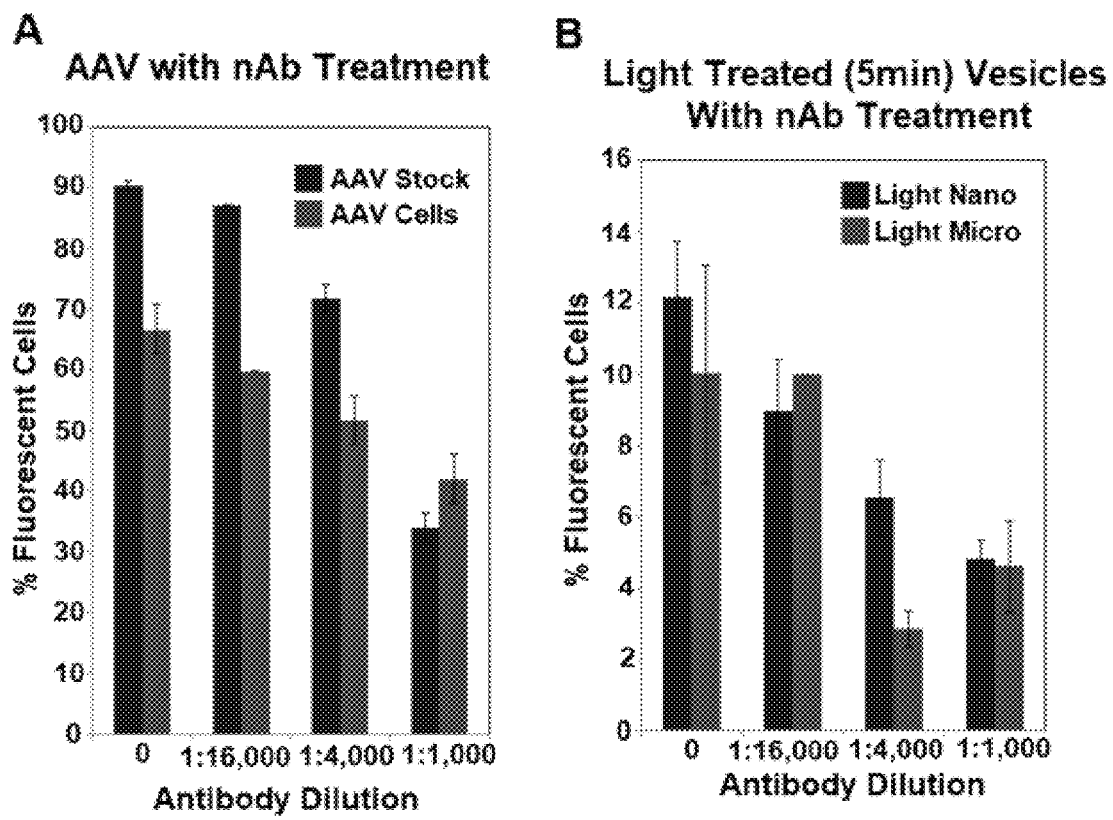
FIG. 41A-B

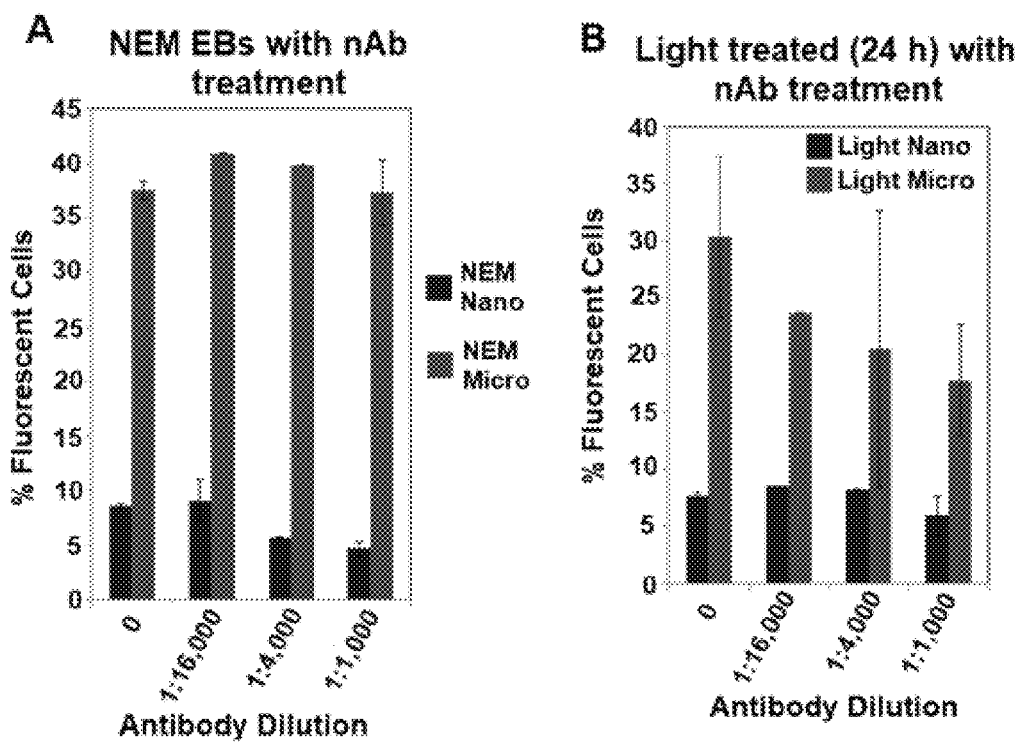
FIG. 42A-B
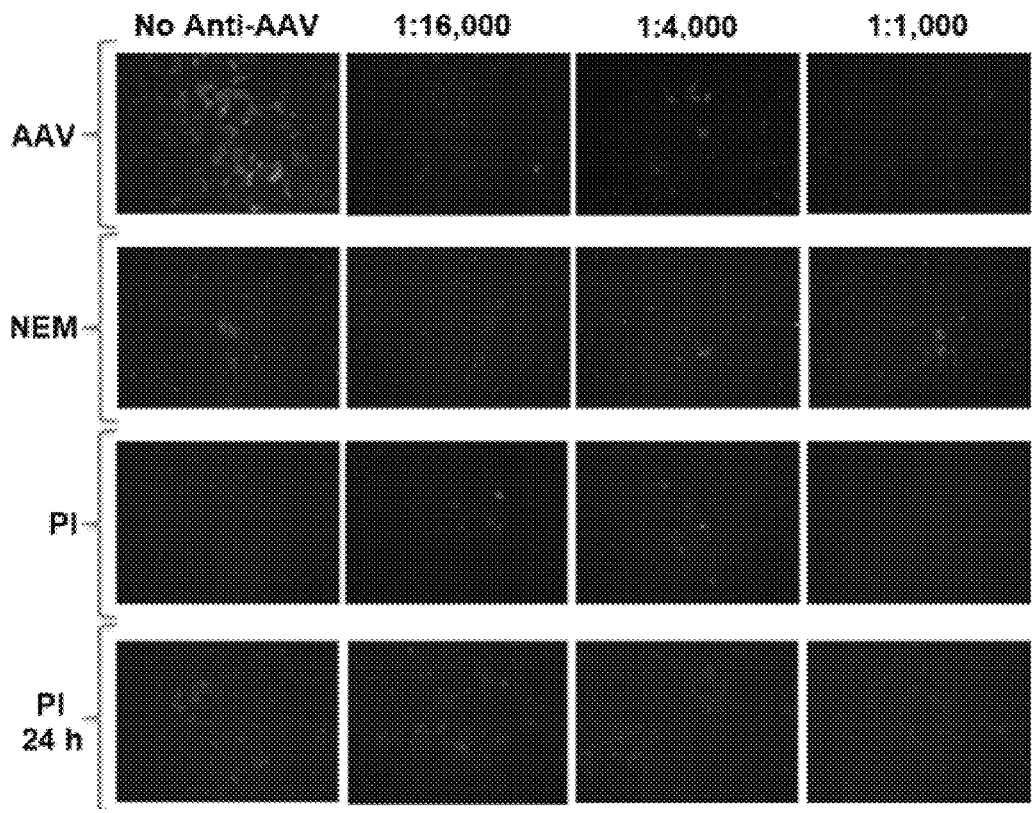
FIG. 43

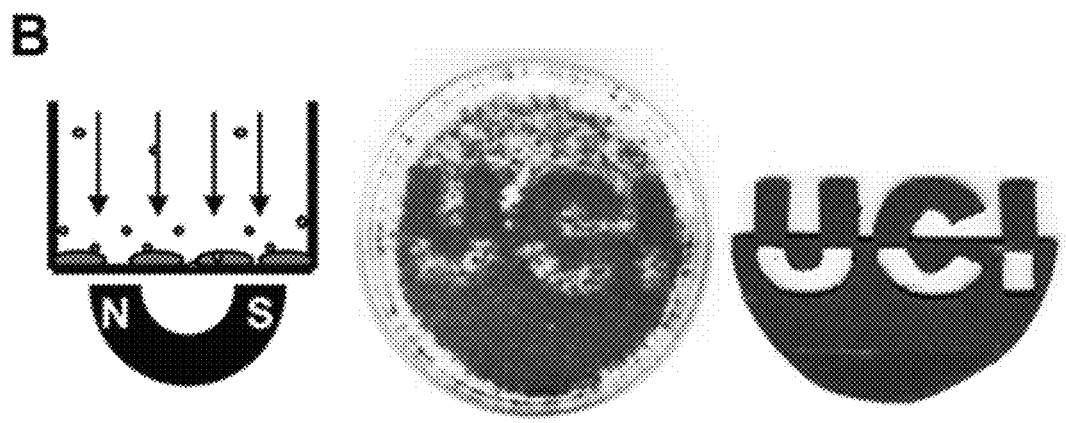
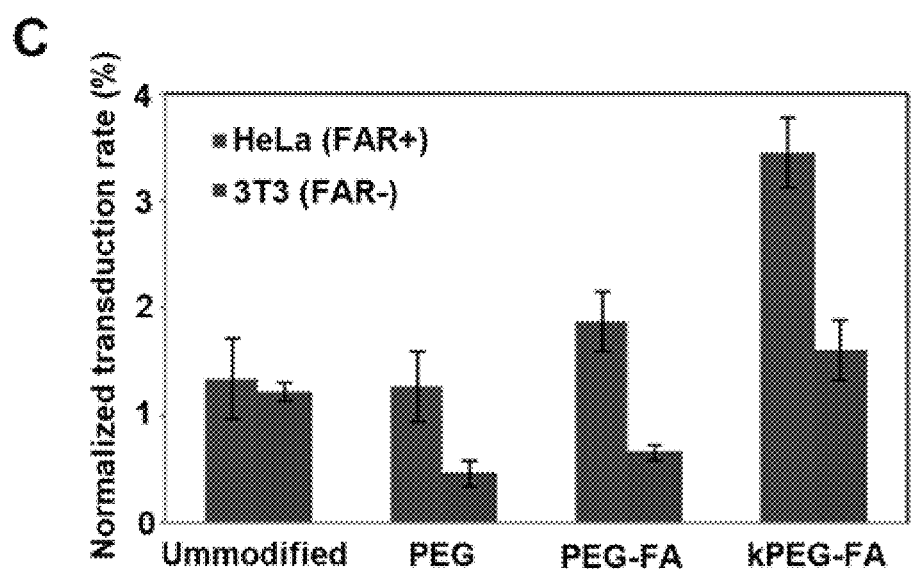
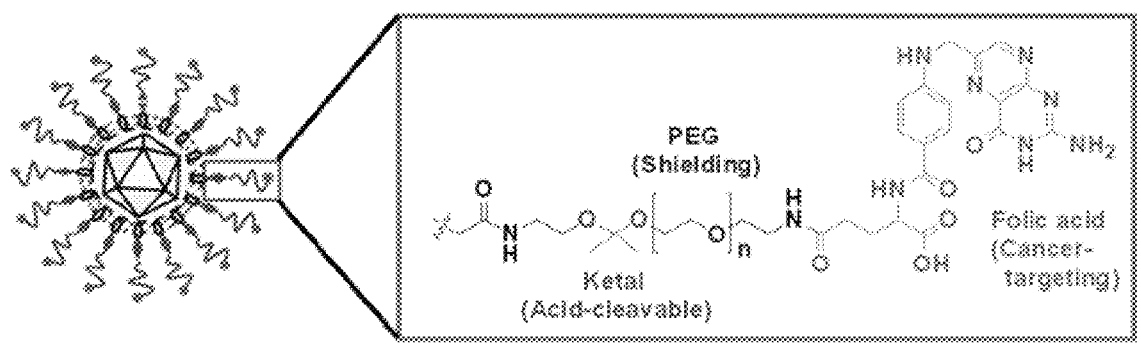
FIG. 47B-C

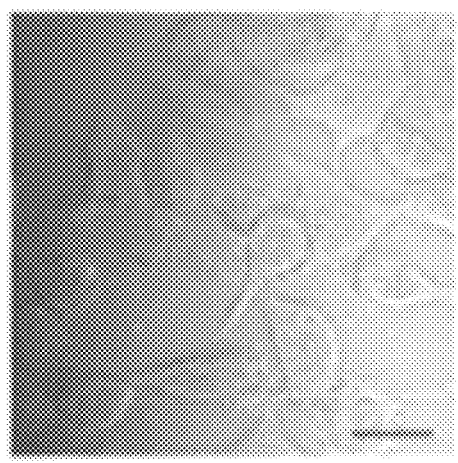
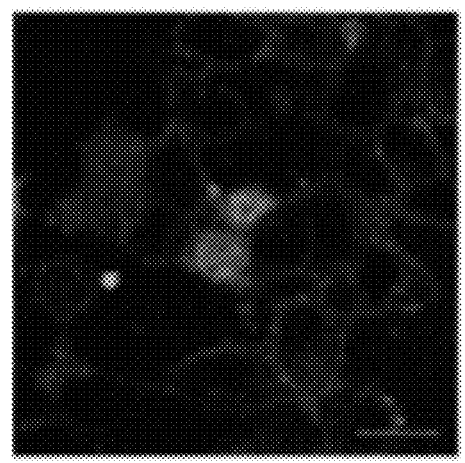
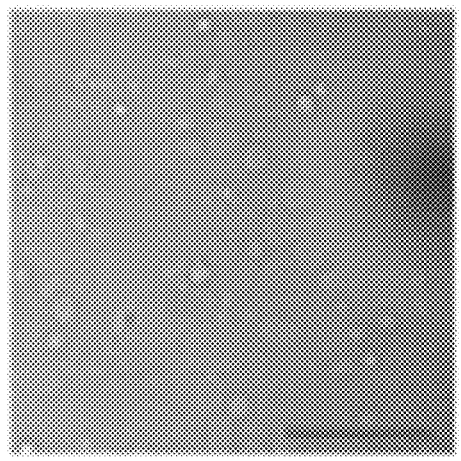
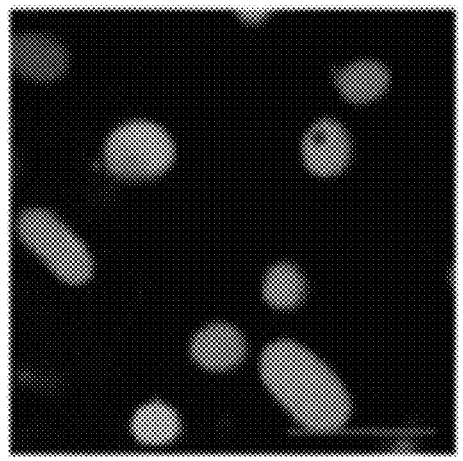
*FIG. 48A-B*

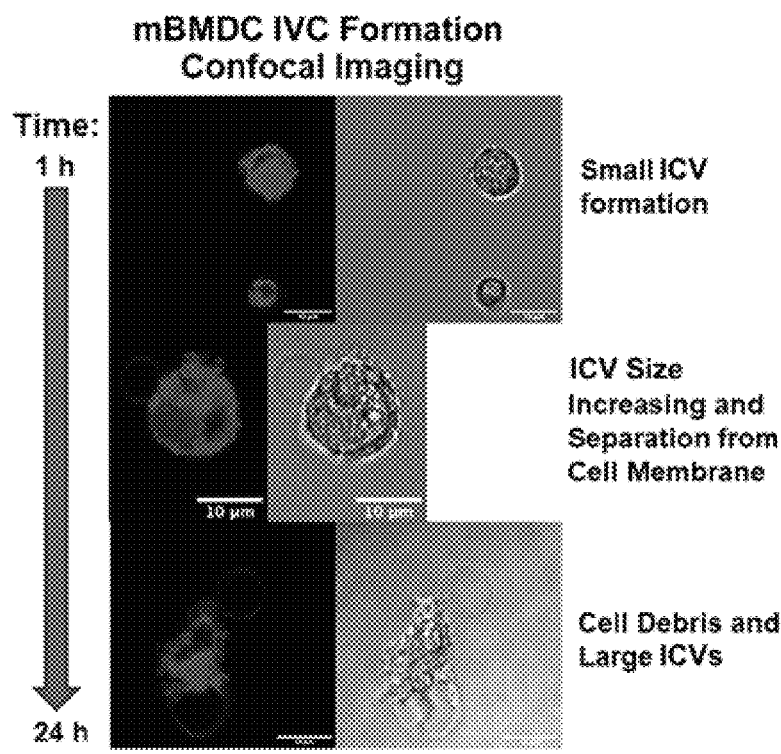
FIG. 57
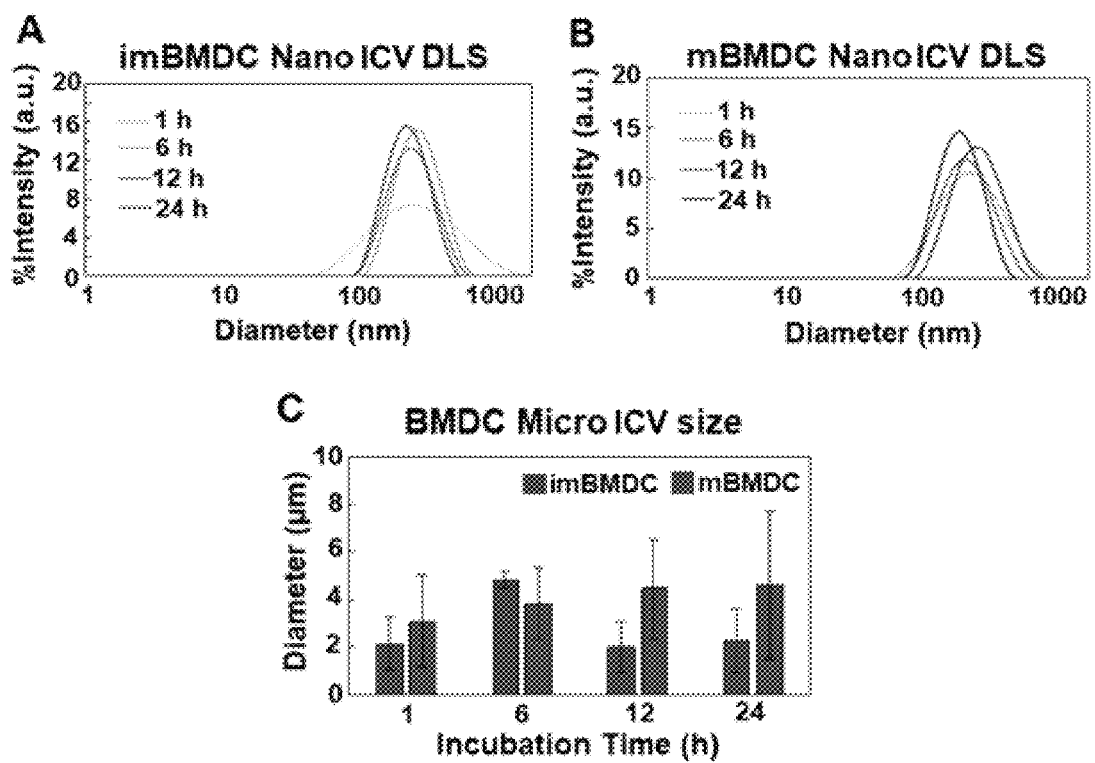
FIG. 58A-C

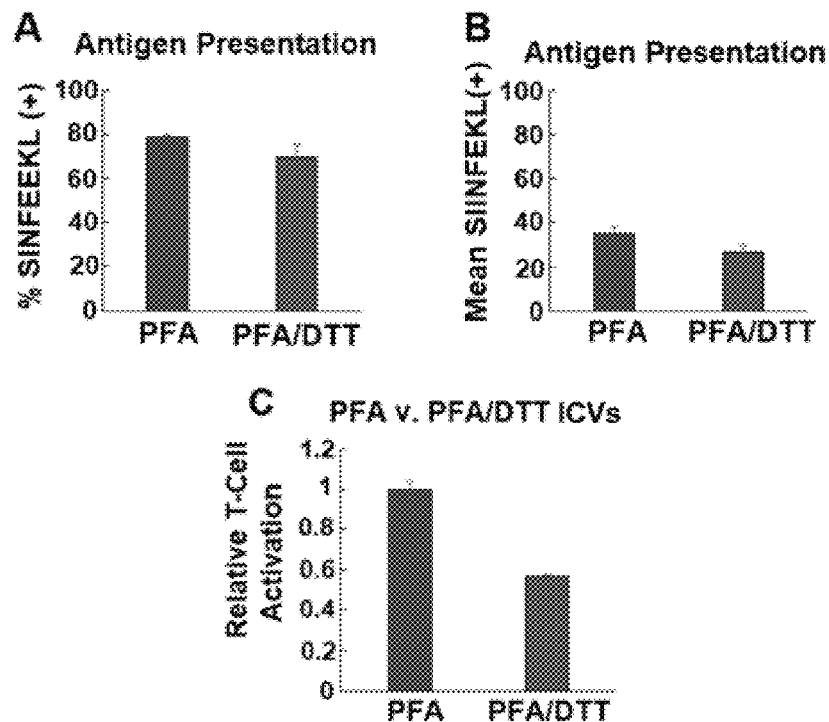
FIG. 59A-C
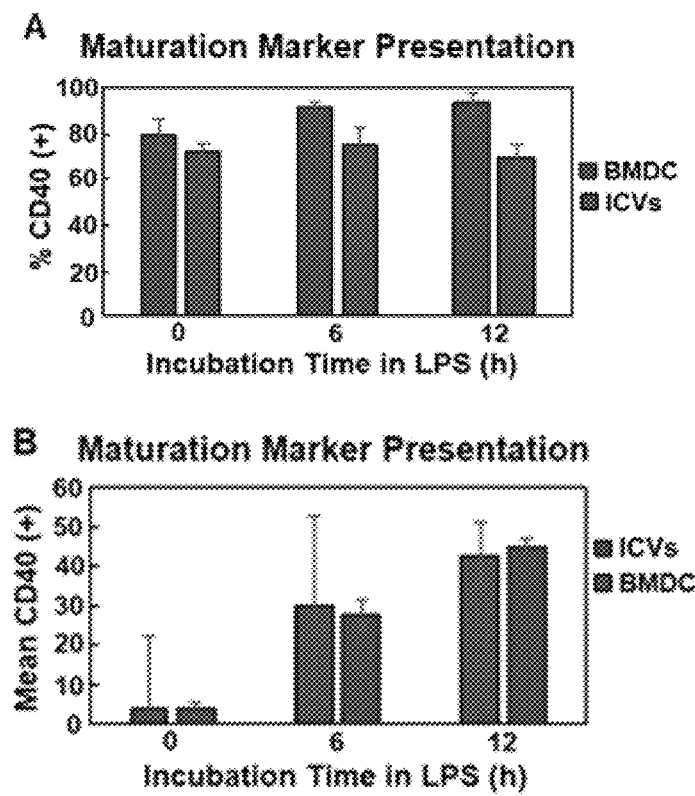
FIG. 60A-B

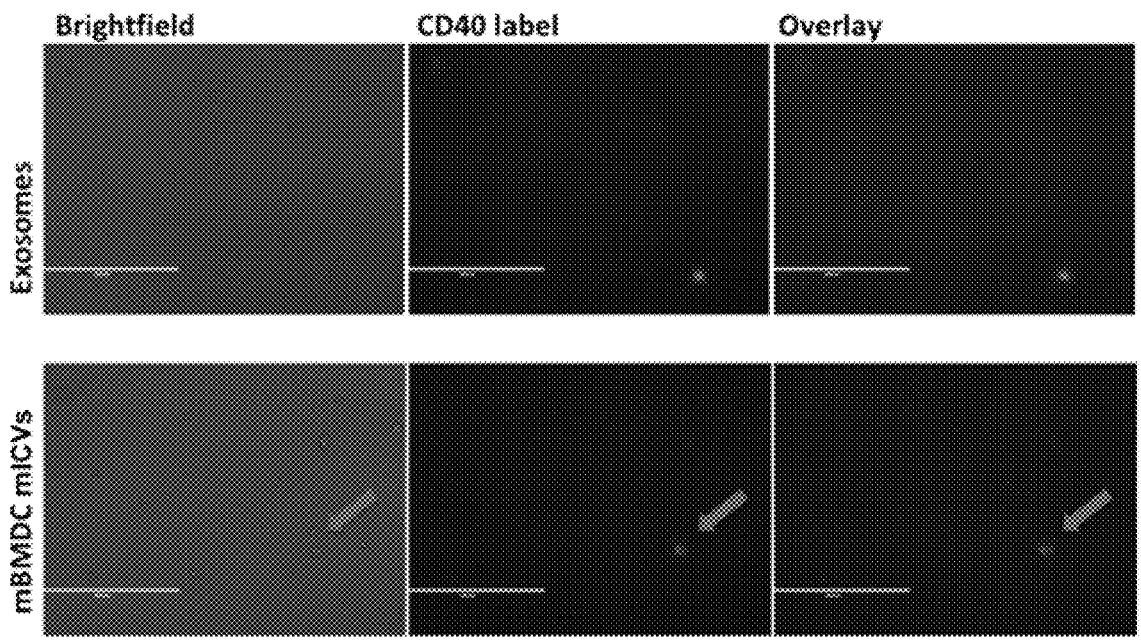
FIG. 61
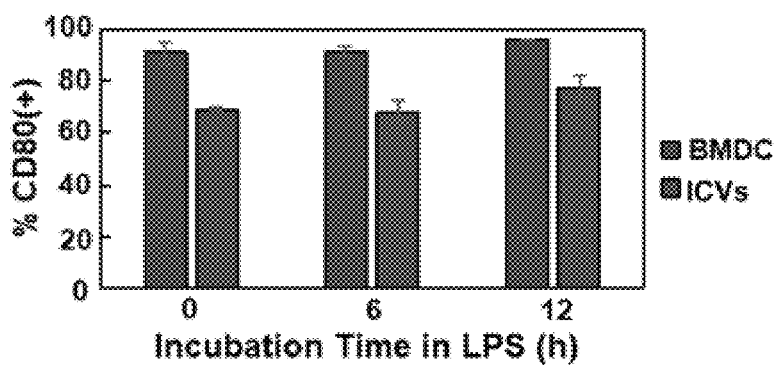
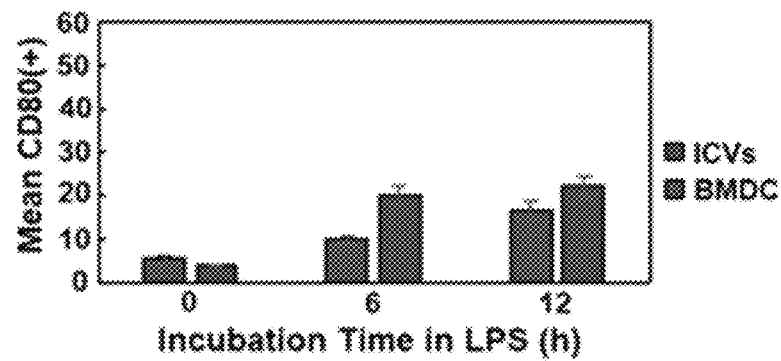
FIG. 62A-B

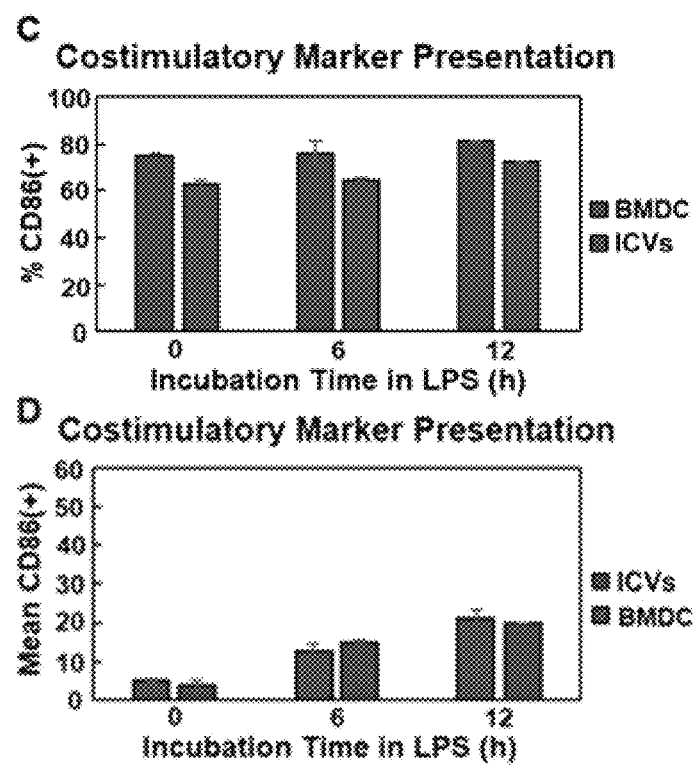
FIG. 62C-D
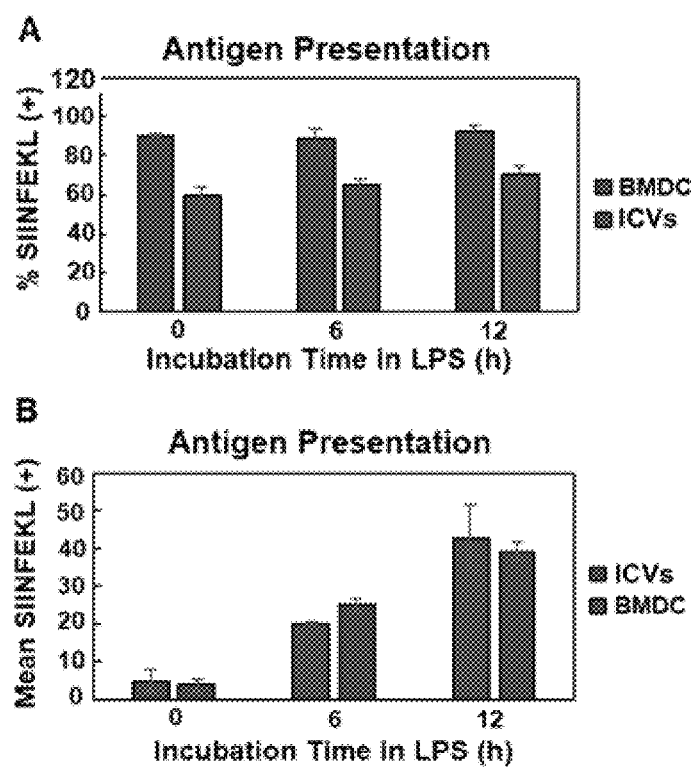
FIG. 63A-B

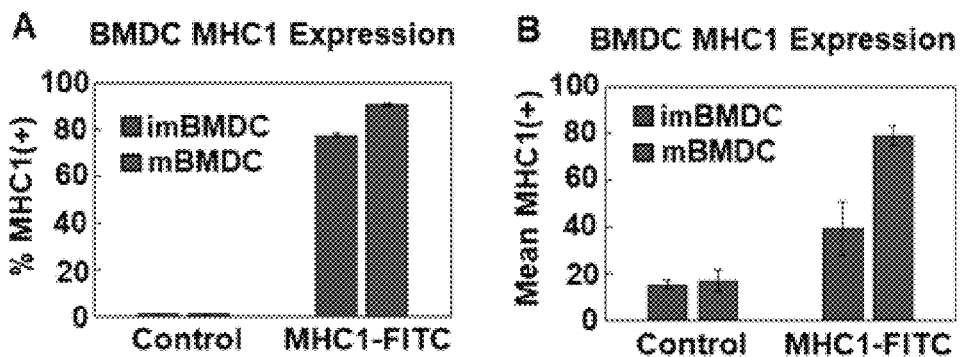
FIG. 64A-B
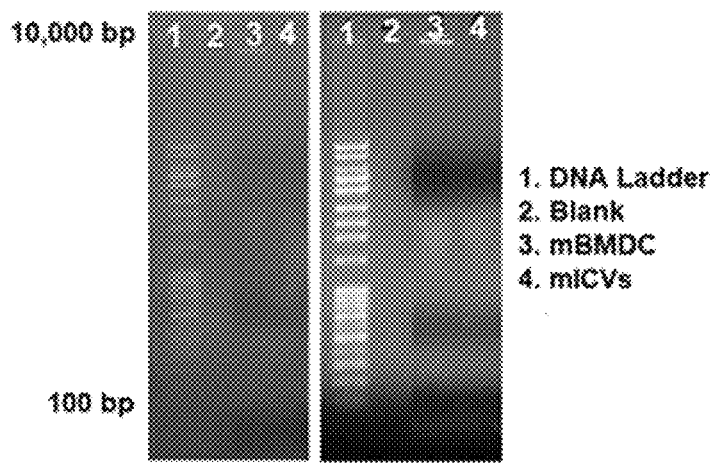
FIG. 65
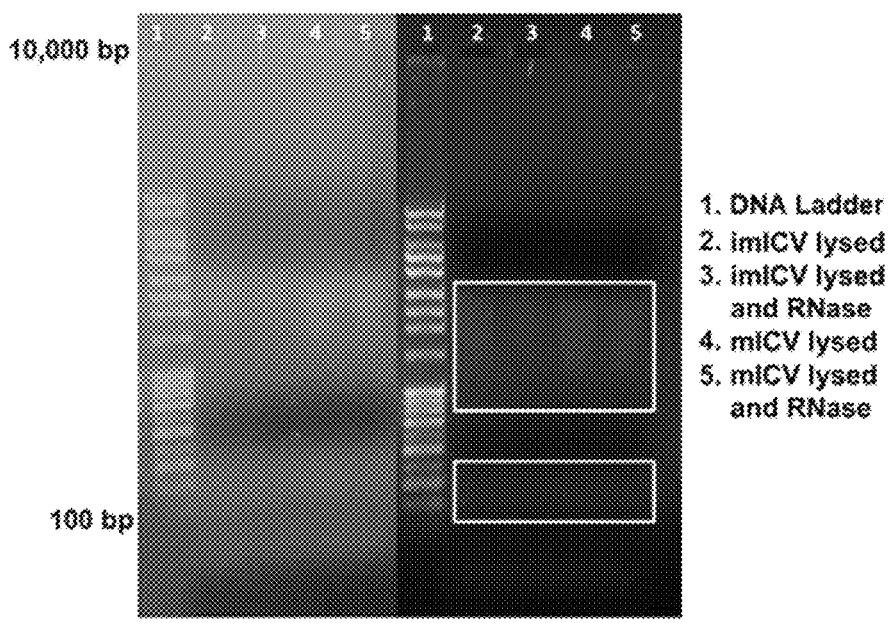
FIG. 66

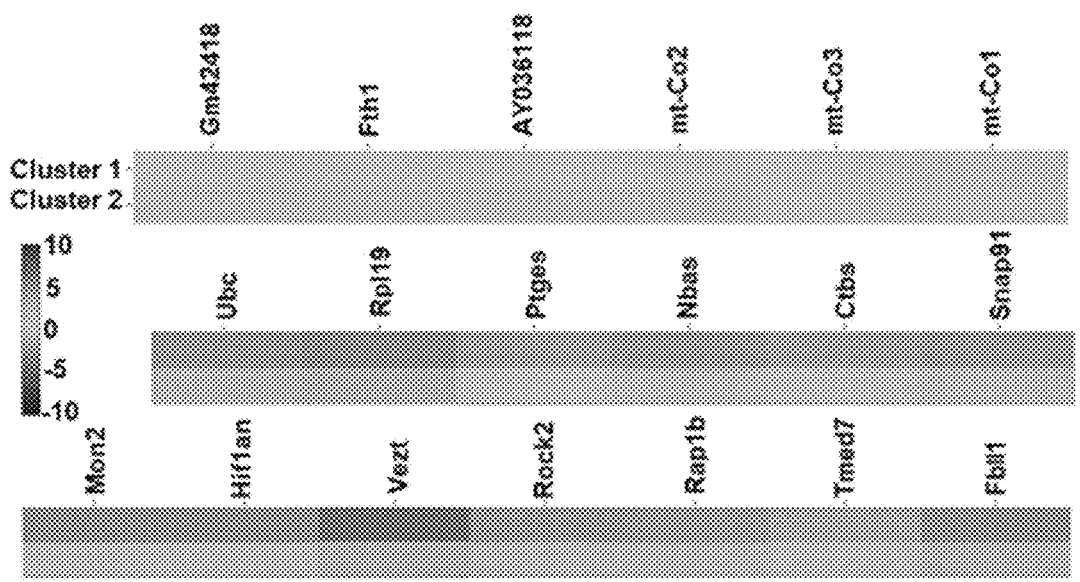
*FIG. 69*
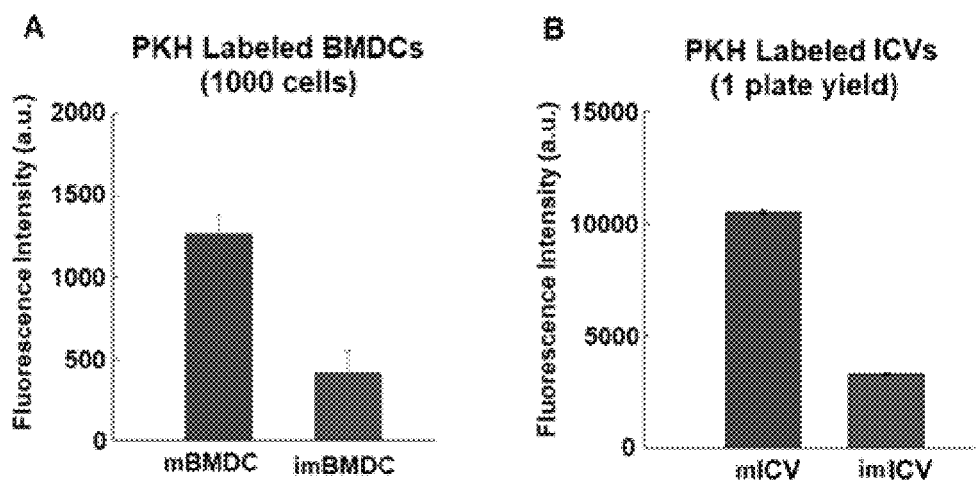
*FIG. 70A-B*
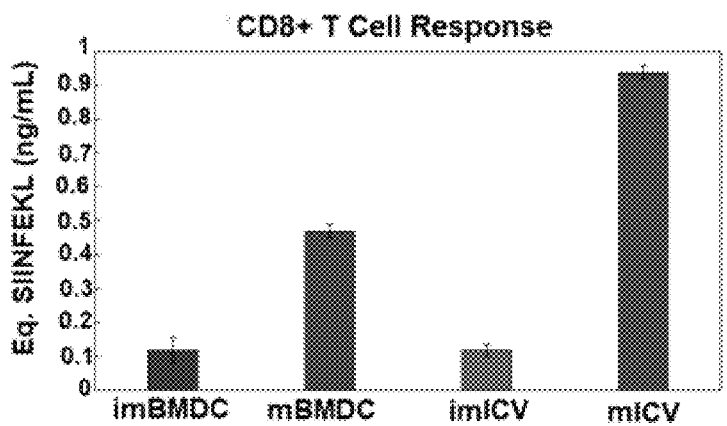
*FIG. 71*

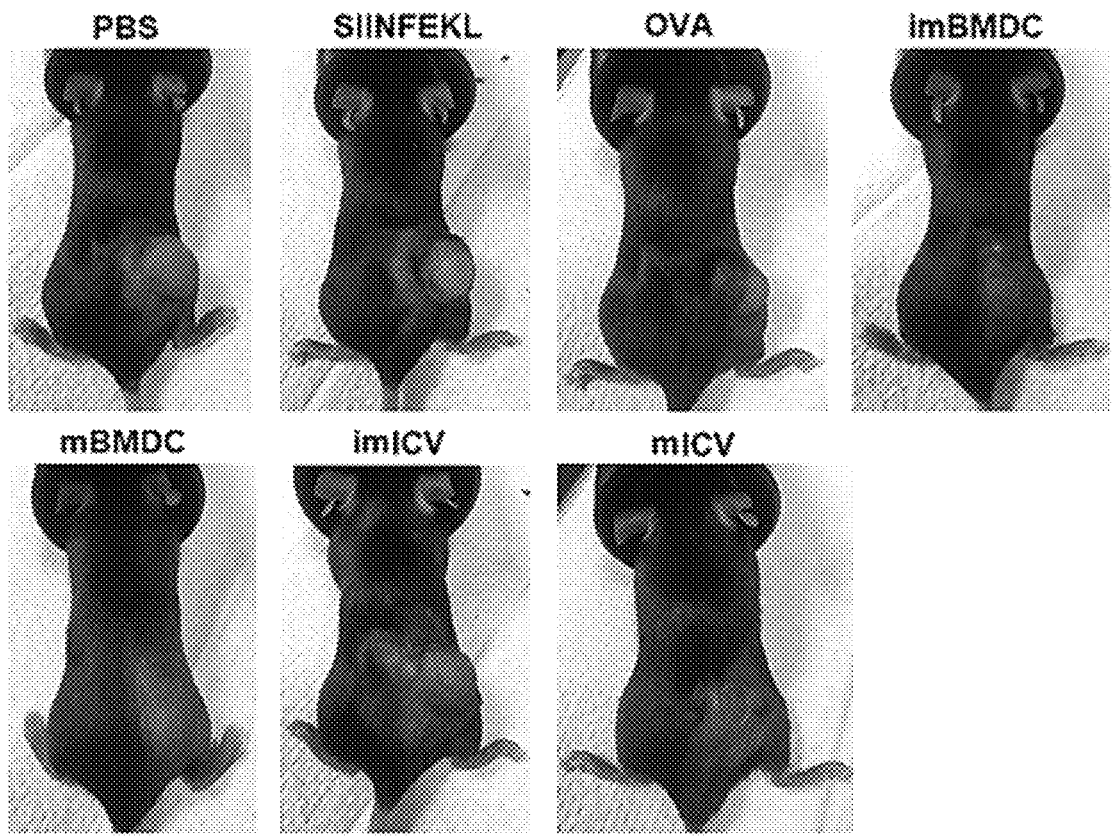
FIG. 72
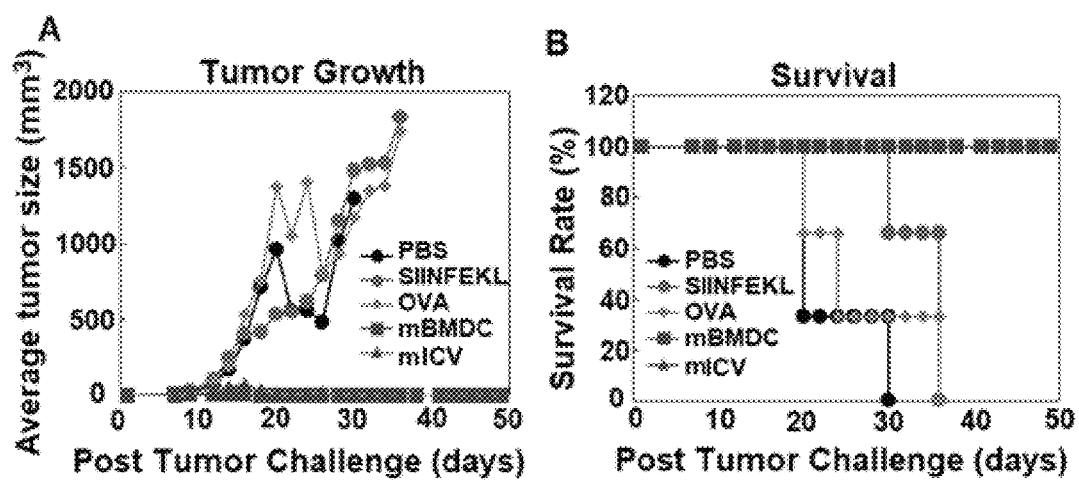
FIG. 73A-B

CHEMICALLY AND PHOTOCHEMICALLY INITIATED CELL MEMBRANE BLEBBING TO INDUCE CELL VESICLE PRODUCTION, MODIFICATIONS THEREOF, AND USES THEREOF

CROSS REFERENCE TO RELATED APPLICATIONS

This application is a U.S. National Stage Application filed under 35 U.S.C. § 371 and claims priority to International Application No. PCT/US2019/46968, filed Aug. 16, 2019, which application claims priority under 35 U.S.C. § 119 from Provisional Application Ser. Nos. 62/765,034, 62/765,064, 62/765,102, and 62/765,063, which were filed on Aug. 16, 2018, and from Provisional Application Ser. No. 62/735,830, filed on Sep. 24, 2018, the disclosures of which are incorporated herein by reference.

STATEMENT OF GOVERNMENT SUPPORT

This invention was made with Government support under Grant No. DGE-1321846, awarded by the National Science Foundation, and Grant No. 5T32AI7319-29, awarded by the National Institutes of Health. The Government has certain rights in the invention.

TECHNICAL FIELD

The disclosure provides methods to chemically and photochemically initiate cell membrane blebbing to induce cell vesicle production, modifications thereof, and uses thereof, including for drug delivery, gene therapy, cell-free cell therapy, and molecular therapy.

BACKGROUND

The field of drug delivery relies on nanometer scale carriers for effective delivery of cargo to a designated target site. These carriers play two roles: to protect cargo during transport and release cargo at the appropriate site without inducing immunogenic response. While many nano-carriers have been designed, issues with immunogenicity, toxicity, poor biocompatibility, and low efficacy of delivery still remain major challenges in the field.

Viral gene therapy is a method to directly target mutations at a molecular level. Its ability to selectively treat mutated cells offers opportunities for decreased off target effects and increased efficacy over traditional treatments. However, the major hurdle in this treatment is designing the ideal delivery vehicle, one that is effective but also safe. Viruses are effective at delivering genes into the nucleus of the cell, but are easily recognized by the immune system, which can lead to increased side effects and rapid clearance. Adeno-associated virus (AAV) has been used increasingly as a promising vector for viral gene therapy. AAV is a small, non-enveloped virus that can transduce both dividing and quiescent cells, making it useful for many applications in viral gene therapy. The host's immune response to AAV is not a systemic response, and is limited to neutralizing antibodies, which leads to clearance, but no side effects. AAV is also non-pathogenic and therefore generally regarded as safe. Therefore, AAV has great potential in viral gene therapy if shielded from the immune system during transport.

Cancer cells survive and proliferate by several mechanisms including immune evasion. Immunotherapy overcomes this by activating the immune system to eliminate cancer cells. The most common strategy for activating the immune system against tumor cells is vaccination with tumor antigens. Previous studies have reported that bone marrow dendritic cells (BMDCs) pulsed with an antigen ex vivo are able to act as an anti-cancer vaccine, presenting an antigen in vivo and stimulating T cell response to eradicate tumor cells. However, intrinsic variability associated with whole-cell vaccine formulations has made them non-ideal candidates for immunotherapy.

SUMMARY

Extracellular vesicles (EVs) are cell membrane derived particles that show significant promise in the field of drug delivery as micro- and nano-scale carrier agents. Despite their high potential, EV-based therapeutics have been slow to progress to clinical trials due to issues with mass production. It was found herein that mass-scale production of micro and nanoscale cell vesicles could be induced by use of a sulfhydryl blocking agent or a photosensitizer that promotes cell blebbing. The techniques presented herein induce cell vesicle formation significantly faster, more efficiently, and in a higher yield than current vesicle production techniques.

Adeno-associated virus has become an increasingly popular vector for viral gene therapy. Free-AAV in the body, however, will be recognized by antibodies, resulting in clearance. Therefore, in order to use AAV, a shield or carrier is important. Under normal cellular processes, extracellular vesicles can incorporate AAV thereby shielding AAV in the host's body and providing for enhanced efficacy, however, the production yields of such vesicles is extremely low. The disclosure provides for methods and agents which overcome the forgoing challenges by (1) the use of an AIPCS2A photosensitizer and 670 nm light, or (2) the use of sulfhydryl blocking agent to initiate mass-scale production of micro and nanoscale AAV-containing cell vesicles. The methods and techniques of the disclosure induce cell vesicle formation faster, more efficiently, and at higher yields compared to current AAV-containing-vesicle production techniques.

The methods of the disclosure also provide for modification of induced cell vesicles (ICVs) described herein by oxime ligation of aminooxy-functionalized molecules with aldehyde groups of oxidized sialylated glycoproteins on the cell surface of producer or host cells. As mammalian cells naturally display sialic acids on their surface of their cells, albeit at different levels (e.g., particularly elevated sialic acid expression by cancer cells), the methods disclosed herein, by using bioorthogonal cell surface modification, generated molecularly functionalized cell vesicles in a simple, fast, and efficient way.

Antigen-pulsed bone marrow dendritic cells have shown promise as cancer vaccines. Variability in production of cell-based vaccines is problematic, and whole cell vaccines are challenging to store efficiently. Extracellular vesicles derived from immune cells are promising cancer vaccines, but extracellular vesicle-based immunotherapy has not progressed to clinical trials in part due to issues with heterogeneity. In the studies presented herein, cell vesicles induced from bone marrow dendritic cells using the methods of disclosure provided for antigenic cellular vesicles that could be locked at a specific maturation stage, or antigenic profile. The use of such antigenic cell vesicles could be used for cell-free therapies, including for cancer vaccination. It was shown herein, that antigenic mICVs produced by sulfhydryl blocking, maintained maturation characteristics of their parent cells, leading to enhanced immunotherapy outcomes. In tumor-challenged C57BL/6 mice, antigenic mICVs performed as well as whole cell therapy in terms of slowing tumor growth and improving survival while providing a safer, cell-free alternative.

As shown in the studies presented herein, the disclosure provides for a platform technology for the production of ICVs from cells using the blebbing methods and techniques described herein. In particular, the ICVs can be produced from nearly any type of cell, in any state of maturation or activation, in a highly efficient and rapid manner, and in mass scale. Further, the studies presented herein establish that the blebbing methods and techniques of the disclosure can be tailored to control the size of ICVs produced (e.g., from 10 nm to 10 μm) from the cells; and also demonstrate that the surfaces of the ICVs can be engineered using synthetic techniques (e.g., bioorthogonal conjugation) to add additional functionalities to the ICVs, such as modifying the surface of the ICVs to comprise targeting and therapeutic moieties. The blebbing methods and techniques described herein thus allow for designing or tailoring ICVs to treat specific disease indications by customizing the ICVs with various surface proteins and/or cargoes. As such, an engineering biology approach can be used to iteratively design, build, and test 'customized' ICVs to treat specific diseases and conditions by using synthetic biology to vary the surface composition of the ICVs and/or cargoes. These 'customized' ICVs would be expected to have higher potencies and efficacies for the targeted diseases and conditions than standardly used modalities. Moreover, these 'customized' ICVs can be used in any number of formulations to test the effectiveness of the 'customized' ICVs in any number of different types of disease models ranging from cancer to autoimmune disease to gene therapy, etc. Thus, the blebbing methods and techniques described herein provide tremendous flexibility to develop unique ICVs formulations that are highly specific and potent for a given disease indication.

In a particular embodiment, the disclosure provides a method to produce induced cell vesicles (ICVs) or antigenic ICVs, comprising: inducing cell vesicle production from cells by exposing or contacting the cells with a cell blebbing buffer which comprises a sulfhydryl blocking agent or a photosensitizer; wherein antigenic ICVs are produced from antigen presenting cells which can stimulate T-cell activation. In a further embodiment, the cells are from a mammal. In yet a further embodiment of any of the foregoing embodiments, the cells are from a human. In yet a further embodiment of any of the foregoing embodiments, the cells are from a human patient that has a disorder or disease that is to be treated with ICVs or antigenic ICVs produced therefrom. In yet a further embodiment of any of the foregoing embodiments, the cells are selected from epithelial cells, fibroblast cells, tumor cells, mast cells, T and B lymphocytes, dendritic cells, and Langerhans cells. In yet a further embodiment of any of the foregoing embodiments, the antigenic ICVs are produced from dendritic cells. In yet a further embodiment of any of the foregoing embodiments, the dendritic cells are bone marrow dendritic cells (BMDCs). In yet a further embodiment of any of the foregoing embodiments, wherein the BMDCs are immature BMDCs. In yet a further embodiment of any of the foregoing embodiments, wherein the BMDCs are mature BMDCs. In yet a further embodiment of any of the foregoing embodiments, wherein the induced cell vesicles comprise viruses, viral particles, or viral vectors, by being produced from cells comprising the same. In yet a further embodiment of any of the foregoing embodiments, wherein the viruses, viral particles, or viral vectors are selected from recombinant retroviruses, adenoviruses, adeno-associated viruses (AAV), alphaviruses, and lentiviruses. In yet a further embodiment of any of the foregoing embodiments, wherein the viruses, viral particles, or viral vectors are AAV. In yet a further embodiment of any of the foregoing embodiments, wherein the AAV expresses a heterologous transgene that is used for gene therapy. In yet a further embodiment of any of the foregoing embodiments, wherein the cell blebbing buffer does not contain any small molecule redox reagents or reducing agents. In yet a further embodiment of any of the foregoing embodiments, wherein the cell blebbing buffer comprises a buffered balanced salt solution. In yet a further embodiment of any of the foregoing embodiments, wherein the buffered balanced salt solution selected from the group consisting of phosphate-buffered saline (PBS), Dulbecco's Phosphate-buffered saline (DPBS), Earle's Balanced Salt solution (EBSS), Hank's Balanced Salt Solution (HBSS), TRIS-buffered saline (TBS), and Ringer's balanced salt solution (RBSS). In yet a further embodiment of any of the foregoing embodiments, wherein the cell blebbing buffer comprises a 1× to 10× concentration/dilution of the buffered balanced salt solution. In yet a further embodiment of any of the foregoing embodiments, wherein the cell blebbing buffer comprises a 1× to 5× concentration/dilution of DPBS. In yet a further embodiment of any of the foregoing embodiments, wherein the cells are incubated in the cell blebbing buffer which comprises a sulfhydryl blocking agent for 0.5 h to 48 h. In yet a further embodiment of any of the foregoing embodiments, wherein the cells are incubated in the cell blebbing buffer for 1 h to 8 h at 37° C. In yet a further embodiment of any of the foregoing embodiments, wherein the sulfhydryl blocking agent is selected from the group consisting of and N-ethylmaleimide, paraformaldehyde, mercury chloride, p-chloromercuribenzene sulfonic acid, auric chloride, p-chloromercuribenzoate, chlormerodrin, meralluride sodium, and iodoacetamide. In yet a further embodiment of any of the foregoing embodiments, wherein the sulfhydryl blocking agent is N-ethylmaleimide (NEM) or maleimide. In yet a further embodiment of any of the foregoing embodiments, wherein the cell blebbing buffer comprises from 1 mM to 10 mM of NEM. In yet a further embodiment of any of the foregoing embodiments, wherein the cell blebbing buffer consists essentially of 2 mM NEM in DPBS. In yet a further embodiment of any of the foregoing embodiments, wherein the cell blebbing buffer comprises paraformaldehyde. In yet a further embodiment of any of the foregoing embodiments, wherein the cell blebbing buffer comprises 25 mM of paraformaldehyde. In yet a further embodiment of any of the foregoing embodiments, wherein the cells are incubated with or exposed to a photosensitizer having a concentration of 0.5 ug/mL to 5.0 ug/mL. In yet a further embodiment of any of the foregoing embodiments, wherein the cells are incubated with or exposed to a photosensitizer having a concentration of 1.0 ug/mL. In yet a further embodiment of any of the foregoing embodiments, wherein the cells are exposed or incubated with the photosensitizer for 1 h to 48 h. In yet a further embodiment of any of the foregoing embodiments, wherein the cells are exposed to or incubated with the photosensitizer for 24 h at 37° C. In yet a further embodiment of any of the foregoing embodiments, wherein the photosensitizer is a porphyrin, chlorin or a dye. In yet a further embodiment of any of the foregoing embodiments, wherein the photosensitizer is selected from $AlPcS_{2A}$, $AlPcS_4$, lutrin, 5-aminolevulinic acid (ALA), hypericin, silicon phthalocyanine zinc (II) phthalocyanine (ZnPc), silicon phthalocyanine, mono-L-aspartyl chlorin e6, benzoporphyrin derivative monoacid ring A, chlorin photosensitizer tin etiopurpurin, tetra(m-hydroxyphenyl)chlorin, lutetium texaphyrin, 9-acetoxy-2,7,12,17-tetrakis-(β-methoxyethyl)-porphycene, naphthalocyanines, Allumera®, Photofrin®, Visudyne®, Levulan®, Foscan®, Fospeg®, Metvix®, Hexvix®, Cysview® and Laserphyrin®, Antrin®, Photochlor®, Photosens®, Photrex®, Lumacan®, Cevira®, Visonac®, BF-200 ALA®, Amphinex® and Azadipyrromethenes. In yet a further embodiment of any of the foregoing embodiments, wherein the photosensitizer is AlPcS$_{2,4}$. In yet a further embodiment of any of the foregoing embodiments, wherein the cells are washed with a buffered balanced salt solution one or more times, and taken up in the buffered balanced salt solution prior to exposure to light. In yet a further embodiment of any of the foregoing embodiments, wherein the buffered balanced salt solution selected from the group consisting of phosphate-buffered saline (PBS), Dulbecco's Phosphate-buffered saline (DPBS), Earle's Balanced Salt solution (EBSS), Hank's Balanced Salt Solution (HBSS), TRIS-buffered saline (TBS), and Ringer's balanced salt solution (RBSS). In yet a further embodiment of any of the foregoing embodiments, wherein the cells are taken up in 1× to 10× concentration/dilution of the buffered balanced salt solution prior to light exposure. In yet a further embodiment of any of the foregoing embodiments, wherein the cells are taken up in 1×DPBS prior to light exposure. In yet a further embodiment of any of the foregoing embodiments, wherein the cells are exposed to light for 1 min to 60 min. In yet a further embodiment of any of the foregoing embodiments, wherein the cells are exposed to light generated by a laser. In yet a further embodiment of any of the foregoing embodiments, wherein the cells are exposed to light having a wavelength from 600 nm to 850 nm that is generated by a laser. In yet a further embodiment of any of the foregoing embodiments, wherein the EB producing cells are incubated with or exposed to 1 ug/mL of AlPcS$_{2,4}$ for 24 h at 37° C., washed multiple times in 1×DPBS, taken up in 1×DPBS, and then exposed to light generated from a 670 nm laser for 1 min to 10 min. In yet a further embodiment of any of the foregoing embodiments, wherein the method further comprises the step of: purifying/isolating the ICVs or antigenic ICVs by using sucrose gradients. In yet a further embodiment of any of the foregoing embodiments, wherein the method further comprises the step of: purifying/isolating the ICVs or the antigenic ICVs by: (i) removing cellular debris by centrifugation from 1,000 rpm to 2,500 rpm for 1 to 10 minutes; and (ii) recovering the ICVs or antigenic ICVs by centrifugation using 10,000×g to 20,000×g for 5 to 15 minutes; optionally, concentrating the recovered nanometer sized ICVs or antigenic nanometer sized ICVs by using concentrators with a pore size cut-off from 50 to 150 kDA. In yet a further embodiment of any of the foregoing embodiments, wherein the isolated ICVs or isolated antigenic ICVs have average diameters from 10 nm to 10,000 nm. In yet a further embodiment of any of the foregoing embodiments, wherein the isolated ICVs or isolated antigenic ICVs have average diameters from 150 nm to 5,000 nm. In yet a further embodiment of any of the foregoing embodiments, wherein the isolated ICVs or isolated antigenic ICVs have average diameters from 1000 nm to 5,000 nm. In yet a further embodiment of any of the foregoing embodiments, wherein the isolated ICVs or isolated antigenic ICVs comprise a cargo selected from biological molecules, therapeutic agents, prodrugs, gene silencing agents, chemotherapeutics, diagnostic agents, components of a gene therapy system and/or components of a gene editing system. In yet a further embodiment of any of the foregoing embodiments, wherein the isolated ICVs or isolated antigenic ICVs are loaded with the cargo by direct membrane penetration, chemical labeling and conjugation, electrostatic coating, adsorption, absorption, sonification, electroporation, use of pH gradients, or any combination thereof. In yet a further embodiment of any of the foregoing embodiments, wherein the isolated ICVs or isolated antigenic ICVs are loaded with the cargo by incubating isolated ICVs or isolated antigenic ICVs, or the cells used to produce ICVs or antigenic ICVs, with a cargo for a sufficient period of time to allow uptake or adsorption of the cargo by the ICVs, antigenic ICVs or by the cells. In yet a further embodiment of any of the foregoing embodiments, wherein the cells comprise or have been modified to comprise one or more functional moieties on the cell surface. In yet a further embodiment of any of the foregoing embodiments, wherein the one or more functional moieties are one or more targeting ligands. In yet a further embodiment of any of the foregoing embodiments, wherein the one or more targeting ligands direct the ICVs or antigenic ICVs to a certain cell, cell type, tissue type, tumor, or organ. In yet a further embodiment of any of the foregoing embodiments, wherein the one or more targeting ligands are an antibody or a single-chain variable fragment which binds to a tumor-specific antigen. In yet a further embodiment of any of the foregoing embodiments, wherein the tumor-specific antigen is selected from alphafetoprotein (AFP), carcinoembryonic antigen (CEA), CA-125, CA15-3, CA19-9, MUC-1, epithelial tumor antigen (ETA), tyrosinase, melanoma-associated antigen (MAGE), abnormal products of ras or p53, CTAG1B, MAGEA1, and HER2/neu. In yet a further embodiment of any of the foregoing embodiments, wherein the cells have been bioorthogonally-conjugated to comprise one or more functional moieties. In yet a further embodiment of any of the foregoing embodiments, wherein the one or more functional moieties have been added to the surface of the cells by bioorthogonally-engineering, comprising: (1) treating sialic acid residues on the surface of the cells with an oxidizing agent to form aldehyde groups; then either step (2)(a) and (b), or step (3)(a) and (3)(b): (2)(a) ligating, linking or conjugating aminooxy-functionalized molecules to the surface of the cells by forming oxime bonds with the aldehyde groups; and (2)(b) inducing production of bioorthogonally-conjugated ICVs or bioorthogonally-conjugated antigenic ICVs by exposing or contacting the cells with the cell blebbing buffer which comprises a sulfhydryl blocking agent or a photosensitizer; or (3)(a) inducing production of ICVs or antigenic ICVs from the cells by exposing or contacting the cells with the cell blebbing buffer which comprises a sulfhydryl blocking agent or a photosensitizer; and (3)(b) producing bioorthogonally-conjugated ICVs or bioorthogonally-conjugated antigenic ICVs by ligating, linking or conjugating aminooxy-functionalized molecules to the surface of the ICVs by forming oxime bonds with the aldehyde groups. In yet a further embodiment of any of the foregoing embodiments, wherein the oxidizing agent is either sodium periodate or lead tetraacetate. In yet a further embodiment of any of the foregoing embodiments, wherein the cells are treated with 1 mM sodium periodate for 30 min at 4° C. In yet a further embodiment of any of the foregoing embodiments, wherein the aminooxy-functionalized molecules comprise a detecting agent, and/or cell-, tumor-, or tissue-targeting ligands. In yet a further embodiment of any of the foregoing embodiments, wherein the detecting agent is an enhanced fluorophore-based dye. In yet a further embodiment of any of the foregoing embodiments, wherein the aminooxy-functionalized molecules are ligated, linked or conjugated to the aldehyde groups in the presence of a catalyst. In yet a further embodiment of any of the foregoing embodiments, wherein the catalyst is p-anisidine. In yet a further embodiment of any of the foregoing embodiments, wherein the aminooxy-functionalized molecules are ligated, linked or conjugated to the aldehyde groups in the presence of 10 mM p-anisidine for 90 min at 4° C. In a particular embodiment, the disclosure also provides for bioorthogonally-conjugated ICVs produced by any of the foregoing embodiments. In yet a further embodiment of any of the foregoing embodiments, wherein the bioorthogonally-conjugated ICVs comprise oxime-linked detecting agents. In yet a further embodiment of any of the foregoing embodiments, wherein the bioorthogonally-conjugated ICVs are loaded with one or more small molecule therapeutic compounds or agents. In a particular embodiment, the disclosure also provides for isolated antigenic ICVs produced by any of the foregoing embodiments. In yet a further embodiment of any of the foregoing embodiments, wherein the antigenic ICVs are loaded with one or more small molecule therapeutic compounds or agents. In a particular embodiment, the disclosure also provides for isolated ICVs produced by any of the foregoing embodiments. In a certain embodiment, the disclosure also provides for a pharmaceutical composition comprising the bioorthogonally-conjugated antigenic ICVs produced by any of the foregoing embodiments, the isolated antigenic ICVs produced by any of the foregoing embodiments, or the isolated ICVs produced by any of the foregoing embodiments; and a pharmaceutically acceptable carrier, excipient, and/or diluent. In another embodiment, the disclosure provides a method of stimulating an immune response to a cancer in a subject in need thereof, comprising: administering the pharmaceutical composition disclosed in any of the foregoing embodiments. In yet a further embodiment of any of the foregoing embodiments, wherein the cancer is selected from squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulvar cancer, thyroid cancer, hepatic carcinoma, leukemia and other lymphoproliferative disorders, and various types of head and neck cancers. In yet a further embodiment of any of the foregoing embodiments, wherein the pharmaceutical composition is administered by intravenous administration, intertumoral administration, intraperitoneal administration, intramuscular administration, intracoronary administration, intraarterial administration, subcutaneous administration, transdermal delivery, intratracheal administration, subcutaneous administration, intraarticular administration, intraventricular administration, inhalation, or intracerebral administration. In yet a further embodiment of any of the foregoing embodiments, wherein the pharmaceutical composition is administered to the subject concurrently or sequentially with one or more anticancer agents or chemotherapeutics. In another embodiment, the disclosure provides a method of treating a disease or disorder in a subject in need thereof, comprising: administering the pharmaceutical composition disclosed in any of the foregoing embodiments. In another embodiment, the disclosure provides a method of stimulating an immune response to a cancer in a subject in need thereof, comprising: (a) obtaining antigen presenting cells; (b) pulsing the antigen presenting cells with an antigen associated with cancer cells; (c) inducing cell membrane blebbing by use of a sulfhydryl blocking agent; (d) collecting antigenic micrometer sized ICVs (mICVs) induced by cell membrane blebbing; and (e) administering said antigenic mICVs to the subject in need of immunotherapy. In yet a further embodiment of any of the foregoing embodiments, wherein the cancer is selected from squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, valvar cancer, thyroid cancer, hepatic carcinoma, leukemia and other lymphoproliferative disorders, and various types of head and neck cancers. In yet a further embodiment of any of the foregoing embodiments, wherein the antigen presenting cells are dendritic cells, macrophages, monocytes, Langerhans cells, B cells, genetically modified cells, and mesenchymal stem cells. In yet a further embodiment of any of the foregoing embodiments, wherein the antigen presenting cells are immature dendritic cells that are pulsed with an antigen to produce semimature or mature dendritic cells. In yet a further embodiment of any of the foregoing embodiments, where the immature dendritic cells are derived from bone marrow of a human subject. In yet a further embodiment of any of the foregoing embodiments, wherein the antigen presenting cells are obtained from the subject to be treated by immunotherapy. In yet a further embodiment of any of the foregoing embodiments, wherein the sulfhydryl blocking agent is paraformaldehyde. In yet a further embodiment of any of the foregoing embodiments, wherein the antigenic mICVs have diameters from 1 micrometer to 5 micrometers. In yet a further embodiment of any of the foregoing embodiments, wherein the antigenic mICVs are administered by intravenous administration, intertumoral administration, intraperitoneal administration, intramuscular administration, intracoronary administration, intraarterial administration, subcutaneous administration, transdermal delivery, intratracheal administration, subcutaneous administration, intraarticular administration, intraventricular administration, inhalation, or intracerebral administration. In yet a further embodiment of any of the foregoing embodiments, wherein the antigenic mICVs are administered concurrently or sequentially with one or more anticancer agents or chemotherapeutics. A cell-free cell therapy comprising the pharmaceutical composition disclosed in any of the foregoing embodiments for treating a subject having a disease or disorder. In yet a further embodiment of any of the foregoing embodiments, wherein the subject has cancer. A vaccine comprising the pharmaceutical composition disclosed in any of the foregoing embodiments for prevention of an infection in a subject by an infectious agent. In yet a further embodiment of any of the foregoing embodiments, wherein the infectious agent is a bacterium, a virus, a fungus, or a protozoon. A therapeutic vaccine comprising the pharmaceutical composition disclosed in any of the foregoing embodiments for use in treating a subject having cancer.

DESCRIPTION OF DRAWINGS

FIG. 38 provides quantitative results using AAV stock and AAV produced cell derived AAV treated with NEM. Stock AAV transduction was greatly affected by NEM, reducing the transduction efficiency after just 10 minutes, and leading to almost no transduction after incubation for 2 hours. However, AAV isolate from lysate showed that the cells had a protective effect. There was only a minimal drop in transduction until they had been exposed to NM for 4 hours, and the 8 hours timepoint only showed about half the transduction that the 0-minute timepoint showed. This demonstrated that any AAV that is free during the vesiculation process should be neutralized by the presence of NEM. It also demonstrates that cell membrane protects AAVs from NEM, and this should translate to the ICVs. Lastly, after seeing minimal DNA damage in the previous experiment, it is clear that the NEM affects protein, affecting the transduction efficiency of the AAVs.

FIG. 39 shows whether NEM inactivates stock AAV or AAV from producer cells using the time points of 0 min, 10 min, 30 min and 1 h. NEM was used at a dose of 5E09 GCs/mL. As shown, stock AAV transduction was greatly affected by NEM, reducing the transduction efficiency after just 10 minutes, while AAV from producer cells was not similarly affected.

FIG. 40 shows whether NEM inactivates stock AAV or AAV from producer cells using the time points of 2 h, 4 h, 6 h and 8 h. NEM was used at a dose of 5E09 GCs/mL. As shown, stock AAV transduction efficiency was greatly affected by NEM at all tested time points, while AAV from producer cells only showed a minimal drop in transduction efficiency until the lysate AAVs had been exposed to NEM for 4 hours, and the 8-hour timepoint only showed about half the transduction efficiency that the 0-minute timepoint showed.

FIG. 41A-B shows the results of flow cytometry studies looking at whether (A) free AAV and AAV cells; and (B) photoinduced AAV containing ICVs were resistant to anti-AAV antibodies. Free AAVs were silenced by the neutralizing antibodies. Light induced cell vesicles were also silenced at a similar amount. This system appeared not to be protective from nAbs.

FIG. 42A-B shows the results of flow cytometry studies looking at whether (A) free AAV or (B) 5 min photoinduced AAV containing ICVs were resistant to anti-AAV antibodies. NEM induced micrometer sized cell vesicles showed far greater transduction efficiency and were able to resist neutralization by neutralizing antibodies for AAV. The nano-sized ICVs appeared to resist neutralization but showed insignificant transduction. Photo-induced cell vesicles showed a similar profile to the NEM induced cell vesicles, except the micro ICVs did show a response to the neutralizing antibody based on the concentration. However, they resisted being completely neutralized. This is due to the protective effect of the membrane around AAV containing ICVs that protected AAVs from neutralization.

FIG. 43 provides fluorescent images looking at whether micrometer sized AAV containing ICVs can protect from neutralizing antibodies. As shown, micrometer sized AAV containing ICVs were protected against neutralization by anti-AAV antibodies.

FIG. 47A-C presents a bioorthogonally tethered retrovirus. (A) Production of functionalized retrovirus by bioorthogonally modifying the surface of virus producer cells whose sialylated glycoproteins (green) on the phospholipid cell membrane (purple) are oxidized to generate aldehyde groups. Aminooxy-functionalized molecules (yellow) are conjugated with aldehyde groups via oxime linkages. (B) Magnet-directed transduction of magnetically labeled retroviral particles that were produced from bioorthogonally engineered surface of 293GPG/EGFP retroviral producer cells. After one week of incubation with G418, selected cells were stained with 0.1% methylene blue in methanol for visualization. (C) Synthetically engineered retroviral particles for targeted transduction of folic acid receptor (FAR)-overexpressing cancer cells. The surface of 293GPG/EGFP retrovirus producing cells was bioorthogonally engineered as described in (A) using the aminooxy-activated ketal-PEG-FA molecules. The resulting FAR-targeting retroviral particles were incubated with FAR-overexpressing HeLa human cervical cancer cells and FAR-negative NIH 3T3 cells for 2 h. After 24 h of incubation, transduction efficiency was quantified by EGFP expressing cells by flow cytometry.

FIG. 48A-B presents fluorescently labeled HeLa cells and HeLa cell-derived mICVs produced by sulfhydryl blocking, using biorthogonal conjugation of CF 488 on the cell surface. (A) Producer cells were treated with paraformaldehyde to induce cell vesicles, and (B) isolated mICVs were imaged using a confocal laser scanning microscope. Scale bar=10 μm.

Cells were imaged by bright field microscope (A), then nano and micro-scale ICVs were isolated as previously described and analyzed by DLS or light microscope (B), respectively. The sized of the ICVs were determined by using ImageJ analysis. BMDC and ICVs were labeled with fluorescent anti-CD11c and compared for CD11c presentation (marker of dendritic cells) by flow cytometry. As shown, BMDCs, when exposed to PFA blebbing buffer, induced cell vesicle formation (A). (B) Both immature and mature dendritic cells produced similar sized micro and nano-scale ICVs. (C) BMDCs and ICVs exhibit similar presentation levels of CD11c, a dendritic cell marker.

Figure 56:
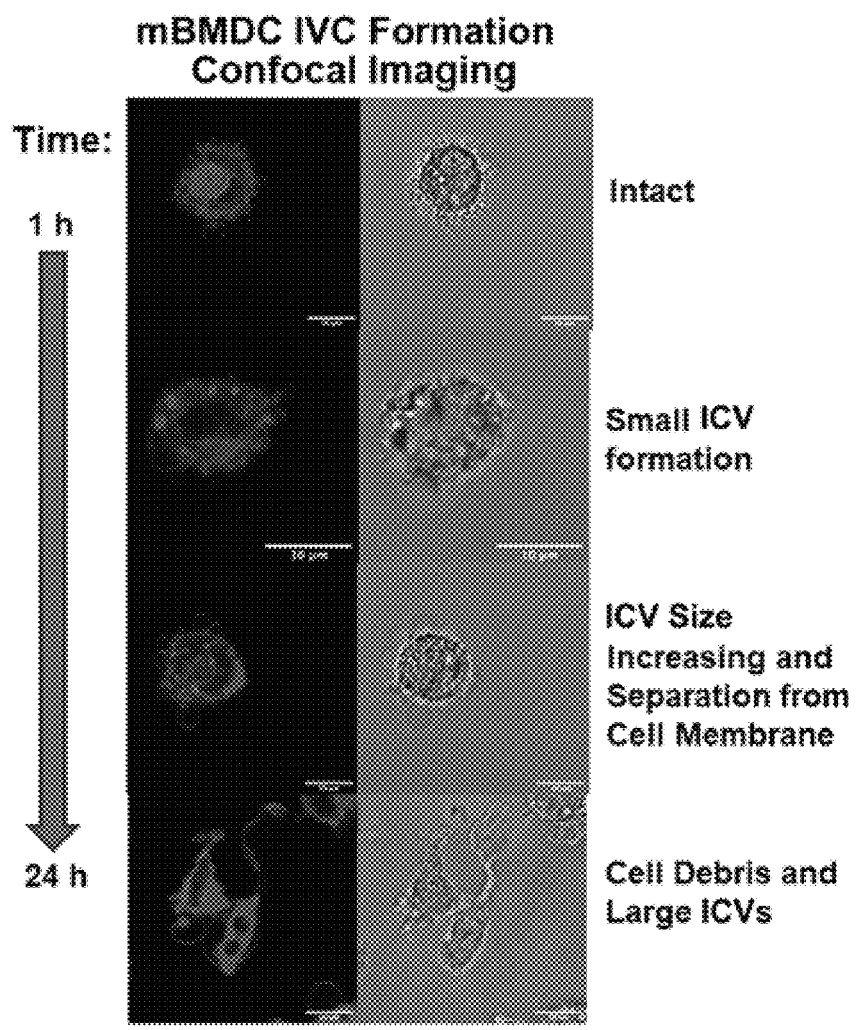

FIG. 56 provides confocal images over time of mature BMDC blebbing. Bone marrow was isolated from C57BL/6 mice and differentiated into BMDCs and matured as previously described. Mature BMDCs were stained with PKH26 (red membrane stain) and DAPI (blue nuclear stain) and exposed to PFA blebbing buffer. Cells and induced cell vesicle production were observed over time by confocal microscope imaging. Mature BMDCs produced larger ICVs over time, with complete use of cell membrane accomplished at 24 hours post-incubation.

FIG. 57 provides confocal images over time of immature BMDC blebbing. Bone marrow was isolated from C57BL/6 mice and differentiated into BMDCs as previously described. Immature BMDCs were stained with PKH26 (red membrane stain) and DAPI (blue nuclear stain) and exposed to PFA blebbing buffer. Cells and induced cell vesicle production dynamics were observed over time by confocal microscope imaging. Similar to mature BMDCs, immature BMDCs produced larger ICVs over time, with complete use of cell membrane accomplished at 24 hours post-incubation.

FIG. 58A-C shows how the length of treatment of BMDCs with the blebbing methods disclosed herein influences ICV size. (A) Immature BMDCs or (B) mature BMDCs were treated in 25 mM PFA blebbing buffer for 1, 6, 12, or 24 hours. (A, B) Nano- and (C) micro-scale ICVs were isolated as previously described and analyzed by DLS or light microscope imaging, respectively. To understand how ICV size was influenced by the time length of the blebbing treatment, immature or mature BMDCs were treated in 25 mM PFA blebbing buffer for 1, 6, 12, or 24 hours. (A-C) Both micro and nano ICVs showed similar size distributions over time. This indicated that larger ICVs created over time, as demonstrated by confocal microscopy data, are likely removed during cells and debris removal steps.

FIG. 59A-C examines which blebbing method, paraformaldehyde (PFA) or paraformaldehyde+DTT, provides for ICVs having the best antigen presentation and T cell activation. (A, B) Mature BMDC ICVs were labeled with anti-SIINFEKL and analyzed by flow cytometry for antigen presentation. (C) Mature BMDC ICVs were tested for T cell activation by CPRG assay as previously described. (A, B) PFA and PFA/DTT ICVs showed similar levels of antigen presentation. While antigen presentation levels were similar, (C) PFA ICVs were capable of stimulating T cells by nearly 2-fold. This indicated that PFA was the preferred method for inducing cell vesicles from BMDs, as functionality of the ICVs were improved.

FIG. 60A-B demonstrates that ICVs from BMDCs exhibit similar CD40 surface markers as parent dendritic cells. Immature BMDCs were matured in LPS for 0, 6, and 12 hours to generate BMDCs at different stages of maturation. BMDCs from these time points were treated with 25 mM PFA blebbing buffers and micro ICVs were isolated as previously described. BMDCs from the varying time points and ICVs subsequently produced were labeled with fluorescent anti-CD40 (BMDC maturation marker) and analyzed by flow cytometry. BMDCs and ICVs from varying maturation states showed similar levels of (A) % CD40(+) maturation marker and (B) mean CD40(+) marker presentation as BMDC cells. This indicates that ICVs can have controlled levels of maturation, similar to their parent cells. However, unlike cells, ICVs cannot continue to undergo changes, locking their stage of maturation into place. This is important for controlling immune response in vivo.

FIG. 61 provides images of the CD40 expression on mBMDC-derived antigenic mICVs. BMDCs were cultured in RPMI supplemented 10% FBS and 20 ng/mL rmGM-CSF. On day 7 of culture, cells were incubated with 20 ng/mL lipopolysaccharide for 12 h to induce maturation. Cells were collected by centrifugation and plated in either DMEM without FBS (for exosome production) or DPBS with paraformaldehyde as described herein. After 12 h, the plates were washed and incubated with 10% anti-mouse CD11c antibody (Alexa Flour 488). The plates were then washed with DPBS and imaged.

FIG. 62A-D demonstrates that ICVs exhibit similar CD80 and CD86 surface markers as parent dendritic cells. Immature BMDCs were matured in LPS for 0, 6, and 12 hours to generate BMDCs at different stages of maturation. BMDCs from these time points were treated with 25 mM PFA blebbing buffers and micro ICVs were isolated as previously described. BMDCs from the varying time points and ICVs subsequently produced were labeled with fluorescent (A, B) anti-CD80 or (C, D) anti-CD86 (BMDC costimulatory molecules) and analyzed by flow cytometry. Similar to CD40 presentation, ICVs produced from cells of varying stages of maturation presented increased levels of (A) % CD80(+) markers and (B) mean CD80(+) markers, as well as, (C) % CD86(+) markers and (D) mean CD86(+) markers, which mirrored those of the parent cells. This indicated that ICVs likely mirror many of the parent cell presentation qualities, with the unique feature that ICV presentation is locked and cannot undergo further changes.

FIG. 63A-B demonstrates that ICVs exhibit similar antigen presentation to parent dendritic cells but are more stable. Immature BMDCs were matured in LPS for 0, 6, and 12 hours to generate BMDCs at different stages of maturation. BMDCs from these time points were treated with 25 mM PFA blebbing buffers and micro ICVs were isolated as previously described. BMDCs from the varying time points and ICVs subsequently produced were labeled with fluorescent SIINFEKL (antigen) and analyzed by flow cytometry. (A) and (B) Similar to CD40, CD80, and CD86 presentation findings, BMDCs and ICVs from varying maturation states displayed similar levels of antigen presentation.

FIG. 64A-B provides graphs looking at the expression of MHC1 from immature and mature BMDC. Immature and mature BMDCs were labeled with fluorescent anti-MHCI and compared for (A) % MHC1(+) cells, and (B) Mean MHC1(+) presentation by flow cytometry. In the literature, MHCI presentation has been reported as similar between immature and mature dendritic cell groups. Flow cytometry data indicated that while percentages of MHCI positive cells were similar, density of MHCI on mature cells was increased by nearly 2-fold. This indicated that mature BMDCs are superior at antigen presentation.

FIG. 65 provides images of a 12% agarose gel where mature MBDC and ICVs from mature BMDCs were lysed (lane 2 and lane 4, respectively) and run out on the gels for 100 V for 60 min. Mature BMDCs and ICVs display similar RNA profiles, with DNA from cells displaying at the top of the lane.

FIG. 66 provides images of a 12% agarose gel where ICVs from immature BMDCs or ICVs from mature BMDCs were lysed (lane 2 and lane 4, respectively), or ICVs from immature BMDCs or ICVs from mature BMDCs were lysed and further treated with RNase (lane 3 and lane 5, respectively) and run out on the gels for 100 V for 60 min. The ICVs showed similar RNA profiles irrespective of the maturation state of the DCs.

Figure 67:
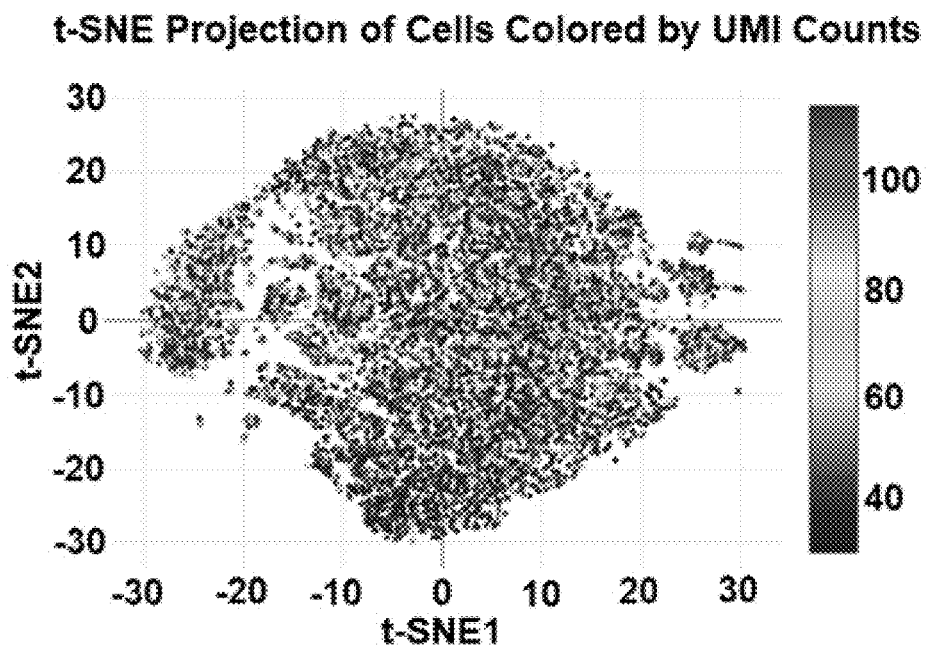

FIG. 67 provides "unsupervised" clustering analysis of single-cell RNA sequence analysis of particles having similarities in RNA content. 15 distinct clusters were indicated.

Figure 68:
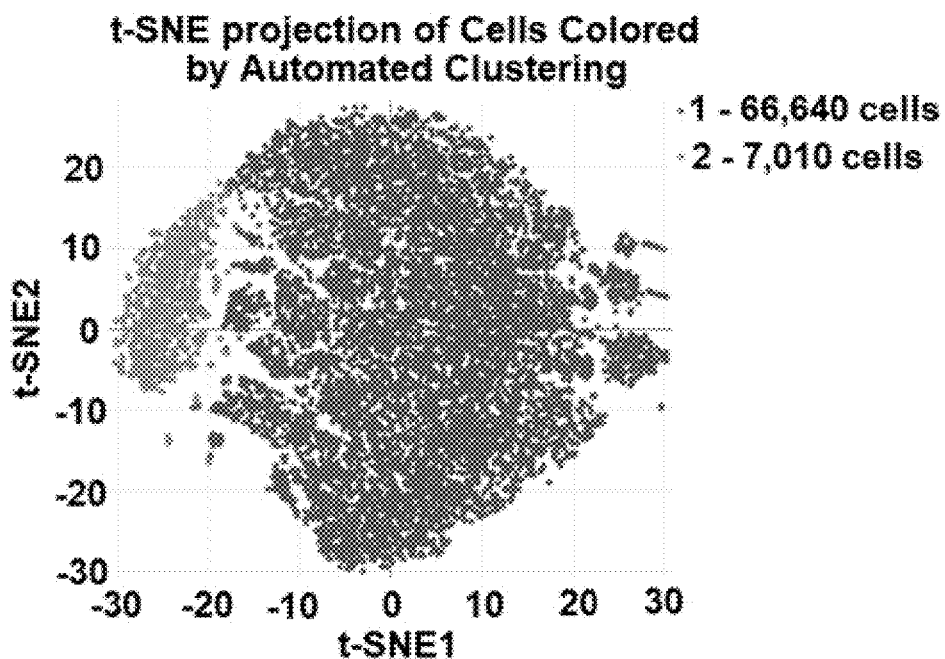

FIG. 68 provides a refined clustering analysis of single-cell RNA sequence analysis of particles having similarities in RNA content. Two main clusters of particles having similarities in RNA content were found. These RNAs were identified (see FIG. 66) and are known to be upregulated in immune cells during maturation/activation.

FIG. 69 provides a heat map matrix of BMDC ICV single cell sequence data. As indicated, genes of interest include GM42418, Fth1, AY036118, Saa3, Mt-Co2, Mt-Co1, Mt-Co3, Rpl19, Vezt, Snap91, Ctbs, Mon2, Hiflan, Nbas, Rock2, Rap1b, Tmed7, and Fbll1.

FIG. 70A-B provides the results of PKH dosing and T-Cell stimulation on mature and immature BMDCs, and ICVs produced from mature and immature BMDCs. (A) Comparing equivalent numbers of immature or mature BMDCs, mature BMDCs had nearly 3-fold greater surface area based on PKH membrane signal. (B) Mature BMDCs produced 3-fold the amount of ICVs. It is therefore likely that amount of ICVs produced is correlated with surface area of membrane.

FIG. 71 shows that ICVs produced from mature BMDCs have increased antigen presentation and stimulation ability than ICVs produced from immature BMDCs. A similar antigen presentation trend was seen with mature BMDCs and immature BDCs. Based on dosing by equivalent surface area, T cell stimulation showed the following trend: ICVs from mature BMDCs>mature BMDCs>immature BMDCs and ICVs from immature BMDCs. When dosing is based on surface area, there are more ICVs:T cells than BMDCs:T cells, generating greater likelihood of interactions and stimulation.

FIG. 72 presents images from Day 30 of the tumor challenge with mice by vaccine category. PBS, OVA, and SIINFEKL groups all rapidly developed tumors. Immature and mature BMDC vaccine groups developed small tumors by day 15 and went into complete remission. ICVs from immature BMDCs developed tumors at a slowed rate, indicating a low immune response, but not potent enough to prevent tumor growth. ICVs from mature BMDCs developed small tumors, larger than those of the cell vaccine group, and later went into total remission. This data suggests that immature BMDCs likely matured after administration in order to achieve a similar response to the mature BMDC group. This demonstrates the need for a cell-free vaccine, as cell maturation and state could not be accurately controlled, leading to unpredictability of the elicited the immune response. However, ICVs from immature BMDCs had a tolerant effect while ICVs from mature BMDCs performed similarly to mature BMDCs. This indicated that the controlled maturation state of the ICVs provided for a controllable immune response, imperative for a safe cancer vaccine.

FIG. 73A-B provides graphs that go with the images presented on FIG. 70. (A) ICVs from mature BMDCs had a similar anti-tumor effect as mature BMDC vaccine group. By contrast, PBS, OVA, and SIINFEKL groups all rapidly developed tumors. (B) All mice treated with mICV or BMDC were alive at day 50 of the tumor challenge. By contrast, all of the PBS, OVA, and SIINFEKL treated mice had died prior to day 35 of the tumor challenge.

DETAILED DESCRIPTION

As used herein and in the appended claims, the singular forms "a," "an," and "the" include plural referents unless the context clearly dictates otherwise. Thus, for example, reference to "a cell vesicle" includes a plurality of such vesicles and reference to "the sulfhydryl blocking agent" includes reference to one or more sulfhydryl blocking agents and equivalents thereof known to those skilled in the art, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although many methods and reagents are similar or equivalent to those described herein, the exemplary methods and materials are disclosed herein.

All publications mentioned herein are incorporated herein by reference in full for the purpose of describing and disclosing the methodologies, which might be used in connection with the description herein. Moreover, with respect to any term that is presented in one or more publications that is similar to, or identical with, a term that has been expressly defined in this disclosure, the definition of the term as expressly provided in this disclosure will control in all respects.

It should be understood that this disclosure is not limited to the particular methodology, protocols, and reagents, etc., described herein and as such may vary. The terminology used herein is for the purpose of describing particular embodiments only and is not intended to limit the scope of the present disclosure.

Other than in the operating examples, or where otherwise indicated, all numbers expressing quantities of ingredients or reaction conditions used herein should be understood as modified in all instances by the term "about." The term "about" when used to described the present invention, in connection with percentages means±1%.

Figure 1:
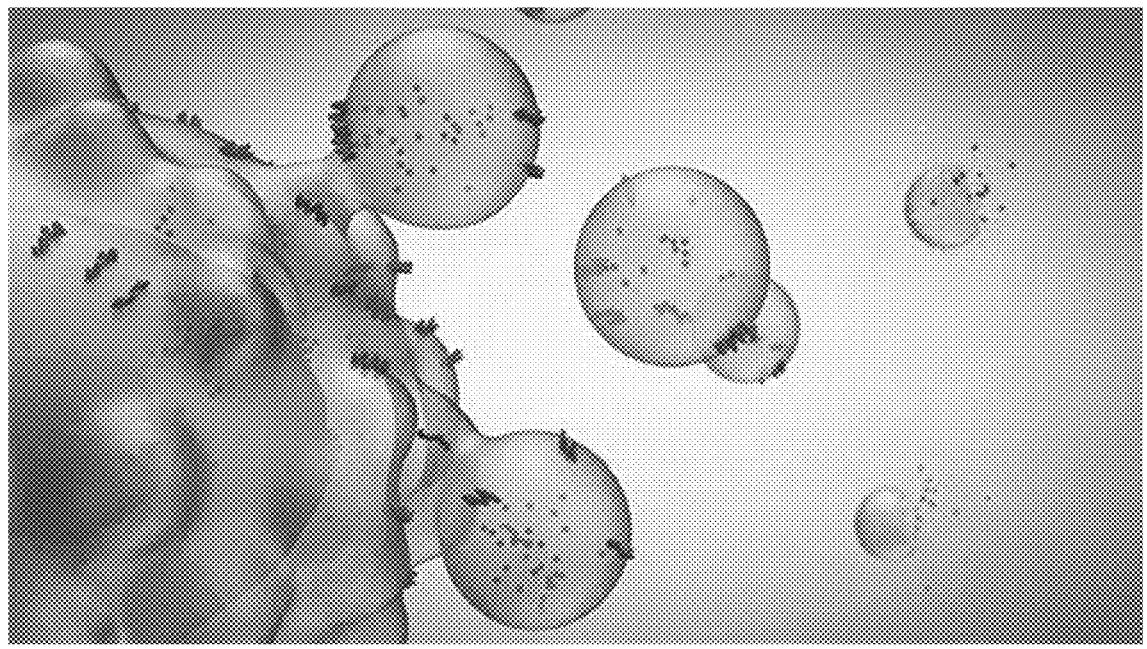
FIG. 1 provides a diagram of the blebbing process induced by the chemical agents disclosed herein that can be used to induce cell vesicle formation, and the use of the induced cell vesicles for various applications, including cell-free based cell therapies.
Figure 2:
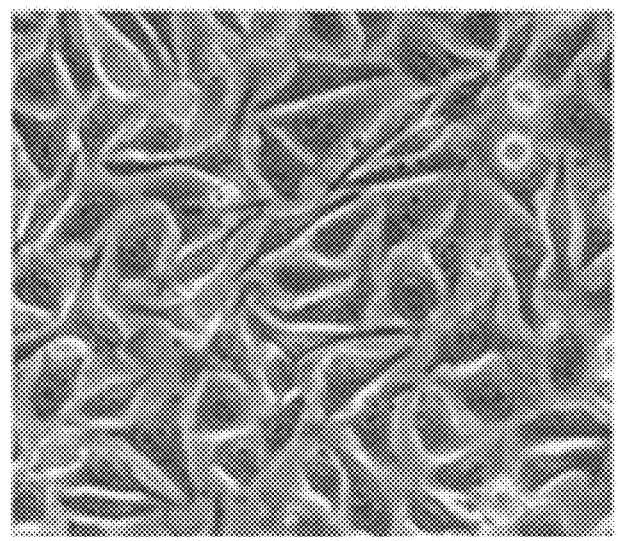
FIG. 2 presents a photo of HeLa cells prior to treatment with N-ethylmaleimide.
Figure 3:
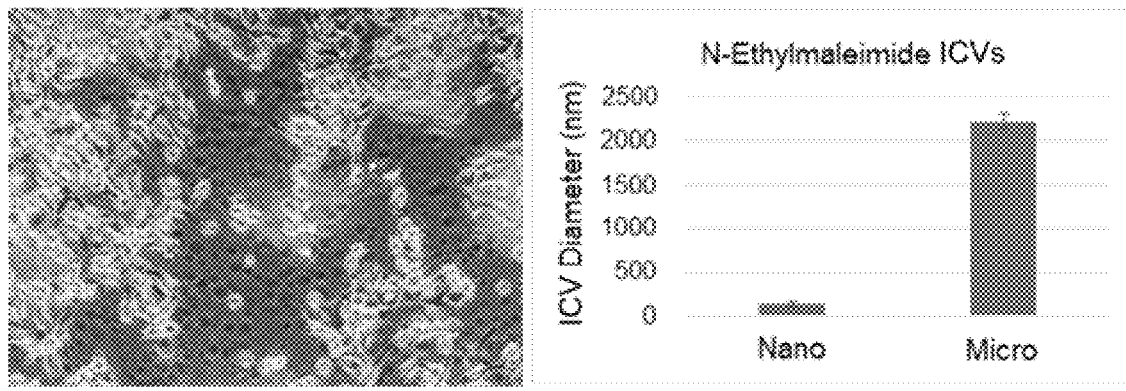
FIG. 3 demonstrates that nanometer sized or micrometer sized ICVs that are induced from HeLa cells after treatment with N-ethylmaleimide. (Top Image) Micro scale ICVs are visible in the images as circular vesicles with a darker contrast compared with the cells. (Bottom Image) More micrometer sized ICVs are produced than nanometer sized ICVs post treatment of HeLa cells with N-ethylmaleimide.

The term "induced cell vesicle" or "ICV" as used herein refers to cell vesicles that have been induced to form from cells when the cells have been treated using the cell blebbing methods of the disclosure (e.g., see FIG. 1). Thus, an "ICV" is distinguishable from a "bleb" or "a cellular bleb" as the later terms refers to a bulge or protrusion of the plasma membrane of a cell, and from "extracellular vesicles" in that the production of ICVs are a direct result of using the cell blebbing methods of the disclosure, as opposed to naturally occurring production of extracellular vesicles from the cells. Moreover, the term "induced cell vesicle" or "ICV" refers to all forms of induced cell vesicles or ICVs disclosed herein, unless stated otherwise. Thus, the term "induced cell vesicle" or "ICV" includes antigenic induced cell vesicles, bioorthogonally engineered induced cell vesicles, AAV containing induced cell vesicles, etc.

The term "antigenic induced cell vesicle" or "antigenic ICV" as used herein, refers to an induced cell vesicle disclosed herein that comprises or has been modified to comprise an antigen on the induced cell vesicle surface which can be used to stimulate an immune response in a subject. Typically, an "antigenic induced cell vesicle" or "antigenic ICV" is produced from antigen presenting cells, like dendritic cells. Accordingly, an "antigenic induced cell vesicle" of the disclosure is ideally suited for cell-free immunotherapy and cell-free cancer vaccine applications.

The term "extracellular vesicle" as used herein, refers to any membrane-derived vesicle that is secreted by a cell. Extracellular vesicles can include a range of extracellular vesicles, including exosomes, microparticles and microvesicles, which are secreted by many cell types under both normal physiological and pathological conditions. An "extracellular vesicle" is distinguishable from an "induced cell vesicle", in that an "induced cell vesicle" directly results from using the cell blebbing methods disclosed herein, i.e., an "induced cell vesicle" does not naturally form from a cell using a naturally occurring process, unless the cells is treated with the cell blebbing methods disclosed herein.

In a particular embodiment, the method and compositions described herein comprise induced cell vesicles that have an average diameter of 10 nm, 20 nm, 30 nm, 40 nm, 50 nm, 60 nm, 70 nm, 80 nm, 90 nm, 100 nm, 110 nm, 120 nm, 130 nm, 140 nm, 150 nm, 160 nm, 170 nm, 180 nm, 190 nm, 200 nm, 250 nm, 300 nm, 350 nm, 400 nm, 450 nm, 500 nm, 550 nm, 600 nm, 650 nm, 700 nm, 750 nm, 800 nm, 850 nm, 900 nm, 950 nm, 1000 nm, 1100 nm, 1200 nm, 1300 nm, 1400 nm, 1500 nm, 1600 nm, 1700 nm, 1800 nm, 1900 nm, 2000 nm, 2500 nm, 3000 nm, 3500 nm, 4000 nm, 5000 nm, 6000 nm, 7000 nm, 8000 nm, 9000 nm, 10,000 nm or any range that includes or is between any two of the foregoing values, including fractional increments thereof. In another embodiment, the methods disclosed herein afford micrometer sized induced cell vesicles (i.e., induced cell vesicles having a diameter greater than 1000 nm). In yet another embodiment, the methods disclosed herein afford both nanometer sized and micrometer sized induced cell vesicles (i.e., induced cell vesicles having a diameter from 1 nm to greater than 1 μm). In a certain embodiment, the methods disclosed herein provide for isolation of induced cell vesicles having average diameters from 20 nm to 200 nm. In an alternate embodiment, the methods disclosed herein provide for the isolation of induced cell vesicles having average diameters from 20 nm to 500 nm. In another alternate embodiment, the methods disclosed herein provide for the isolation of induced cell vesicles having average diameters from about 500 nm to about 1000 nm. In yet another alternate embodiment, the methods disclosed herein provide for isolation of induced cell vesicles having average diameters from about 1000 nm to about 10000 nm.

The terms "micrometer sized induced cell vesicle", or "mICV" as used herein, all refer to induced cell vesicles having a dimeter in the micrometer size range. In a particular embodiment, the mICV has a diameter of 1 μm, 2 μm, 3 μm, 4 μm, 5 μm, 6 μm, 7 μm, 8 μm, 9 μm, 10 μm, or a range that includes or is between any two of the foregoing values, including fractional increments thereof.

The terms "blebbing", "plasma membrane blebbing" or "cell membrane blebbing" as used herein, all refer to cellular biological process that results from use of the methods disclosed herein which induce plasma membrane blebbing in cells. Typically, blebbing of the plasma membrane is a morphological feature of cells undergoing late stage apoptosis. A bleb is an irregular bulge in the plasma membrane of a cell caused by localized decoupling of the cytoskeleton from the plasma membrane. The bulge eventually separates from the parent plasma membrane taking part of the cytoplasm with it to form an extracellular vesicle. Blebbing is also involved in some normal cell processes, including cell locomotion and cell division. Cell blebbing can be manipulated by mechanical or chemical treatment. It can be induced following microtubule disassembly, by inhibition of actin polymerization, increasing membrane rigidity or inactivating myosin motors, and by modulating intracellular pressure. Blebbing can also be induced in response to various extracellular chemical stimuli, such as exposure to agents that bind up sulfhydryl groups (i.e., sulfhydryl blocking agents), exposure to inhibitors of energy metabolism, or exposure to agents that cause ion deregulation.

The term "bioorthogonally-conjugated induced cell vesicle" as used herein, refers to an induced cell vesicle that surface has been modified by bioorthogonal chemistry. Accordingly, an "bioorthogonally-conjugated induced cell vesicle" of the disclosure can be specifically tuned for certain applications, like detection or therapeutic delivery, based upon the surface modification. In a particular embodiment, the surface of the induced cell vesicle has been bioorthogonally modified by tethering or affixing aminooxy-functionalized molecules to aldehyde groups of oxidized sialylated glycoproteins found on the induced cell vesicle surface.

The term "chemical agent that induces blebbing" as used herein, refers to a small molecule compound that when administered induces plasma membrane blebbing in cells, usually by causing injuries to cells which result in changes to cytosolic calcium ($Ca^{2+}$) levels. Examples of chemical agents that can be used in the methods or compositions disclosed herein to induce blebbing include, agents that block or bind up sulfhydryl groups, such as mercury chloride, p-chloromercuribenzene sulfonic acid, auric chloride, p-chloromercuribenzoate, chlormerodrin, meralluride sodium, iodoacetamide, paraformaldehyde and N-ethylmaleimide; inhibitors of energy metabolism, such as carbonyl cyanide, m-chlorophenylhydrazone, trivalent arsenicals, potassium cyanate, and potassium cyanate and iodoacetate; agents that cause ion deregulation, such as ouabain, ionomycin, and A23187; and agents that induce oxidative stress, such as menadione. In a particular embodiment, the chemical agent that induces cell membrane blebbing is a sulfhydryl blocking agent.

The terms "cancer" and "cancerous" as used herein, refer to or describe the physiological condition in mammals that is typically characterized by unregulated cell growth/proliferation. Examples of cancer include, but are not limited to, carcinoma, lymphoma (e.g., Hodgkin's and non-Hodgkin's lymphoma), blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulvar cancer, thyroid cancer, hepatic carcinoma, leukemia and other lymphoproliferative disorders, and various types of head and neck cancers.

The terms "cell proliferative disorder" and "proliferative disorder" as used herein, refer to disorders that are associated with some degree of abnormal cell proliferation. In one embodiment, the cell proliferative disorder is a tumor. In one embodiment, the cell proliferative disorder is cancer.

The term "CRISPR-Cas system", "CRISPRi system" or "CRISPR-Cpf1 system" as used herein refers to all the components that can be or are used to perform gene editing using a CRISPR gene editing system, including components, such as plasmids, guide RNAs (e.g., crRNAs), Cas proteins (e.g., Cas-3, Cas-9), and Cpf1 proteins.

The term "effective amount" as used herein, refers to an amount that is sufficient to produce at least a reproducibly detectable amount of the desired results. An effective amount will vary with the specific conditions and circumstances. Such an amount can be determined by the skilled practitioner for a given situation.

The term "immunotherapy" as used herein, refers to treatment that uses the subject's own immune system to combat a disease or disorder, such as cancer. Immunotherapy includes treatment that works in different ways, such as boosting the subject's immune system in a general way, or training the immune system to specifically attack disease or abnormal cells or tissue.

The term "cancer vaccine" as used herein, refers to an immunotherapy treatment that tries to stimulate the immune system to mount an attack against cancer cells in the body. A "cancer vaccine" may be made from antigenic ICVs made from a cancer subject's own cells that are then administered to the same subject as a cancer vaccine. Alternatively, the cells used to make the antigenic ICVs may come from someone other than the cancer subject to be treated.

The term "inhibiting tumor cell growth or proliferation" as used herein, means decreasing a tumor cell's growth or proliferation by at least 10%, 20%, 30%, 40%, 50%, 60%, 70%, 80%, 90%, 95%, or 100%, and includes inducing cell death in a cell or cells within a cell mass.

The terms "patient", "subject" and "individual" are used interchangeably herein, and refer to an animal, particularly a human, to whom treatment including prophylaxis treatment is provided. This includes human and non-human animals. The term "non-human animals" and "non-human mammals" are used interchangeably herein includes all vertebrates, e.g., mammals, such as non-human primates, (particularly higher primates), sheep, dog, rodent (e.g., mouse or rat), guinea pig, goat, pig, cat, rabbits, cows, and non-mammals such as chickens, amphibians, reptiles etc. In one embodiment, the subject is human. In another embodiment, the subject is an experimental animal or animal substitute as a disease model. "Mammal" refers to any animal classified as a mammal, including humans, non-human primates, domestic and farm animals, and zoo, sports, or pet animals, such as dogs, cats, cattle, horses, sheep, pigs, goats, rabbits, etc. Patient or subject includes any subset of the foregoing, e.g., all of the above, but excluding one or more groups or species such as humans, primates or rodents. A subject can be male or female. A subject can be a fully developed subject (e.g., an adult) or a subject undergoing the developmental process (e.g., a child, infant or fetus).

The term "photoinitiated induced cell vesicle" as used herein, refers to cells that have been incubated or exposed to a photosensitizer that induces the production of cell vesicles once exposed to light.

The term "photosensitizer" as used herein, refer to a molecule that produces a chemical change in another molecule in a photochemical process. Photosensitizers generally act by absorbing ultraviolet or visible region of electromagnetic radiation and transferring it to adjacent molecules. Photosensitizers usually have large de-localized 7E systems, which lower the energy of HOMO orbitals and its absorption of light might be able to ionize the molecule. Photosensitizers are a key part of photodynamic therapy (PDT) which is used to treat some cancers. They help to produce singlet oxygen to damage tumors. They can generally be divided into porphyrins, chlorophylls and dyes.

The term "purified" when used in reference to an induced cell vesicle disclosed herein, refers to the fact that it is removed from the majority of other cellular components from which it was generated or in which it is typically present in nature. The induced cell vesicles disclosed herein are typically prepared to the state where they are purified or semi-purified.

The term "sulfhydryl blocking agent" as used herein, refers to compound or reagent that interacts with cellular sulfhydryl groups so that the sulfhydryl groups are blocked or bound up by the sulfhydryl blocking agent, typically via alkylation or disulfide exchange reactions.

The term "therapeutically effective amount" as used herein, refers to an amount that is sufficient to affect a therapeutically significant reduction in one or more symptoms of the condition when administered to a typical subject who has the condition. A therapeutically significant reduction in a symptom is, e.g., about 10%, about 20%, about 30%, about 40%, about 50%, about 60%, about 70%, about 80%, about 90%, about 100%, or more as compared to a control or non-treated subject.

The term "treat" or "treatment" as used herein, refers to a therapeutic treatment wherein the object is to eliminate or lessen symptoms. Beneficial or desired clinical results include, but are not limited to, elimination of symptoms, alleviation of symptoms, diminishment of extent of condition, stabilized (i.e., not worsening) state of condition, delay or slowing of progression of the condition.

Extracellular vesicles (EVs) are cell membrane-derived particles naturally formed and released by all cells. As they are derived from cells themselves, EVs exhibit similar anatomy. They are composed of a lipid bilayer and present and contain similar molecules as their parent cell but without organelles (mitochondria, nucleus, etc.). EVs can be categorized into two general groups for therapeutic use, exosomes and microvesicles. Exosomes are 20-100 nm in diameter formed by invagination of multivesicular bodies (MVB) and released by subsequent MVB fusion with the plasma membrane. Microvesicles are 100-1000 nm in diameter and are released by direct blebbing from the plasma membrane.

Extracellular vesicles also play major roles in cell signaling, cell communication, and in the pathology of disease. As such, EVs have been designed and evolved by nature to effectively transfer internalized material to cells, making them excellent candidates for bio-active drug delivery vehicles. Cells in culture naturally produce EVs but at a rate significantly below the requirements for therapeutic administration, which has been attempted to be mitigated by exposing cells to endosomal trafficking regulators, modified proteins, and external stressors. However, these time- and labor-intensive processes directly affect cellular activities and make it difficult to preserve the composition and biological functions of EVs at a desired cellular stage.

Extracellular vesicle-based therapeutics are currently hindered from clinical advancement due to issues in mass production. To address this challenge, exploration in increasing EV production has been pursued by methods including starvation, manipulating intracellular calcium levels, thermal stress, hypoxia, radiation, and micro-environmental pH. These production methods require between 12-48 hours to achieve significantly improved yields. The disclosure provides for techniques and methods that provide for high yields of induced cell vesicles (ICVs) in as little as a few minutes, producing both micro and nano-scale sized ICVs. For example, the $AlPcS_{2,4}$ photoinitiated blebbing methods and techniques disclosed herein can induce cell vesicle production immediately after light exposure. Accordingly, the techniques and methods disclosed herein can induce cell vesicle production faster, more efficiently, and at higher yields than standard extracellular vesicle production techniques.

Any cell which naturally secretes extracellular vesicles may be used to induce cell vesicles by using the cell blebbing methods and techniques disclosed herein. As such, nearly any type of cell can be used with the cell blebbing methods and techniques disclosed herein to induce cell vesicles. In a particular embodiment, the cells used to induce cell vesicle production are selected from epithelial cells, fibroblast cells, tumor cells and cells of the immune system (mast cells, T and B lymphocytes, dendritic cells, especially Langerhans cells). In one embodiment, the ICV producing cell is a eukaryotic cell comprising internal vesicles for secretion. In another embodiment the cell is an ICV producing cell that is available commercially from ATTC® or other suppliers. In a further embodiment the ICV producing cell is capable of exocytosis. In yet a further embodiment, the ICV producing cell has been modified genetically, e.g., by gene editing, gene knockout, gene therapy, homologous recombination, site directed mutagenesis, transfection with plasmids and vectors, and the like. In another embodiment, the ICV producing cell has been modified on its surface using the bioorthogonally conjugation methods disclosed herein, or any other surface engineering method known in the art. Cells that can be used to produce ICVs include, without limitation, skin fibroblasts, mast cells, T and B lymphocytes and dendritic cells (for example Langerhans cells), or cells derived from these cell types, and cells or cell lines modified by genetic engineering so as to render them capable of secreting ICVs. In a particular embodiment, the cell used to produce antigenic ICV is a dendritic cell. In further embodiment, the dendritic cell is a bone marrow derived dendritic cell.

In a particular embodiment, ICVs may be produced from a mammalian cell by contacting the mammalian cell with a chemical agent that induces blebbing. Examples of such chemical agents include, but are not limited to, photosensitizers, mercury chloride, p-chloromercuribenzene sulfonic acid, auric chloride, p-chloromercuribenzoate, chlormerodrin, meralluride sodium, iodoacetamide, maleimide, cyanide, m-chlorophenylhydrazone, trivalent arsenicals, potassium cyanate, and potassium cyanate and iodoacetate, glyoxal, acrolein, methacrolein, pyridoxal, N-ethylmaleimide (NEM), maleimide, chloromercuribenzoate, iodoacetate, potassium arsenite, sodium selenite, thimerosal (merthiolate), benzoyl peroxide, cadmium chloride, hydrogen peroxide, iodosobenzoic acid, meralluride sodium, (mercuhydrin), mercuric chloride, mercurous chloride, chlormerodrin (neohydrin), phenylhydrazine, potassium tellurite, sodium malonate, p-arsenosobenzoic acid, 5,5'-diamino-2,2'-dimethyl arsenobenzene, N,N'-dimethylene sulfonate disodium salt, iodoacetamide, oxophenarsine (mapharsen), auric chloride, p-chloromercuribenzoic acid, p-chloromercuripheny-isullonic acid, cupric chloride, iodine merbromin (mercurochrome)porphyrindine, potassium permanganate, mersalyl (salyrgan), silver nitrate, strong silver protein (protargol), and uranyl acetate.

In a particular embodiment, ICVs are produced from a cell by contacting or exposing the cell to N-ethylmaleimide. In a further embodiment, the cell is incubated with a cell blebbing buffer that comprises or consists essentially of N-ethylmaleimide at a concentration of 0.5 mM, 0.6 mM, 0.7 mM, 0.8 mM, 0.9 mM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.1 mM, 2.2 mM, 2.3 mM, 2.4 mM, 2.5 mM, 2.6 mM, 2.7 mM, 2.8 mM, 2.9 mM, 3.0 mM, 3.1 mM, 3.2 mM, 3.3 mM, 3.4 mM, 3.5 mM, 3.6 mM, 3.7 mM, 3.8 mM, 3.9 mM, 4.0 mM, 4.1 mM, 4.2 mM, 4.3 mM, 4.4 mM, 4.5 mM, 4.6 mM, 4.7 mM, 4.8 mM, 4.9 mM, 5.0 mM, 6.0 mM, 7.0 mM, 8.0 mM, 9.0 mM, 0.01 M, 0.1 M, 1.0 M, 1.5 M, 2.0 M, or a range that includes or is between any two of the foregoing concentrations, including fractional increments thereof. In a further embodiment, the cell blebbing buffer further comprises a buffered balanced salt solution. Examples of buffered saline solutions include but are not limited to, phosphate-buffered saline (PBS), Dulbecco's Phosphate-buffered saline (DPBS), Earle's Balanced Salt solution (EBSS), Hank's Balanced Salt Solution (HBSS), TRIS-buffered saline (TBS), and Ringer's balanced salt solution (RBSS). In a further embodiment, the cell blebbing buffer containing a sulfhydryl blocking agent or NEM further comprises a buffered balanced salt solution at a concentration/dilution of 0.5×, 0.6×, 0.7×, 0.8×, 0.9×, 1×, 2×, 3×, 4×, 5×, 6×, 7×, 8×, 9×, and 10×, or a range that includes or is between any two of the foregoing concentrations/dilutions, including fractional increments thereof. In yet a further embodiment, the cells are incubated in a cell blebbing buffer containing a sulfhydryl blocking agent or NEM for 0.5 h, 1 h, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h, 36 h, 48 h, 72 h or a range that includes or is between any two of the foregoing time points, including fractional values thereof.

In another embodiment, ICVs are produced from a cell by contacting or exposing the cell to paraformaldehyde (PFA). In an another embodiment, the cell is incubated with a cell blebbing buffer that comprises or consists essentially of PFA at a concentration of 10.0 mM, 12.0 mM, 14.0 mM, 15.0 mM, 16.0 mM, 18.0 mM, 20.0 mM, 21.0 mM, 22.0 mM, 23.0 mM, 24.0 mM, 25.0 mM, 26.0 mM, 27.0 mM, 28.0 mM, 29.0 mM, 30.0 mM, 32.0 mM, 34.0 mM, 35.0 mM, 40.0 mM, 45.0 mM, 50.0 mM, 100.0 mM, 200.00 mM or a range that includes or is between any two of the foregoing concentrations, including fractional values thereof. In a further embodiment, the cell blebbing buffer comprising PFA further comprises a buffered balanced salt solution. Examples of buffered saline solutions include but are not limited to, phosphate-buffered saline (PBS), Dulbecco's Phosphate-buffered saline (DPBS), Earle's Balanced Salt solution (EBSS), Hank's Balanced Salt Solution (HBSS), TRIS-buffered saline (TBS), and Ringer's balanced salt solution (RBSS). In a further embodiment, the cell blebbing buffer comprising PFA further comprises a buffered balanced salt solution at a concentration/dilution of 0.5×, 0.6×, 0.7×, 0.8×, 0.9×, 1×, 2×, 3×, 4×, 5×, 6×, 7×, 8×, 9×, and 10×, or a range that includes or is between any two of the foregoing concentrations/dilutions, including fractional values thereof. In a further embodiment, the cell blebbing buffer that comprises or consists essentially of PFA does not contain any small molecule redox reagents or reducing agents (e.g., dithiothreitol (DTT)). In yet a further embodiment, the cells are incubated in a cell blebbing buffer containing PFA for 0.5 h, 1 h, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h, 36 h, 48 h, 72 h or a range that includes or is between any two of the foregoing time points, including fractional values thereof.

In a particular embodiment, ICVs may be produced from a cell by contacting the cell with a photosensitizer that induces blebbing. In the studies provided herein, HeLa cells were induced to undergo blebbing and ICV production by incubating or exposing the HeLa cells to a photosensitizer (e.g., $AlPcS_{2A}$) and then exposing the cells to light. It was discovered that the size of generated ICVs was largely in the micrometer or nanometer size range. Further, it was shown herein that the methods of the disclosure efficiently produced nanometer/micrometer ICVs almost immediately upon light exposure without the need to add other chemical agents, like reducing agents (e.g., DTT), agents that interact with sulfhydryl groups (e.g., N-ethylmaleimide), inhibitors of energy metabolism (e.g., cyanates), and agents that induce oxidative stress (e.g., menadione). Moreover, the studies presented herein demonstrate that the size allocation of the ICVs could be controlled based upon length of the light exposure dose.

In a particular embodiment, ICVs may be produced from a cell by incubating or exposing the cell with a photosensitizer and then exposing the cell to light. Examples of such photosensitizers include, but are not limited to, $AlPcS_{2A}$, $AlPcS_4$, lutrin, 5-aminolevulinic acid (ALA), hypericin, silicon phthalocyanine zinc (II) phthalocyanine (ZnPc), silicon phthalocyanine, mono-L-aspartyl chlorin e6, benzoporphyrin derivative monoacid ring A, chlorin photosensitizer tin etiopurpurin, tetra(m-hydroxyphenyl)chlorin, lutetium texaphyrin, 9-acetoxy-2,7,12,17-tetrakis-(β-methoxyethyl)-porphycene, naphthalocyanines, Allumera®, Photofrin®, Visudyne®, Levulan®, Foscan®, Fospeg®, Metvix®, Hexvix®, Cysview® and Laserphyrin®, Antrin®, Photochlor®, Photosens®, Photrex®, Lumacan®, Cevira®, Visonac®, BF-200 ALA®, Amphinex® and Azadipyrromethenes. In a further embodiment, ICVs are produced from a cell by incubating or exposing the cell with $AlPcS_{2A}$ and the exposing the cells to light having a wavelength from 600 nm to 850 nm. In a further embodiment, the cell is incubated in the dark with a photosensitive media that comprises or consists essentially of a photosensitizer (e.g., $AlPcS_{2A}$) at a concentration of 0.1 ug/mL, 0.2 ug/mL, 0.3 ug/mL, 0.4 ug/mL, 0.5 ug/mL, 0.6 ug/mL, 0.7 ug/mL, 0.8 ug/mL, 0.9 ug/mL, 1.0 ug/mL, 1.1 ug/mL, 1.2 ug/mL, 1.3 ug/mL, 1.4 ug/mL, 1.5 ug/mL, 1.6 ug/mL, 1.7 ug/mL, 1.8 ug/mL, 1.9 ug/mL, 2.0 ug/mL, 2.5 ug/mL, 3.0 ug/mL, 3.5 ug/mL, 4.0 ug/mL, 4.5 ug/mL, 5.0 ug/mL, 10.0 ug/mL or a range that includes or is between any two of the foregoing concentrations, including fractional values thereof. In yet a further embodiment, the cell is incubated in the dark with a photosensitive media that comprises or consists essentially of a photosensitizer (e.g., $AlPcS_{2A}$) for 0.5 h, 1 h, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h, 36 h, 48 h, 72 h or a range that includes or is between any two of the foregoing time points, including fractional values thereof. In another embodiment, the cells contacted with the photosensitizer are exposed to light for 1 min, 2 min, 3 min, 4 min, 5 min, 6 min, 7 min, 8 min, 9 min, 10 min, 12 min, 14 min, 15 min, 16 min, 18 min, 20 min, 25 min, 30 min, 35 min, 40 min, 45 min, 50 min, 55 min, 60 min, 90 min, 120 min, or a range that includes or is between any two of the foregoing timepoints, including fractional values thereof. In a further embodiment, the cells are exposed to light generated from a laser. In yet a further embodiment, the cells are exposed to light having a wavelength of 500 nm, 550 nm, 580 nm, 600 nm, 610 nm, 620 nm, 630 nm, 640 nm, 650 nm, 660 nm, 670 nm, 680 nm, 690 nm, 700 nm, 720 nm, 740 nm, 760 nm, 780 nm, 800 nm, 850 nm, 900 nm that is generated by a laser, or a range that includes or is between any two of the foregoing wavelengths, including fractional values thereof.

The disclosure further provides that the ICVs may be collected by any suitable means to separate ICVs from cells or cell debris. In some embodiments, to isolate ICVs, cells can be removed by centrifugation at 1,000 to 2,500 rpm for 1 minutes, 1.5 minutes, 2 minutes, 2.5 minutes, 3 minutes, 3.5 minutes, 4 minutes, 4.5 minutes, 5 minutes, 5.5 minutes, 6 minutes, 6.5 minutes, 7 minutes, 7.5 minutes, 8 minutes, 8.5 minutes, 9 minutes, 9.5 minutes, 10 minutes, or a range that includes or is between any two of the forgoing timepoints, including fractional increments thereof, followed by removal of cell debris. Induce cell vesicles can then be recovered by centrifugation at 8,000×g to 20,000×g for 5 minutes, 6 minutes, 7 minutes, 8 minutes, 9 minutes, 10 minutes, 11 minutes, 12 minutes, 13 minutes, 14 minutes, or 15 minutes, or a range that includes or is between any two of the forgoing timepoints, including fractional increments thereof. ICVs can be further concentrated using concentrators with a size cutoff of 100 kDA or less. In a particular embodiment, ICVs can be concentrated with a 30 kDa Amicon® concentrator by centrifuging at 4,500 rpm for 15 minutes for one or more cycles. The disclosure also provides that the ICVs may be collected of further purified by use of sucrose gradients.

To increase the applications of the ICVs the surfaces of the ICVs may modified to comprise one or more functional moieties using the methods disclosed herein. Such functional moieties can provide for a variety of beneficial effects, including, but not limited to, easy purification and concentration of the ICVs; targeted delivery of the ICVs; controlled cellular uptake of the ICVs; monitoring of intracellular pathways using the ICVs; and molecular imaging of the ICVs. The functional moieties for ICVs may originate from the cells used to produce the ICVs. In such a case, the functional moieties may naturally occur on the surface of the cells that are treated with the blebbing methods disclosed herein. For example, when treated with TNF-α, human umbilical vein endothelial cells (HUVEC) overexpress ICAM-1 in the plasma membrane [J. Exp. Med. 177; 1277-1286 (1993)]. In monocytes treated with PMA (phorbol 12-myristate 13-acetate), the membrane protein LFA-1 is activated [J. Exp. Med. 163; 1132-1149 (1986)]. [Human Gene Therapy. 7(11); 1339-1346 (1996)] or other methods known in the art. Alternatively, the functional moieties for ICVs may result from recombinant expression of the functional moieties in the ICV producing cells. In this context, plasmid DNA, RNA or virus is introduced into cells [PNAS. 90 (18); 8392-8396 (1993)] using calcium phosphate precipitation [Current Protocols in Cell Biology 20.3.1-20.3.8 (2003)], lipofectamine mediation [PNAS. 84 (21); 7413-7417 (1987)], electroporation [Nucleic Acids Research. 15 (3) 1311-1326 (1987)], microinjection [Mol Cell Biol. 2(9); 1145-1154 (1982)], ultrasound mediation. The functional moieties may be anchored to the outer membrane surface of the cells, by use of anchoring motifs and the like, such as the transmembrane domain of human platelet derived growth factor receptor; outer membrane proteins, lipoproteins, autotransporters. Use of cell anchoring motifs are known in the art and can be used to anchor the functional moieties (e.g., receptor ligands, antigens, T cell stimulatory domains) to the cell surface (e.g., see Cheng et al., *J. Am. Chem. Soc.* 140:16413-16417 (2018)). Alternatively, the surface of the ICVs can be modified to comprise one or more functional moieties. Such modifications can result from coupling functional moieties to proteins or other biomolecules found on the surface of ICVs.

In another embodiment, the surface of the ICVs have been modified to comprise one or more functional moieties that are targeting ligands. Such targeting ligands may originate from the cell used to produce the ICVs, i.e., the cell naturally expresses the targeting ligand; or the targeting ligand may be recombinant expressed in the ICV producing cell; or the targeting ligand may be fixed to the ICV or ICV producing cell surface by use of the surface modification techniques disclosed herein or known in the art (see U.S. Pat. No. 10,308,942). In yet another embodiment, the targeting ligand may direct ICVs to, for example, a cell, cell type, tissue type or organ. For example, the targeting ligand may specifically or non-specifically bind with a molecule on the surface of a target cell. The targeting moiety can be a molecule with a specific affinity for a target cell. Targeting moieties can include antibodies or scFVs directed against a protein found on the surface of a target cell, or the ligand or a receptor-binding portion of a ligand for a molecule found on the surface of a target cell. For example, the targeting moiety can recognize a tumor-specific antigen. Examples of tumor-specific antigens include, but are not limited to, alpha-fetoprotein (AFP), carcinoembryonic antigen (CEA), CA-125, CA15-3, CA19-9, MUC-1, epithelial tumor antigen (ETA), tyrosinase, melanoma-associated antigen (MAGE), abnormal products of ras or p53, CTAG1B, MAGEA1, and HER2/neu. In a further embodiment, the target cells or tissue are also subjected to a second event. A second event is used, for example, to activate a conditionally therapeutic molecule. Such a second event can be exposure to a second molecule (e.g., extracellularly or delivery intracellularly) such as a prodrug. In one embodiment the second molecule is administered to a subject locally to the relative location of the target cells within the subject (e.g., injection into a tumor or organ). The second molecule may be a pro-drug or an activator of the therapeutic molecule, or a molecule involved in specific delivery of the therapeutic molecule to the target cell or tissue.

In a particular embodiment, the cellular membranes of ICVs can be modified to comprise one or more functional moieties by chemical conjugation methods, or by expressing one or more functional moieties of interest using expression vectors, viral vectors, etc. in the ICV producing cells. In another embodiment, the disclosure also provides for modifying the surface of ICVs to comprise one or more functional moieties by using bioorthogonally conjugation. The bioorthogonally conjugation methods disclosed herein provide for facile introduction of desired functional moieties onto the membrane surface of the ICVs. Therefore, the fast, convenient, versatile, and efficient methods of the disclosure afford for synthetically functionalized ICVs that have great utility in a variety of applications, including, targeted delivery for therapeutics, imaging, and detection. Thus, the disclosure provides for the use of bioorthogonal chemistry for all-purpose surface modification of ICVs, and further that the bioorthogonal chemistry techniques can also be used with any ICV producing cell. The methods of the disclosure allow for rapid isolation of the ICVs via the one or more functional moieties, as well as custom tuning of the ICVs interactions with target cells, cellular uptake/intracellular processes, and monitoring the ICVs activities in vitro and in vivo.

In contrast to other surface modification techniques, the bioorthogonal approach avoids randomly introducing conjugates and disrupting envelope membrane and proteins. Applying simple chemistry at the cellular level resolves the problem of implementing difficult and laborious genetic alterations. The methods disclosed herein are highly efficient and specific under physiological conditions (e.g., cell culture medium), which allows for modification of ICV producing cells, and the resultant ICVs, with desired molecules. As demonstrated using an ICV-like, enveloped viruses, the method of disclosure can be easily applied to bioorthogonally conjugated ICVs induced by sulfhydryl blocking.

The disclosure provides for techniques and methods that provide for high yields of bioorthogonally-conjugated ICVs in as little as a few hours, producing both micro and nano-scale sized bioorthogonally-conjugated ICVs. For example, use of the sulfhydryl blocking agent to induce cell membrane blebbing described herein, can initiate the production of bioorthogonally-conjugated ICVs in as little as 2 h to 5 h.

In the studies provided herein, bioorthogonal chemistry was used to efficiently modify ICVs through modifying the ICV producing cells. ICVs are derived from the cellular membrane during the budding process and carry the biochemical properties of the ICV producing cell membrane. In other words, bioorthogonal modification of the membranes of the ICV producing cells provides for bioorthogonal functionalized ICVs. Any of the ICV producing cells described herein may be used to make bioorthogonal functionalized ICVs. In a particular, embodiment, the ICV producing cell comprises sialic acids on the surface of the cell. As shown in the experiments presented herein, sialic acids on the cell surface can be oxidized to aldehydes using oxidizing reagents, like sodium periodate or lead tetraacetate. Particular examples of oxidizing sialic acids on cells surfaces are described in Zeng et al., Nat Methods, 2009, 6, 2017, which is incorporated herein in-full. By use of oxime ligation, aminooxy-functionalized molecules can be linked to the aldehydes made from oxidizing sialic acid residues on the cell surface using bioorthogonal chemistry. Specific aminooxy-functionalized molecules can be purchased commercially (e.g., Sigma-Aldrich, ThermoFisher, etc.), or can be made de-novo using established methods in the art (e.g., Peri et al. *Tetrahedron* 1998, 54, 12269; Carrasco et al., *Tetrahedron Lett.* 2002, 43, 5727; Carrasco et al., *J. Org. Chem.* 2003, 68, 8853; Seo et al., *Org. Lett.* 2009, 11, 5210; Matsubara et al., *Chem-Eur. J.* 2005, 11, 6974; Leung et al., *Carbohydr. Res.* 2009, 344, 570; Peri et al., *Chem. Commun.* 2002, 15041; Peri et al., *Chem-Eur. J.* 2004, 10, 1433; Bohorov et al., *Glycobiology* 2006, 16, 21C; Clo et al., *J. Org. Chem.* 2010, 540; and Carrasco et al., *J. Org. Chem.* 2010, 75, 5757).

The ICVs disclosed herein can be used to treat diseases which can be ameliorated by the delivery or the actions of the therapeutic molecules (e.g., antisense oligonucleotides, CRISPR-Cas system, small molecule therapeutics, etc.) gene therapy or immunotherapy on the targeted disease-causing cells or tissue. In one embodiment, the disease involves or is caused by a genetic deficiency in the target cells. The molecule for which they are deficient (or encoding the molecule for which they are deficient) can be delivered to the appropriate cells via the ICVs disclosed herein.

Figure 22:
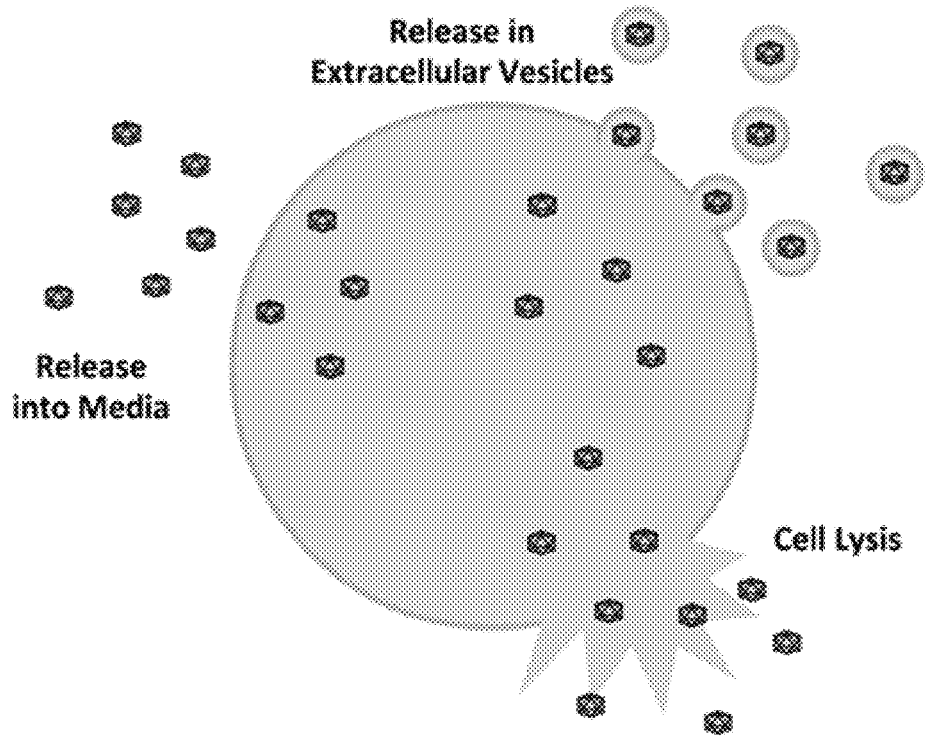
FIG. 22 illustrates how adeno-associated virus replicates within cells. The virus can be released in three ways: directly in media, in cell vesicles, and through cell lysis and collection. The cell blebbing methods disclosed herein induce the mass scale production of AAV containing cell vesicles in a rapid and efficient manner.
Figure 23:
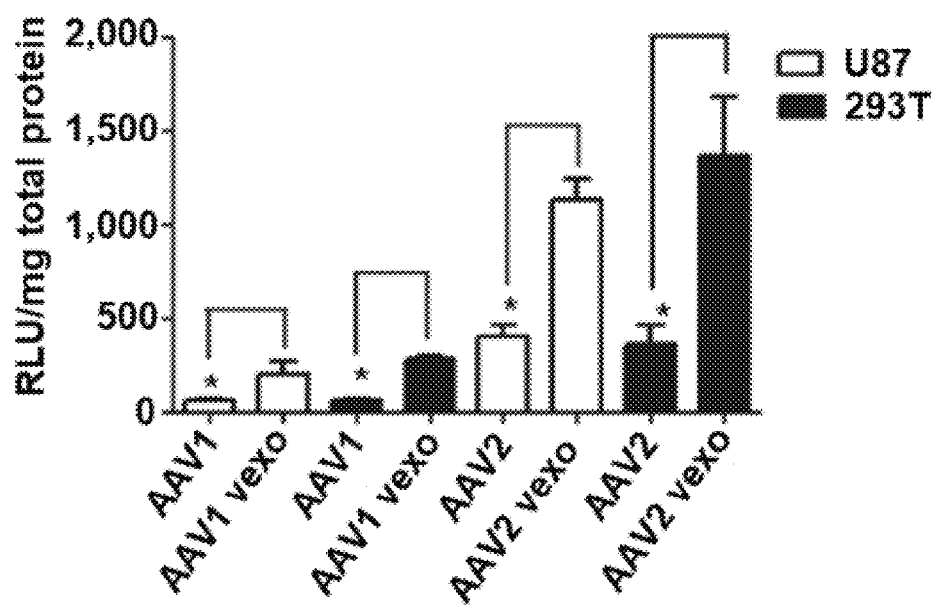
FIG. 23 demonstrates that there is an increase in transduction of AAV when AAV encapsulated by vesicles, as denoted by AAV vexo. The presented experiment was performed in Hek293T and U87 glioblastoma cells. Figure is prior art from Maguire et al. (2012). Microvesicles-associated AAV vector as a novel gene delivery system. Molecular Therapy, 20(5), 960-971).

In a particular embodiment, the ICVs of the disclosure can be used to deliver gene therapies components, such as a gene therapy viral vector. For example, in the studies presented herein, it was found that the methods of the disclosure allow for the packaging of viral particles into induced cell vesicles. Generally, when AAV replicates in a cell it can be released directly or remains in the cell. The disclosure, however, provides a third option, the encapsulation of AAV particles in induced cell vesicles (e.g., see FIG. 22). ICVs that contain AAV can be isolated and purified using the methods disclosed herein, and then used as an effective delivery vehicle to targeted cells or tissue. Studies have shown that extracellular vesicle encapsulated AAV can increase the transduction of AAV into the target cell lines. Encapsulating AAV in this envelope has been shown to increase delivery to cells over naked AAV alone (e.g., se FIG. 23). The extracellular vesicle associated AAVs were shown to be more effective both in vitro and in vivo, owing to the natural role of extracellular vesicles as signaling agents. With vesicle encapsulating AAV, the capsid is blocked from recognition by the immune system. This masking reduces neutralization of the AAV, giving it a longer time to reach and infect the target cells. Despite this system's potential, extracellular vesicle-based therapeutics are currently hindered from clinical advancement due to issues in mass production. To address this challenge, exploration in increasing extracellular vesicle production has been pursued by methods including starvation, manipulating intracellular calcium levels, thermal stress, hypoxia, radiation, and micro-environmental pH. These production methods require between 12-48 hours to achieve significantly improved yields. So, while extracellular vesicles containing AAV are recognized as excellent candidates for viral gene therapy, the use of such agents in clinical trials has been prohibitive due to issues with mass production.

Provided herein are protocols and methods which avoid the foregoing drawbacks by inducing membrane blebbing by: (1) use of a photosensitizer (e.g., AlPCS2A photosensitizer) and exposure to a certain wavelength of light (e.g., 670 nm light), and/or (2) use of a membrane blebbing inducing agent (e.g., NEM or PAF) to initiate mass-scale production of micro and nanoscale AAV-containing ICVs. The techniques and methods disclosed herein provide for the quick and efficient AAV-containing ICV formation that is substantial faster and more efficient, with higher yields, to current AAV-containing-vesicle production techniques. For example, through the use of AlPCS2A, a clinical grade photosensitizing agent, can induce AAV-containing ICV production in just minutes and produces both micro and nano-scale AAV-containing ICVs. Other photosensitizing agents (i.e., photosensitizers) that can be used to produce AAV-containing ICVs are further described herein. In another example presented herein, the use of chemical agent (e.g., NEM) can initiate AAV-containing ICVs secretion in 2-5 h. Other chemical agents, e.g., PAF, that can be used to produce AAV-containing ICVs from AAV producer cells are further described herein.

While AAV-containing ICVs are shown in the exemplary studies presented herein, it should be understood that the methods and compositions of the disclosure work equally well to produce ICVs that contain any type of viral particles, vectors or viruses. For example, the methods and compositions of the disclosure can be used to produce ICVs which comprise recombinant retroviruses, adenovirus, adeno-associated virus, alphavirus, or lentivirus.

In a particular embodiment, the disclosure provides for ICVs which comprise an adeno-associated virus (AAV). AAV is a tiny non-enveloped virus having a 25 nm capsid. No disease is known or has been shown to be associated with the wild type virus. AAV has a single-stranded DNA (ssDNA) genome. AAV has been shown to exhibit long-term episomal transgene expression, and AAV has demonstrated excellent transgene expression in the brain, particularly in neurons. Vectors containing as little as 300 base pairs of AAV can be packaged and can integrate. Space for exogenous DNA is limited to about 4.7 kb. An AAV vector such as that described in Tratschin et al., *Mol. Cell. Biol.* 5:3251-3260 (1985) can be used to introduce DNA into cells. A variety of nucleic acids have been introduced into different cell types using AAV vectors (see for example Hermonat et al., *Proc. Natl. Acad. Sci. USA* 81:6466-6470 (1984); Tratschin et al., *Mol. Cell. Biol.* 4:2072-2081 (1985); Wondisford et al., *Mol. Endocrinol.* 2:32-39 (1988); Tratschin et al., *J. Virol.* 51:611-619 (1984); and Flotte et al., *J. Biol. Chem.* 268:3781-.3790 (1993). There are numerous alternative AAV variants (over 100 have been cloned), and AAV variants have been identified based on desirable characteristics. For example, AAV9 has been shown to efficiently cross the blood-brain barrier. Moreover, the AAV capsid can be genetically engineered to increase transduction efficient and selectivity, e.g., biotinylated AAV vectors, directed molecular evolution, self-complementary AAV genomes and so on. Modified AAV have also been described, including AAV based on ancestral sequences; see, e.g., U.S. Pat. No. 7,906,111; WO/2005/033321; WO2008027084, WO2014124282; WO2015054653; and WO2007127264. Other modified AAVs that have been described include chimeric nanoparticles (ChNPs) that have an AAV core that expresses a transgene that is surrounded by layer(s) of acid labile polymers that have embedded antisense oligonucleotides (e.g., see Hong et al., ACS Nano 10:8705-8716 (2016)) and Cho et al., Biomaterials 2012, 33, 3316-3323). The compositions and methods disclosed herein is a platform technology, and as such the composition and methods disclosed herein can be used with all known AAVs, including the modified AAVs described in the literature.

Alternatively, the disclosure also provides for ICVs which comprise retroviruses. Retroviruses can be used as a recombinant gene delivery system for the transfer of exogenous genes in vivo, particularly into humans. Retroviruses provide efficient delivery of genes into cells, and the transferred nucleic acids are stably integrated into the chromosomal DNA of the host. The development of specialized cell lines (termed "packaging cells") which produce only replication-defective retroviruses has increased the utility of retroviruses for viral gene therapy, and defective retroviruses are characterized for use in gene transfer for viral gene therapy purposes (for a review see Miller, *Blood* 76:271 (1990)). A replication defective retrovirus can be packaged into virions, which can be used to infect a target cell through the use of a helper virus by standard techniques. Protocols for producing recombinant retroviruses and for infecting cells in vitro or in vivo with such viruses can be found in Ausubel, et al, eds., Current Protocols in Molecular Biology, Greene Publishing Associates, (1989), Sections 9.10-9.14, and other standard laboratory manuals. Examples of suitable retroviruses include pLJ, pZIP, pWE and pEM which are known to those skilled in the art. Examples of suitable packaging virus lines for preparing both ecotropic and amphotropic retroviral systems include Ψ&ip, Ψ&ε, Ψ2 and ΨAπι. Retroviruses have been used to introduce a variety of genes into many different cell types, including epithelial cells, in vitro and/or in vivo (see for example Eglitis, et al. (1985) Science 230: 1395-1398; Danos and Mulligan (1988) *Proc. Natl. Acad. Sci. USA* 85:6460-6464; Wilson et al. (1988) *Proc. Natl. Acad. Sci. USA* 85:3014-3018; Armentano et al. (1990) *Proc. Natl. Acad. Sci. USA* 87:6141-6145; Huber et al. (1991) *Proc. Natl. Acad. Sci. USA* 88:8039-8043; Ferry et al. (1991) *Proc. Natl. Acad. Sci. USA* 88:8377-8381; Chowdhury et al. (1991) Science 254: 1802-1805; van Beusechem et al. (1992) *Proc. Natl. Acad. Sci. USA* 89:7640-7644; Kay et al. (1992) Human Gene Therapy 3:641-647; Dai et al. (1992) *Proc. Natl. Acad. Sci. USA* 89: 10892-10895; Hwu et al. (1993) *J. Immunol.* 150:4104-4115; U.S. Pat. Nos. 4,868, 116; 4,980,286; PCT Application WO 89/07136; PCT Application WO 89/02468; PCT Application WO 89/05345; and PCT Application WO 92/07573). By using the methods of the disclosure, one can produce ICVs which comprise retroviruses or retroviral particle or vectors, in a manner similar to producing ICVs which contain AAV as described herein.

In another embodiment, the disclosure also provides for ICVs which comprise adenovirus-derived vectors. The genome of an adenovirus can be manipulated, such that it encodes and expresses a gene product of interest but is inactivated in terms of its ability to replicate in a normal lytic viral life cycle. See, for example, Berkner et al., *BioTechniques* 6:616 (1988); Rosenfeld et al., Science 252:431-434 (1991); and Rosenfeld et al., Cell 68: 143-155 (1992). Suitable adenoviral vectors derived from the adenovirus strain Ad type 5 dl324 or other strains of adenovirus (e.g., Ad2, Ad3, or Ad7 etc.) are known to those skilled in the art. Recombinant adenoviruses can be advantageous in certain circumstances, in that they are not capable of infecting non-dividing cells and can be used to infect a wide variety of cell types, including epithelial cells (Rosenfeld et al., (1992) supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situ, where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al., supra; Haj-Ahmand and Graham, J. Virol. 57:267 (1986). Alphaviruses can also be used. Alphaviruses are enveloped single stranded RNA viruses that have a broad host range, and when used in viral gene therapy protocols alphaviruses can provide high-level transient gene expression. Exemplary alphaviruses include the Semliki Forest virus (SFV), Sindbis virus (SIN) and Venezuelan Equine Encephalitis (VEE) virus, all of which have been genetically engineered to provide efficient replication-deficient and -competent expression vectors. Alphaviruses exhibit significant neurotropism, and so are useful for CNS-related diseases. See, e.g., Lundstrom, Viruses. 2009 June; 1(1): 13-25; Lundstrom, Viruses. 2014 June; 6(6): 2392-2415; Lundstrom, *Curr Gene Ther.* 2001 May; 1(1): 19-29; Rayner et al., *Rev Med Virol.* 2002 September-October; 12(5):279-96. By using the methods of the disclosure, one can produce ICVs which comprise adenovirus-derived particles, viruses or vectors, in a manner similar to producing ICVs which contain AAV as described herein.

The methods of the disclosure address some limitations of using viral vectors, such as AAV vectors, for gene transfer through the use of ICVs. For example, while microvesicles containing AAVs have been shown to be produced and outperform conventionally purified AAV vectors using standard culture conditions, the amount of microvesicles containing AAVs using standard culture conditions is a mere minor fraction of the total AAVs produced and released by the cultured cells (e.g., see Maguire et al., *Mol. Ther.* 20(5):960-971). In direct contrast, the methods disclosed herein, provided for mass production of ICVs which contain viruses, viral particles or viral vectors, by inducing blebbing in the cells that comprise a high percentage of the viruses, viral particles or viral vectors. Such cells that can be used in the blebbing methods are further described herein.

Cancer cells survive and proliferate by several mechanisms including immune evasion. Immunotherapy overcomes this by activating the immune system to eliminate cancer cells, and the most common strategy for activating the immune system against tumor cells is vaccination with tumor antigens. Previous studies have reported that bone marrow dendritic cells (BMDCs) pulsed with antigen ex vivo are able to act as an anti-cancer vaccine, presenting antigen in vivo and stimulating T cell response to eradicate tumor cells. However, intrinsic variability associated with whole-cell vaccine formulations has made them non-ideal candidates for immunotherapy.

Extracellular vesicles (EVs) are promising cell-free vaccines for cancer therapy. Extracellular vesicles (EVs) are cell membrane-derived particles naturally formed and released by all cells. As they are derived from cells themselves, EVs exhibit similar anatomy. They are composed of a lipid bilayer and present and contain similar molecules as their parent cell but without organelles (mitochondria, nucleus, etc.). EVs can be categorized into two general groups for therapeutic use, exosomes and microvesicles. Exosomes are 20-100 nm in diameter formed by invagination of multivesicular bodies (MVB) and released by subsequent MVB fusion with the plasma membrane. Microvesicles are 100-1000 nm in diameter and are released by direct blebbing from the plasma membrane.

Naturally occurring EVs are intrinsically biocompatible, maintaining similar plasma membrane characteristics to their parent cells. EVs maintain the intrinsic biocompatible benefits of cell therapy while gaining advantage with better storability, minimized risk, and ability to tailor size based on desired application. Several groups have demonstrated EVs as effective carriers of therapeutic cargo in vitro and in vivo. Cells in culture naturally produce EVs but at a rate significantly below the requirements for therapeutic administration, which has been attempted to be mitigated by exposing cells to endosomal trafficking regulators, modified proteins, and external stressors. However, these time- and labor-intensive processes directly affect cellular activities and make it difficult to preserve the composition and biological functions of EVs at a desired cellular stage.

As noted above, extracellular vesicle-based therapeutics are currently hindered from clinical advancement due to issues in mass production. To address this challenge, exploration in increasing EV production has been pursued by methods including starvation, manipulating intracellular calcium levels, thermal stress, hypoxia, radiation, and micro-environmental pH. These production methods require between 12-48 hours to achieve significantly improved yields. In addition to production problems, high-levels of variability in EV formulations have also hindered use of EV therapies in clinical trials. Reducing variability associated with EVs is necessary to ensuring safety and therapeutic efficacy. Antigen-pulsed dendritic cell derived EVs are a promising cell-free option for cancer immunotherapy, but intrinsic issues with heterogeneity of EV populations has slowed their progression to the clinic. Improving homogeneity, in particular maturation state of the parent cell and EV size, will be important for achieving effective immunotherapy.

The disclosure provides for techniques and methods that provide for high yields of antigen presenting or antigenic ICVs in as little as a few hours, producing both micro and nano-scale sized antigen presenting ICVs. For example, use of a sulfhydryl blocking agent described herein to induce blebbing, can induce cell vesicle production in as little as 2-5 h. Accordingly, the techniques and methods disclosed herein can induce fast, efficient and high yields of ICVs, which are simply not possible using current extracellular vesicle production techniques. It was further postulated herein that the blebbing methods of the disclosure would allow for control over the parent cell maturation state and improvement in homogeneity of the induced cell vesicles produced therefrom. As is shown herein, antigenic ICVs produced by the blebbing methods described herein maintained maturation characteristics of their parent cells and served as efficient cell-free cancer vaccines. Cells particularly suited for antigenic ICV production include, but are not limited to, epithelial cells, fibroblast cells, tumor cells and cells of the immune system (mast cells, T and B lymphocytes, dendritic cells, especially Langerhans cells). In a further embodiment the antigenic ICV producing cell is from a subject to be treated with an ICV disclosed herein. In yet a further embodiment, the antigenic ICV producing cell has been modified genetically, e.g., by gene editing, gene knockout, gene therapy, homologous recombination, site directed mutagenesis, transfection with plasmids and vectors, and the like. In a particular embodiment, the antigenic ICV producing cell is a cell of the immune system, including but not limited to, mast cells, T and B lymphocytes and dendritic cells (for example Langerhans cells and bone marrow derived dendritic cells), or cells derived from these cell types, and cells or cell lines modified by genetic engineering so as to render them capable of secreting ICVs.

In a certain embodiment, the disclosure further provides that that the antigenic ICV producing cell is an 'immature', 'semimature' or 'mature' dendritic cell. Dendritic cells (DCs) are the sentinel antigen-presenting cells of the immune system; such that their productive interface with the dying cancer cells is crucial for proper communication of the "non-self" status of cancer cells to the adaptive immune system. Efficiency and the ultimate success of such a communication hinges upon the maturation status of the DCs, attained following their interaction with cancer cells. Immature DCs facilitate tolerance toward cancer cells (observed for many apoptotic inducers) while fully mature DCs can strongly promote anticancer immunity if they secrete the correct combinations of cytokines [observed when DCs interact with cancer cells undergoing immunogenic cell death (ICD)]. However, an intermediate population of DC maturation, called semi-mature DCs exists, which can potentiate either tolerogenicity or pro-tumorigenic responses (as happens in the case of certain chemotherapeutics and agents exerting ambivalent immune reactions). Specific combinations of DC phenotypic markers, DC-derived cytokines/chemokines, dying cancer cell-derived danger signals, and other less characterized entities (e.g., exosomes) can define the nature and evolution of the DC maturation state.

The initial reaction orchestrated by innate immune cells consists of capturing, as well as clearing up or destroying the source of injury, infection, or diseased cells, followed by wound healing and if required (in case of well discernable antigens) "priming" of the adaptive immune cells against antigens derived from the "non-self" diseased cells or pathogens. This adaptive immune cell priming helps to initiate more specific responses, directed against the acquired antigens and leading to the eradication of the antigen source.

This in principle is also the basic theory behind anticancer immunity or anticancer immunosurveillance, where innate immune cells recognize the "non-self" tumor-associated antigens (TAAs) and prime adaptive immune cells (mainly T cells) against them. This leads to both: direct and indirect cancer killing, anticancer effector functions, production of anti-TAA antibodies and subsequent immunity capable of rejecting tumor cells possessing the corresponding TAAs. In this complex interplay, one may appreciate that the step of "priming" adaptive immune cells by innate immune cells against TAAs represents a crucial milestone that is completely dependent on the antigen-presenting and antigen-sensing capabilities of innate immune cells. While most innate immune cells (professional presenters) and certain cells of epithelial lineage (non-professional presenters) are capable of presenting antigens to the adaptive immune cells be it to varying degrees; yet the sentinel antigen-presenting cells (APCs) of the immune system are the DCs. DCs are the guardian APCs because they are both efficient at antigen-presenting and adaptive immune cell activation and also good at judging whether an entity possesses "self" or "non-self" antigens. The ability of DCs to present "non-self" TAAs properly to prime as well as to activate adaptive immune cells is an absolute pre-requisite for activation of potent anticancer immunity.

The disclosure provides that the antigenic ICV producing cells disclosed herein are, as indicated above, are antigen presenting cells (e.g., dendritic cells). Alternatively, the ICV producing cells are cells that have been modified to present antigens, e.g., by use of expression vectors, gene therapy, and the like. For example, tumor cells can be forced to present their own tumor antigens to the immune system, by use of expression vectors and gene therapy. Generation of dendritic cells is known in the art and may be performed according to methods described and incorporated by reference, specifically methodologies have been described for DCs generation, in which the DCs have been used in clinical trials of the following cancers: melanoma, soft tissue sarcoma, thyroid, glioma, multiple myeloma, lymphoma, leukemia, as well as liver, lung, ovarian, and pancreatic cancer.

In the studies provided herein, the ability of producer cells to secrete ICVs was exploited. DC cells were induced to undergo blebbing by use of a method disclosed herein. It was discovered that the size of generated antigenic ICVs were largely in the nanometer or micrometer size range (e.g., from 0.2 μm to 10 μm). Further, it was shown herein that the methods of the disclosure efficiently produced nanometer/micrometer antigenic ICVs without the need to add other chemical agents, like reducing agents (e.g., DTT). The foregoing is especially beneficial as the studies presented herein indicate that the use of DTT negatively affected antigen presentation of antigenic ICVs presented herein.

The antigenic ICVs disclosed herein can be used in immunotherapy applications, whereby administration of the antigenic ICVs can promote or induce a desired immune response in a subject in need of immunotherapy. For example, the antigenic ICVs disclosed herein represent an improved platform for cancer immunotherapy by being scalable, tunable size, tunable maturation rate, and having a cell-free aspect. More specifically, the disclosure provides a cell-free antigenic ICV-based immunotherapy that was developed by isolating ICVs (e.g., mICVs or nICVs) from antigen-presenting dendritic cells harvested from bone marrow (BMDCs). By inducing cell membrane blebbing by using a sulfhydryl-blocking agent or p photosensitizer, antigen-presenting ICVs were produced from mature BMDCs that expressed CD11c, CD40, CD80, CD86 and H-2Kb bound to SIINFEKL. The antigenic ICVs of the disclosure demonstrated effective activation of T cell hybridomas in vitro and cytotoxic T lymphocytes in vivo. Immunization with cell-free antigenic ICVs derived from mature BMDCs resulted in slowed tumor growth and improved survival outcomes comparable to whole cell therapy. While the exemplary study presented herein used immunization against OVA-expressing cancer cells, it should be recognized that antigenic ICVs can be engineered to present specific cancer antigens and therefore have a range of potential for various types of cancer therapy. Moreover, the antigenic ICVs disclosed herein can be used for suppression immunotherapies to dampen an abnormal immune response in autoimmune diseases or reduces a normal immune response to prevent rejection of transplanted organs or cells. Additionally, there is potential to develop antigenic ICVs as vaccines against infectious diseases, and as helminthic therapies.

The disclosure teaches means of utilizing antigenic ICVs for cancer immunotherapy. In one embodiment, the disclosure provides generation of therapeutic immune stimulating antigenic ICVs through the steps of: (a) obtaining immature dendritic cells (e.g., bone marrow dendritic cells (BMDCs)); (b) pulsing dendritic cells with an antigen associated with cancer cells; (c) inducing cell membrane blebbing by use of a sulfhydryl blocking agent or a photosensitizer; (d) collecting antigenic ICVs that are produced from cell membrane blebbing; and (d) administering said antigenic ICVs to a subject in need of immunotherapy. In one embodiment said dendritic cells (DCs) are pulsed with antigen in the form of protein, peptide, altered peptide, or DNA or RNA transfection. Cancer associated proteins may be utilized for pulsing of DCs include, but are not limited to, oncogenic proteins, such as EGFRvIII, EGFR, HER-2, HER-3, HER-4, MET, cKit, PDGFR, Wnt, beta-catenin, K-ras, H-ras, N-ras, Raf, N-myc, c-myc, IGFR, IGFR, PI3K, and Akt; tumor suppressor proteins, such as BRCA1, BRCA2 and PTEN; cancer-related host receptors and proteins associated with angiogenesis such as VEGFR-2, VEGFR-1, Tie-2, TEM-1 and CD276. It is contemplated that all oncogenic proteins, tumor suppressor proteins, host-cell related receptors and microvesicle-associated molecules may be used, alone or in combination, in the methods, compositions and kits of the present disclosure. It is further contemplated that any oncogenic protein, and any combination of oncogenic proteins, which is determined to be mechanistically, diagnostically, prognostically or therapeutically important for cancer, may be used in the methods, compositions and kits of the present disclosure.

The disclosure further provides methods of delivering the ICVs disclosed herein to a subject in need of immunotherapy comprising, administering an effective amount of an antigenic ICV preparation or ICV preparation produced by a method disclosed herein to the subject. The administering can be local or systemic. For example, the antigenic ICV preparation or ICV preparation may be locally administered to a subject by injection, such as by injection into an organ or a tumor.

The disclosure also provides methods of elucidating an immune response in an immune cell, comprising: contacting the immune cell with an effective amount of an antigenic ICV preparation produced by a method disclosed herein. In one embodiment, the immune cell is contacted in vivo. In a further embodiment, the immune cell is contacted within an organ or tumor. In yet a further embodiment, the antigenic ICV preparation is produced ex vivo from donor cells of a subject. In an alternate embodiment, the immune cell is contacted in vitro with antigenic ICV preparation.

In view of the foregoing, the methods disclosed in the application provide a foundational platform for the production of ICVs that can be rapidly and mass produced, and further, can be designed and tailored for use in specific applications such as for drug delivery, gene therapy, immunotherapy, cell-free cell therapy, and molecular therapy, and that such advantages cannot be recognized using currently available techniques. For example, by using an engineering biology approach, one can design ICVs that are customized with various surface proteins and/or cargoes to treat specific diseases or conditions.

In a particular embodiment, ICVs described herein can be used to deliver therapeutic molecules (e.g., gene therapy components, antisense oligonucleotide, small molecule therapeutics, etc.) to a target cell or population of cells. Delivery is accomplished from contacting of the ICVs to the target cells (e.g., tumor cells) or tissue. The target cells or tissue may be contacted in vitro or in vivo. In vivo delivery is accomplished by administration of the ICVs described herein to a subject by a route that results in contacting of the ICVs with the target cells or tissue. For therapeutic purposes, a therapeutically effective amount is administered such that an effective amount of the therapeutic molecule is delivered to the target cells or tissue. In a further embodiment, the targeted cell or tissue is contacted within an organ or tumor. In yet a further embodiment, the ICVs described herein are produced ex vivo from donor cells of a subject that is to be treated. In an alternate embodiment, the targeted cell or tissue is contacted in vitro. The ICVs can be loaded with different types of therapeutic molecules, including small molecule drugs, biological molecules, viruses, therapeutic agents, prodrugs, gene silencing agents, chemotherapeutics, diagnostic agents, and/or components of gene editing systems. Examples of biological molecules include, but are not limited to, nucleic acids (e.g., DNA, RNA, mRNA, modified mRNA, small RNAs, siRNA, miRNA, genes, and transgenes), peptides/proteins (including antibodies, enzymes, transcription factors, etc.), viruses, hormones, carbohydrates, lipids, and vitamins. Examples of gene silencing agents, include siRNA, chRNAs, miRs, ribozymes, morpholinos, and esiRNAs. Examples of gene editing systems include, but are not limited to, CRISPR-Cas systems, zinc finger nucleases, and TALENs. Examples of diagnostic agents, include but are not limited to, dyes and stains, radioactive tracers, and contrast agents.

In a particular embodiment, the ICVs are loaded with one or more small molecule therapeutic compounds or agents. In a further embodiment, the ICVs are loaded or co-administered with one or more anticancer agents or chemotherapeutics. Examples, of anticancer agents and chemotherapeutics that can be used with or loaded into the ICVs disclosed herein include, but are not limited to, alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and tiimethylolomelamine; acetogenins (e.g., bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; vinca alkaloids; epipodophyllotoxins; antibiotics such as the enediyne antibiotics (e.g., calicheamicin, especially calicheamicin gammall and calicheamicin omegall; L-asparaginase; anthracenedione substituted urea; methyl hydrazine derivatives; dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitiaerine; pentostatin; phenamet; pirarubicin; losoxantione; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2 2"-trichlorotiiethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® (docetaxel) (Rhone-Poulenc Rorer, Antony, France); chloranbucil; GEMZAR® (gemcitabine); 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (e.g., CPT-11); topoisomerase inhibitor RFS 2000; difluoromethylornithine (DFMO); retinoids such as retinoic acid; capecitabine; leucovorin (LV); irenotecan; adrenocortical suppressant; adrenocorticosteroids; progestins; estrogens; androgens; gonadotropin-releasing hormone analogs; and pharmaceutically acceptable salts, acids or derivatives of any of the above. Also included anticancer agents are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON-toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASL® exemestane, formestanie, fadrozole, RIVISOR® vorozole, FEMARA® letrozole, and ARTMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF-A expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® rJL-2; LURTOTECAN® topoisomerase 1 inhibitor; ABARELLX® rmRH; antibodies such as trastuzumab and pharmaceutically acceptable salts, acids or derivatives of any of the above.

The disclosure further provides that the ICVs disclosed herein may be used to deliver biological molecules, therapeutic agents, prodrugs, gene silencing agents, chemotherapeutics, diagnostic agents, gene therapy agents and/or components of a gene editing system to a subject, or cells thereof. Delivery of the biological molecule may elicit a desired effect directly, such as an mRNA encoding a peptide for immediate transcription. Alternatively, delivery of the biological molecule may cause the desired tissue to generate the response, such that delivery of a transcription factor may activate an innate gene. Delivery of specific imaging agents may allow accumulation of dyes to a specific cell-type or tissue for imaging without background imaging signal being produced by neighboring tissue (e.g., FRET sensing applications).

The disclosure also provides that the ICVs disclosed herein which comprise a cargo, e.g., biological molecules, therapeutic agents, prodrugs, gene silencing agents, chemotherapeutics, diagnostic agents, and/or components of a gene editing system, prior to, concurrently with, after, or any combination thereof for the production of cargo loaded ICVs. For example, ICV producing cells may be loaded with the cargo, or alternatively the ICV producing cells may be induced to produce cargo like biomolecules. In embodiments where the ICV producing cells are loaded with the cargo, the cells may be incubated with the cargo in similar conditions as described within this disclosure or in the art to allow for the cell to uptake the cargo (e.g., therapeutic agents) (e.g., see Pascucci et al., *J. Control. Release* 2014, 192, 262-270; Lv et al., *J. Biol. Chem.* 2012, 287, 15874-15885, and US20180296483). In embodiments where the cells are loaded by inducing a cell to produce the cargo (i.e., biomolecules), the cell may be engineered to express or produce specific peptides, nucleic acids, or both peptides and nucleic acids with therapeutic properties (e.g., see Tian et al., *Biomaterials* 2014 35(7):2383-90). Therapeutic peptides may include small peptides, protein subunits, entire proteins, or any combination of the above. Therapeutic nucleic acids may include DNA or RNA, including genie sequences, plasmid DNA, tRNA, rRNA, mRNA, small RNAs, miRNA, siRNA, shRNA, crRNA, or any combination of nucleic acids produced within the cell. Additionally, ribonucleoproteins or any other form of protein-nucleic acid complex may be produced within a cell. In some embodiments, once the cells are loaded with the cargo, cell blebbing as described herein is used to induce cell vesicle formation. In other embodiments, cell blebbing may be induced during the loading of the cargo into the cells. Situations were cell blebbing may occur during loading may include where the cell produces the cargo (i.e., biomolecules). Upon inducing cell blebbing, ICVs produced from the cargo loaded cells may contain the agents of interest.

ICVs produced in accordance with embodiments of the disclosure may also be loaded with the cargo via direct membrane penetration, chemical labeling and conjugation, electrostatic coating, adsorption, absorption, sonification, electroporation, use of pH gradients, or any combination thereof. For example, the ICVs can be loaded by sonification by the methods described in Kim et al. (*Nanomedicine* 2016 12(3):6550664). In another embodiment, the cargo can be loaded in ICVs by use of a pH gradient between the inside of and the outside of the ICV, e.g., (i) increasing or decreasing the pH value inside of the ICV and/or (ii) increasing or decreasing the pH value outside of the ICV (e.g., see US20180177725). Methods of formulating the pH gradient between the inside of and the outside of the vesicle composition are known to the skilled artisan.

Further, ICVs produced in accordance with certain embodiments of the disclosure may undergo multiple loading steps, such that some cargo may be loaded prior to cell blebbing, while additional cargo may be loaded during or after cell blebbing. Additionally, ICVs may be loaded with the cargo during cell blebbing, and further loaded with another cargo after cell blebbing. In a further embodiment, the ICVs may be loaded with a cargo as defined above by incubating the ICV producing cells or empty ICVs with a cargo as defined above having the concentration of 25 pg/mL, 50 pg/mL, 100 pg/mL, 200 pg/mL, 300 pg/mL, 400 pg/mL, 500 pg/mL, 600 pg/mL, 700 pg/mL, 800 pg/mL, 900 pg/ml, 1 ng/mL, 10 ng/mL, 100 ng/mL, 1 µg/mL, 10 ug/mL or any range that includes or is between any two of the foregoing concentrations, including fractional increments thereof Additionally, the incubation with the cargo may occur for 1 hour, 2 hours, 3 hours, 4 hours, 5 hours, 6 hours, 12 hours, 24 hours, 48 hours, or any range that includes or is between any two of the foregoing time points, including fractional increments thereof. Alternatively, the loading conditions may occur at a ratio of ICVs to a cargo as defined above of 1:20 to 20:1, 1:15 to 15:1, 12:1 to 1:12, 11:1 to 1:11, 10:1 to 1:10, 9:1 to 1:9, 8:1 to 1:8, 7:1 to 1:7, 6:1 to 1:6, 5:1 to 1:5, 4:1 to 1:4, 3:1 to 1:3, 2:1 to 1:2, 1.5:1 to 1:1.5, or 1:1. Additionally, the polydispersity of cargo-loaded ICVs may have a similar polydispersity index (PDI) as unloaded ICVs. As such, cargo-loaded ICVs may have a PDI of about 0.1, 0.2, 0.3, 0.4, 0.5, 0.6, 0.7, 0.8, 0.9, 1.0, or any range that includes or is between any two of the foregoing values, including fractional increments thereof.

In a further embodiment, a composition, such as a pharmaceutical composition, preparation or formulation may comprise a plurality of different types of ICVs, that differ, e.g., in size, cargo, recombinant modifications or originate from different ICV producing cells. For example, the composition may comprise antigenic ICVs; and ICVs that are loaded with a therapeutic cargo, such as anticancer agents, or gene therapy components. Such gene therapy components are described more fully below, but can include AAVs that express a transgene (e.g., a tumor suppressor gene, pro-apoptosis gene, etc.). Any number of combinations of different types of ICVs are possible using the methods disclosed herein. The disclosure further provides that the ICVs made by the methods disclosed herein can be used for cell-free cell therapies. For example, antigenic ICVs disclosed herein can be used as cell-free versions of the immunotherapy approach of adoptive cell transfer (ACT). In such a case, immune cells (mammalian T cells, DC cells, NK cells, neutrophils, macrophages, and stem cells (iPSCs included)) are first extracted from the patient, genetically modified, and cultured in vitro; then these cells are used to produce ICVs using the methods disclosed herein and the ICVs are administered to the same patient. The most well known and advanced form of ACT is CAR T-cell therapy. As such, it is envisioned that the antigenic ICVs disclosed herein can be used as cell-free version of CAR T-cell therapy. Additionally, any cell-free cell therapy that uses exosomes can similarly use ICVs. Examples of such cell-free cell therapies, include use of ICVs include to suppress T-cell activity by expressing PD-L1 (e.g., see Poggio et al., Cell 177(2):P414-427); use of ICVs to inhibit tumor growth and increase T cell infiltration by expressing a hyaluronidase (e.g., see Hong et al., *Advanced Functional Materials* 28(5) (2018)); use of ICVs to redirect and activate cytotoxic T cells toward cancer cells by displaying antibodies to CD3 and EGFR using an anchoring motif (e.g., see Cheng et al., Journal of American Chemical Society 140:16413:16417 (2018)). Additionally, the ICVs disclosed herein can be used as cell-free vaccines. Such ICVs can be loaded with biomolecules (e.g., mRNA, DNA, proteins, etc.) that provide active acquired immunity to a particular disease or condition when the ICVs are administered. Such vaccines can be used to treat diseases caused by infectious agents, like disease causing bacteria, viruses, and protozoa; or used as therapies to treat cancer, herpes, HIV and Alzheimer's disease. Further, the ICVs disclosed herein can be designed to be multifunctional therapeutic cell free scaffolds, such that they can be used to have multiple and synergistic biological effects when administered, e.g., the ICVs be loaded with multiple types of cargo to treat the same disease or disorder; may have a cargo that works in conjunction with a cell surface modification to treat a disease or disorder; may have multiple cell surface modifications that activate multiple cell types in treating a disease or disorder; etc.

The disclosure further provides for pharmaceutical compositions, preparation or formulations comprising an ICV preparation described herein for specified modes of administration. In one embodiment, an ICV preparation described herein is an active ingredient in a composition comprising a pharmaceutically acceptable carrier. Such a composition is referred to herein as a pharmaceutical composition. A "pharmaceutically acceptable carrier" means any pharmaceutically acceptable means to mix and/or deliver the targeted delivery composition to a subject. The term "pharmaceutically acceptable carrier" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the composition and is compatible with administration to a subject, for example a human. Such compositions can be specifically formulated for administration via one or more of a number of routes, such as the routes of administration described herein. Supplementary active ingredients also can be incorporated into the compositions. When an agent, formulation or pharmaceutical composition described herein, is administered to a subject, preferably, a therapeutically effective amount is administered. As used herein, the term "therapeutically effective amount" refers to an amount that results in an improvement or remediation of the condition.

Administration of the pharmaceutical composition to a subject is by means which an ICV preparation contained therein will contact the target cell. The specific route will depend upon certain variables such as the target cell and can be determined by the skilled practitioner. Suitable methods of administering an ICV preparation described herein to a patient include any route of in vivo administration that is suitable for delivering extracellular vesicles to a patient. The preferred routes of administration will be apparent to those of skill in the art, depending on the extracellular vesicle preparation's type of therapeutic molecule used, the target cell population, and the disease or condition experienced by the subject. Preferred methods of in vivo administration include, but are not limited to, intravenous administration, intertumoral administration, intraperitoneal administration, intramuscular administration, intracoronary administration, intraarterial administration (e.g., into a carotid artery), subcutaneous administration, transdermal delivery, intratracheal administration, subcutaneous administration, intraarticular administration, intraventricular administration, inhalation (e.g., aerosol), intracerebral, nasal, oral, pulmonary administration, impregnation of a catheter, and direct injection into a tissue. In an embodiment where the target immune cells are in or near a tumor, a preferred route of administration is by direct injection of antigenic ICVs into the tumor or tissue surrounding the tumor. For example, when the tumor is a breast tumor, the preferred methods of administration include impregnation of a catheter, and direct injection of antigenic ICVs into the tumor.

Intravenous, intraperitoneal, and intramuscular administrations can be performed using methods standard in the art. Aerosol (inhalation) delivery can also be performed using methods standard in the art (see, for example, Stribling et al., *Proc. Natl. Acad. Sci. USA* 189: 11277-11281, 1992, which is incorporated herein by reference in its entirety). Oral delivery can be performed by complexing an ICV preparation of the disclosure to a carrier capable of withstanding degradation by digestive enzymes in the gut of an animal. Examples of such carriers, include plastic capsules or tablets, such as those known in the art.

One method of local administration is by direct injection. Direct injection techniques are particularly useful for administering ICVs to a cell or tissue that is accessible by surgery, and particularly, on or near the surface of the body. Administration of a composition locally within the area of a target cell refers to injecting the composition centimeters and preferably, millimeters from the target cell or tissue.

The appropriate dosage and treatment regimen for the methods of treatment described herein will vary with respect to the particular disease being treated, the ICVs being delivered, and the specific condition of the subject. The skilled practitioner is to determine the amounts and frequency of administration on a case by case basis. In one embodiment, the administration is over a period of time until the desired effect (e.g., reduction in symptoms is achieved). In a certain embodiment, administration is 1, 2, 3, 4, 5, 6, or 7 times per week. In a particular embodiment, administration is over a period of 1, 2, 3, 4, 5, 6, 7, 8, 9, or 10 weeks. In another embodiment, administration is over a period of 2, 3, 4, 5, 6 or more months. In yet another embodiment, treatment is resumed following a period of remission.

For use in the therapeutic applications described herein, kits and articles of manufacture are also described herein. Such kits can comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers can be formed from a variety of materials such as glass or plastic.

For example, the container(s) can comprise one or more ICV preparations described herein, optionally in a composition or in combination with another agent as disclosed herein. The container(s) optionally have a sterile access port (for example the container can be an intravenous solution bag or a vial having a stopper pierceable by a hypodermic injection needle). Such kits optionally comprise a compound disclosed herein with an identifying description or label or instructions relating to its use in the methods described herein.

A kit will typically comprise one or more additional containers, each with one or more of various materials (such as reagents, optionally in concentrated form, and/or devices) desirable from a commercial and user standpoint for use of a compound described herein. Non-limiting examples of such materials include, but are not limited to, buffers, diluents, filters, needles, syringes; carrier, package, container, vial and/or tube labels listing contents and/or instructions for use, and package inserts with instructions for use. A set of instructions will also typically be included.

A label can be on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific application. The label can also indicate directions for use of the contents, such as in the methods described herein.

The disclosure further provides that the methods and compositions described herein can be further defined by the following aspects (aspects 1 to 90):

1. A method to produce induced cell vesicles (ICVs) or antigenic ICVs, comprising:
inducing cell vesicle production from cells by exposing or contacting the cells with a cell blebbing buffer which comprises a sulfhydryl blocking agent or a photosensitizer wherein antigenic ICVs are produced from antigen presenting cells which can stimulate T-cell activation.

2. The method of aspect 1, wherein the cells are from a mammal.

3. The method of aspect 1 or 2, wherein the cells are from a human.

4. The method of any one of the previous aspects, wherein the cells are from a human patient that has a disorder or disease that is to be treated with ICVs or antigenic ICVs produced therefrom.

5. The method of any one of the previous aspects, wherein the cells are selected from epithelial cells, fibroblast cells, tumor cells, mast cells, T and B lymphocytes, dendritic cells, and Langerhans cells.

6. The method of any one of the previous aspects, wherein the antigenic ICVs are produced from dendritic cells, preferably wherein the dendritic cells are conventional dendritic cells and/or plasmacytoid dendritic cell, more preferably wherein the dendritic cells are CD11c+ myeloid dendritic cells, CD 141+ myeloid dendritic cells, and/or CD 303+ plasmacytoid dendritic cells.

7. The method of aspect 6, wherein the dendritic cells are bone marrow dendritic cells (BMDCs).

8. The method of aspect 7, wherein the BMDCs are immature BMDCs, preferably wherein the immature BMDCs express CD11c surface markers.

9. The method of aspect 7, wherein the BMDCs are mature BMDCs, preferably wherein the mature BMDCs express CD80, CD83, and/or CD86 surface markers.

10. The method of any one of the previous aspects, wherein the induced cell vesicles comprise viruses, viral particles, or viral vectors, by being produced from cells comprising the same.

11. The method of aspect 10, wherein the viruses, viral particles, or viral vectors are selected from recombinant retroviruses, adenoviruses, adeno-associated viruses (AAV), alphaviruses, and lentiviruses.

12. The method of aspect 11, wherein the viruses, viral particles, or viral vectors are AAV, preferably wherein the AAV has serotype selected from AAV1, AAV2, AAV3, AAV4, AAV5, AAV6, AAV7, AAV8, AAV9, AAV10, AAV11, or AAV12, more preferably where the AAV is AAV2 or AA8.

13. The method of aspect 12, wherein the AAV expresses a heterologous transgene that is used for gene therapy, preferably wherein the heterologous transgene expresses a fully functioning gene product that is not expressed, misexpressed or mutated in a subject as a result of an inherited disorder or as a result of organ damage, more preferably wherein the heterologous transgene expresses Factor IX, RPE65, lipoprotein lipase, SCID-X1, IL2RG, telomerase, sarcoplasmic calcium ATPase, $Ca^{2+}$ channel-binding domain 3, or angiotensin-converting enzyme 2 gene products.

14. The method of any one of the previous aspects, wherein the cell blebbing buffer does not contain any small molecule redox reagents or reducing agents, preferably wherein the cell blebbing buffer does not contain dithiothreitol (DTT).

15. The method of any one of the previous aspects, wherein the cell blebbing buffer comprises a buffered balanced salt solution.

16. The method of aspect 15, wherein the buffered balanced salt solution selected from the group consisting of phosphate-buffered saline (PBS), Dulbecco's Phosphate-buffered saline (DPBS), Earle's Balanced Salt solution (EBSS), Hank's Balanced Salt Solution (HBSS), TRIS-buffered saline (TBS), and Ringer's balanced salt solution (RBSS).

17. The method of aspect 15, wherein the cell blebbing buffer comprises 0.5×, 0.6×, 0.7×, 0.8×, 0.9×, 1×, 2×, 3×, 4×, 5×, 6×, 7×, 8×, 9×, or 10× concentration/dilution of the buffered balanced salt solution, or a range that includes or is between any two of the foregoing concentrations/dilutions, including fractional values thereof, preferably wherein the cell blebbing buffer comprises a concentration/dilution of the buffered balanced salt solution, preferably wherein the cell blebbing buffer comprises 1× to 10× concentration/dilution of the buffered balanced salt solution.

18. The method of aspect 15, wherein the cell blebbing buffer comprises 1× to 5×, 1× to 4×, 1× to 3×, 1× to 2×, 2× to 5×, 2× to 4×, 2× to 3×, 3× to 5×, or 3× to 4×, concentration/dilution of the buffered balanced salt solution, preferably wherein the buffered balanced salt solution is DPBS.

19. The method of any one of the previous aspects, wherein the cells are incubated in the cell blebbing buffer which comprises a sulfhydryl blocking agent for 0.5 h, 1 h, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h, 36 h, 48 h, 72 h or a range that includes or is between any two of the foregoing time points, including fractional values thereof, more preferably wherein the cells are incubated in the cell blebbing buffer which comprises a sulfhydryl blocking agent for 1 h to 10 h, 2 h to 10 h, 3 h to 10 h, 4 h to 10 h, 5 h to 10 h, 6 h to 10 h, 7 h to 10 h, 8 h to 10 h, 1 h to 9 h, 2 h to 9 h, 3 h to 9 h, 4 h to 9 h, 5 h to 9 h, 6 h to 9 h, 7 h to 9 h, 8 h to 9 h, 1 h to 8 h, 2 h to 8 h, 3 h to 8 h, 4 h to 8 h, 5 h to 8 h, 6 h to 8 h, 7 h to 8 h, 1 h to 7 h, 2 h to 7 h, 3 h to 7 h, 4 h to 7 h, 5 h to 7 h, or 6 h to 7 h.

20. The method of aspect 19, wherein the cells are incubated in the cell blebbing buffer for 1 h to 8 h at about 37° C.

21. The method of any one of the previous aspects, wherein the sulfhydryl blocking agent is selected from the group consisting of and N-ethylmaleimide, paraformaldehyde, mercury chloride, p-chloromercuribenzene sulfonic acid, auric chloride, p-chloromercuribenzoate, chlormerodrin, meralluride sodium, and iodoacetamide.

22. The method of aspect 21, wherein the sulfhydryl blocking agent is N-ethylmaleimide (NEM) or maleimide.

23. The method of aspect 22, wherein the cell blebbing buffer comprises NEM at a concentration of 0.5 mM, 0.6 mM, 0.7 mM, 0.8 mM, 0.9 mM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.1 mM, 2.2 mM, 2.3 mM, 2.4 mM, 2.5 mM, 2.6 mM, 2.7 mM, 2.8 mM, 2.9 mM, 3.0 mM, 3.1 mM, 3.2 mM, 3.3 mM, 3.4 mM, 3.5 mM, 3.6 mM, 3.7 mM, 3.8 mM, 3.9 mM, 4.0 mM, 4.1 mM, 4.2 mM, 4.3 mM, 4.4 mM, 4.5 mM, 4.6 mM, 4.7 mM, 4.8 mM, 4.9 mM, 5.0 mM, 6.0 mM, 7.0 mM, 8.0 mM, 9.0 mM, 0.01 M, 0.1 M, 1.0 M, 1.5 M, 2.0 M, or a range that includes or is between any two of the foregoing concentrations, preferably wherein the cell blebbing buffer comprises NEM at a concentration of
1 mM to 10 mM, 1 mM to 9 mM, 1 mM to 8 mM, 1 mM to 7 mM, 1 mM to 6 mM, 1 mM to 5 mM, 1 mM to 4 mM, 1 mM to 3 mM, 1 mM to 2 mM, 2 mM to 10 mM, 2 mM to 9 mM, 2 mM to 8 mM, 2 mM to 7 mM, 2 mM to 6 mM, 2 mM to 5 mM, 2 mM to 4 mM, 2 mM to 3 mM, 3 mM to 10 mM, 3 mM to 9 mM, 3 mM to 8 mM, 3 mM to 7 mM, 3 mM to 6 mM, 3 mM to 5 mM, 3 mM to 4 mM, 4 mM to 10 mM, 4 mM to 9 mM, 4 mM to 8 mM, 4 mM to 7 mM, 4 mM to 6 mM, or 4 mM to 5 mM, more preferably wherein the cell blebbing buffer comprises NEM at a concentration from 1 mM to 10 mM.

24. The method of aspect 23, wherein the cell blebbing buffer consists essentially of 1 mM, 1.5 mM, 2 mM, 2.5 mM, or 3 mM NEM in DPBS, preferably wherein the cell blebbing buffer consists essentially of 2 mM NEM in DPBS.

25. The method of aspect 21, wherein the cell blebbing buffer comprises paraformaldehyde.

26. The method of aspect 25, wherein the cell blebbing buffer comprises paraformaldehyde at a concentration of 10.0 mM, 12.0 mM, 14.0 mM, 15.0 mM, 16.0 mM, 18.0 mM, 20.0 mM, 21.0 mM, 22.0 mM, 23.0 mM, 24.0 mM, 25.0 mM, 26.0 mM, 27.0 mM, 28.0 mM, 29.0 mM, 30.0 mM, 32.0 mM, 34.0 mM, 35.0 mM, 40.0 mM, 45.0 mM, 50.0 mM, 100.0 mM, 200.00 mM or a range that includes or is between any two of the foregoing concentrations, including fractional values thereof, preferably wherein the cell blebbing buffer comprises paraformaldehyde at a concentration of 10.0 mM to 50.0 mM, 10.0 mM to 45.0 mM, 10.0 mM to 40.0 mM, 10.0 mM to 35.0 mM, 10.0 mM to 34.0 mM, 10.0 mM to 33.0 mM, 10.0 mM to 32.0 mM, 10.0 mM to 31.0 mM, 10.0 mM to 30.0 mM, 10.0 mM to 29.0 mM, 10.0 mM to 28.0 mM, 10.0 mM to 27.0 mM, 10.0 mM to 26.0 mM, 10.0 mM to 25.0 mM, 15.0 mM to 50.0 mM, 15.0 mM to 45.0 mM, 15.0 mM to 40.0 mM, 15.0 mM to 35.0 mM, 15.0 mM to 34.0 mM, 15.0 mM to 33.0 mM, 15.0 mM to 32.0 mM, 15.0 mM to 31.0 mM, 15.0 mM to 30.0 mM, 15.0 mM to 29.0 mM, 15.0 mM to 28.0 mM, 15.0 mM to 27.0 mM, 15.0 mM to 26.0 mM, 15.0 mM to 25.0 mM, 18.0 mM to 40.0 mM, 18.0 mM to 35.0 mM, 18.0 mM to 34.0 mM, 18.0 mM to 33.0 mM, 18.0 mM to 32.0 mM, 18.0 mM to 31.0 mM, 18.0 mM to 30.0 mM, 18.0 mM to 29.0 mM, 18.0 mM to 28.0 mM, 18.0 mM to 27.0 mM, 18.0 mM to 26.0 mM, 18.0 mM to 25.0 mM, 20.0 mM to 34.0 mM, 20.0 mM to 33.0 mM, 20.0 mM to 32.0 mM, 20.0 mM to 31.0 mM, 20.0 mM to 30.0 mM, 20.0 mM to 29.0 mM, 20.0 mM to 28.0 mM, 20.0 mM to 27.0 mM, 20.0 mM to 26.0 mM, or 20.0 mM to 25.0 mM, more preferably wherein the cell blebbing buffer comprises 25 mM of paraformaldehyde.

27. The method of any one of the previous aspects, wherein the cells are incubated with or exposed to a photosensitizer having a concentration of 0.1 ug/mL, 0.2 ug/mL, 0.3 ug/mL, 0.4 ug/mL, 0.5 ug/mL, 0.6 ug/mL, 0.7 ug/mL, 0.8 ug/mL, 0.9 ug/mL, 1.0 ug/mL, 1.1 ug/mL, 1.2 ug/mL, 1.3 ug/mL, 1.4 ug/mL, 1.5 ug/mL, 1.6 ug/mL, 1.7 ug/mL, 1.8 ug/mL, 1.9 ug/mL, 2.0 ug/mL, 2.5 ug/mL, 3.0 ug/mL, 3.5 ug/mL, 4.0 ug/mL, 4.5 ug/mL, 5.0 ug/mL, 10.0 ug/mL or a range that includes or is between any two of the foregoing concentrations, including fractional values thereof, preferably wherein the cells are incubated with or exposed to a photosensitizer having a concentration of 0.1 ug/mL to 5.0 ug/mL, 0.1 ug/mL to 4.5 ug/mL, 0.1 ug/mL to 4.0 ug/mL, 0.1 ug/mL to 3.5 ug/mL, 0.1 ug/mL to 3.0 ug/mL, 0.1 ug/mL to 2.5 ug/mL, 0.1 ug/mL to 2.0 ug/mL, 0.1 ug/mL to 1.6 ug/mL, 0.1 ug/mL to 1.5 ug/mL, 0.1 ug/mL to 1.4 ug/mL, 0.1 ug/mL to 1.3 ug/mL, 0.1 ug/mL to 1.2 ug/mL, 0.1 ug/mL to 1.1 ug/mL, 0.3 ug/mL to 5.0 ug/mL, 0.3 ug/mL to 4.5 ug/mL, 0.3 ug/mL to 4.0 ug/mL, 0.3 ug/mL to 3.5 ug/mL, 0.3 ug/mL to 3.0 ug/mL, 0.3 ug/mL to 2.5 ug/mL, 0.3 ug/mL to 2.0 ug/mL, 0.3 ug/mL to 1.6 ug/mL, 0.3 ug/mL to 1.5 ug/mL, 0.3 ug/mL to 1.4 ug/mL, 0.3 ug/mL to 1.3 ug/mL, 0.3 ug/mL to 1.2 ug/mL, 0.3 ug/mL to 1.1 ug/mL, 0.5 ug/mL to 5.0 ug/mL, 0.5 ug/mL to 4.5 ug/mL, 0.5 ug/mL to 4.0 ug/mL, 0.5 ug/mL to 3.5 ug/mL, 0.5 ug/mL to 3.0 ug/mL, 0.5 ug/mL to 2.5 ug/mL, 0.5 ug/mL to 2.0 ug/mL, 0.5 ug/mL to 1.6 ug/mL, 0.5 ug/mL to 1.5 ug/mL, 0.5 ug/mL to 1.4 ug/mL, 0.5 ug/mL to 1.3 ug/mL, 0.5 ug/mL to 1.2 ug/mL, or 0.5 ug/mL to 1.1 ug/mL, more preferably wherein the cells are incubated with or exposed to a photosensitizer having a concentration of 0.5 ug/mL to 5.0 ug/mL.

28. The method of aspect 27, wherein the cells are incubated with or exposed to a photosensitizer having a concentration of 1.0 ug/mL.

29. The method of any one of the previous aspects, wherein the cells are exposed or incubated with the photosensitizer for 0.5 h, 1 h, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h, 36 h, 48 h, 72 h or a range that includes or is between any two of the foregoing time points, including fractional values thereof, more preferably wherein the cells are incubated with the photosensitizer for 1 h to 48 h, 2 h to 48 h, 4 h to 48 h, 6 h to 48 h, 8 h to 48 h, 10 h to 48 h, 12 h to 48 h, 14 h to 48 h, 16 h to 48 h, 18 h to 48 h, 20 h to 48 h, 22 h to 48 h, 24 h to 48 h, 1 h to 36 h, 2 h to 36 h, 4 h to 36 h, 6 h to 36 h, 8 h to 36 h, 10 h to 36 h, 12 h to 36 h, 14 h to 36 h, 16 h to 36 h, 18 h to 36 h, 20 h to 36 h, 22 h to 36 h, 24 h to 36 h, 1 h to 24 h, 2 h to 24 h, 4 h to 24 h, 6 h to 24 h, 8 h to 24 h, 10 h to 24 h, 12 h to 24 h, 14 h to 24 h, 16 h to 24 h, 18 h to 24 h, 20 h to 24 h, or 22 h to 24 h, preferably wherein the cells are incubated with the photosensitizer for 1 h to 48 h.

30. The method of aspect 29, wherein the cells are exposed to or incubated with the photosensitizer for 24 h at 37° C.

31. The method of any one of the previous aspects, wherein the photosensitizer is a porphyrin, chlorin or a dye.

32. The method of any one of the previous aspects, wherein the photosensitizer is selected from $AlPcS_{2A}$, $AlPcS_4$, lutrin, 5-aminolevulinic acid (ALA), hypericin, silicon phthalocyanine zinc (II) phthalocyanine (ZnPc), silicon phthalocyanine, mono-L-aspartyl chlorin e6, benzoporphyrin derivative monoacid ring A, chlorin photosensitizer tin etiopurpurin, tetra(m-hydroxyphenyl)chlorin, lutetium texaphyrin, 9-acetoxy-2,7,12,17-tetrakis-($\beta$-methoxyethyl)-porphycene, naphthalocyanines, Allumera®, Photofrin®, Visudyne®, Levulan®, Foscan®, Fospeg®, Metvix®, Hexvix®, Cysview® and Laserphyrin®, Antrin®, Photochlor®, Photosens®, Photrex®, Lumacan®, Cevira®, Visonac®, BF-200 ALA®, Amphinex® and Azadipyrromethenes.

33. The method of aspect 32, wherein the photosensitizer is $AlPcS_{2A}$.

34. The method of aspect 29, wherein the cells are washed with a buffered balanced salt solution one or more times, and taken up in the buffered balanced salt solution prior to exposure to light.

35. The method of aspect 34, wherein the buffered balanced salt solution selected from the group consisting of phosphate-buffered saline (PBS), Dulbecco's Phosphate-buffered saline (DPBS), Earle's Balanced Salt solution (EBSS), Hank's Balanced Salt Solution (HBSS), TRIS-buffered saline (TBS), and Ringer's balanced salt solution (RBSS).

36. The method of aspect 34, wherein the cells are taken up in 0.5×, 0.6×, 0.7×, 0.8×, 0.9×, 1×, 2×, 3×, 4×, 5×, 6×, 7×, 8×, 9×, or 10× concentration/dilution of the buffered balanced salt solution, or a range that includes or is between any two of the foregoing concentrations/dilutions, preferably wherein the cells are taken up in 1× to 10× concentration/dilution of the buffered balanced salt solution prior to light exposure.

37. The method of aspect 34, wherein the cells are taken up in 1×DPBS prior to light exposure.

38. The method of aspect 34, wherein the cells are exposed to light for 1 min, 2 min, 3 min, 4 min, 5 min, 6 min, 7 min, 8 min, 9 min, 10 min, 12 min, 14 min, 15 min, 16 min, 18 min, 20 min, 25 min, 30 min, 35 min, 40 min, 45 min, 50 min, 55 min, 60 min, 90 min, 120 min, or a range that includes or is between any two of the foregoing timepoints, including fractional values thereof, preferably wherein the cells are exposed to light for 1 min to 60 min, 1 min to 55 min, 1 min to 50 min, 1 min to 45 min, 1 min to 40 min, 1 min to 35 min, 1 min to 30 min, 1 min to 25 min, 1 min to 20 min, 1 min to 15 min, 1 min to 14 min, 1 min to 13 min, 1 min to 12 min, 1 min to 11 min, 1 min to 10 min, 2 min to 60 min, 2 min to 55 min, 2 min to 50 min, 2 min to 45 min, 2 min to 40 min, 2 min to 35 min, 2 min to 30 min, 2 min to 25 min, 2 min to 20 min, 2 min to 15 min, 2 min to 14 min, 2 min to 13 min, 2 min to 12 min, 2 min to 11 min, 2 min to 10 min, 5 min to 60 min, 5 min to 55 min, 5 min to 50 min, 5 min to 45 min, 5 min to 40 min, 5 min to 35 min, 5 min to 30 min, 5 min to 25 min, 5 min to 20 min, 5 min to 15 min, 5 min to 14 min, 5 min to 13 min, 5 min to 12 min, 5 min to 11 min, or 5 min to 10 min, more preferably wherein the cells are exposed to light for 1 min to 60 min.

39. The method of aspect 38, wherein the cells are exposed to light generated by a laser.

40. The method of aspect 39, wherein the cells are exposed to light having a wavelength
of 500 nm, 550 nm, 580 nm, 600 nm, 610 nm, 620 nm, 630 nm, 640 nm, 650 nm, 660 nm, 670 nm, 680 nm, 690 nm, 700 nm, 720 nm, 740 nm, 760 nm, 780 nm, 800 nm, 850 nm, 900 nm that is generated by a laser, or a range that includes or is between any two of the foregoing wavelengths, including fractional values thereof, preferably wherein the cells are exposed to light having a wavelength of 550 nm to 850 nm, 580 nm to 850 nm, 600 nm to 850 nm, 610 nm to 850 nm, 620 nm to 850 nm, 630 nm to 850 nm, 640 nm to 850 nm, 650 nm to 850 nm, 660 nm to 850 nm, 670 nm to 850 nm, 680 nm to 850 nm, 690 nm to 850 nm, 700 nm to 850 nm, 550 nm to 700 nm, 580 nm to 700 nm, 600 nm to 700 nm, 610 nm to 700 nm, 620 nm to 700 nm, 630 nm to 700 nm, 640 nm to 700 nm, 650 nm to 700 nm, 660 nm to 700 nm, or 670 nm to 700 nm, that is generated by a laser, more preferably wherein the cells are exposed to light having a wavelength from 600 nm to 850 nm that is generated by a laser.

41. The method of aspect 33, wherein the EB producing cells are incubated with or exposed to 1 ug/mL of $AlPcS_{2A}$ for 24 h at 37° C., washed multiple times in 1×DPBS, taken up in 1×DPBS, and then exposed to light generated from a 670 nm laser for 1 min to 10 min.

42. The method of any one of the previous aspects, wherein the method further comprises the step of:
purifying/isolating the ICVs or antigenic ICVs by using sucrose gradients.

43. The method of any one of the previous aspects, wherein the method further comprises the step of:
purifying/isolating the ICVs or the antigenic ICVs by:
(i) removing cellular debris by centrifugation from 1,000 rpm to 2,500 rpm for 1 to 10 minutes, preferably by centrifugation from 1,000 rpm to 2,000 rpm for 4 to 8 minutes, more preferably by centrifugation from 1,000 rpm to 1,500 rpm for 5 to 6 minutes; and
(ii) recovering the ICVs or antigenic ICVs by centrifugation using 10,000×g to 20,000×g for 5 to 15 minutes, preferably by centrifugation using 14,000×g to 18,000×g for 8 to 12 minutes, more preferably by centrifugation using 15,000×g to 17,000×g for 9 to 11 min;
optionally, concentrating the recovered nanometer sized ICVs or nanometer sized antigenic ICVs by using concentrators with a pore size cut-off from 50 to 150 kDA, preferably with a pore size cut-off of 100 kDA.

44. The method of aspect 43, wherein the isolated ICVs or isolated antigenic ICVs have average diameters of 10 nm, 20 nm, 30 nm, 40 nm, 50 nm, 60 nm, 70 nm, 80 nm, 90 nm, 100 nm, 110 nm, 120 nm, 130 nm, 140 nm, 150 nm, 160 nm, 170 nm, 180 nm, 190 nm, 200 nm, 250 nm, 300 nm, 350 nm, 400 nm, 450 nm, 500 nm, 550 nm, 600 nm, 650 nm, 700 nm, 750 nm, 800 nm, 850 nm, 900 nm, 950 nm, 1000 nm, 1100 nm, 1200 nm, 1300 nm, 1400 nm, 1500 nm, 1600 nm, 1700 nm, 1800 nm, 1900 nm, 2000 nm, 2500 nm, 3000 nm, 3500 nm, 4000 nm, 5000 nm, 6000 nm, 7000 nm, 8000 nm, 9000 nm, 10,000 nm or any range that includes or is between any two of the foregoing values, including fractional increments thereof, preferably the isolated ICVs or isolated antigenic ICVs have average diameters of 10 nm to 10,000 nm, 20 nm to 10,000 nm, 30 nm to 10,000 nm, 40 nm to 10,000 nm, 50 nm to 10,000 nm, 60 nm to 10,000 nm, 70 nm to 10,000 nm, 80 nm to 10,000 nm, 90 nm to 10,000 nm, 100 nm to 10,000 nm, 110 nm to 10,000 nm, 120 nm to 10,000 nm, 130 nm to 10,000 nm, 140 nm to 10,000 nm, 150 nm to 10,000 nm, 160 nm to 10,000 nm, 170 nm to 10,000 nm, 180 nm to 10,000 nm, 190 nm to 10,000 nm, 200 nm to 10,000 nm, 250 nm to 10,000 nm, 300 nm to 10,000 nm, 350 nm to 10,000 nm, 400 nm to 10,000 nm, 450 nm to 10,000 nm, 500 nm to 10,000 nm, 550 nm to 10,000 nm, 600 nm to 10,000 nm, 650 nm to 10,000 nm, 700 nm to 10,000 nm, 750 nm to 10,000 nm, 800 nm to 10,000 nm, 850 nm to 10,000 nm, 900 nm to 10,000 nm, 950 nm to 10,000 nm, 1000 nm to 10,000 nm, 10 nm to 5000 nm, 20 nm to 5000 nm, 30 nm to 5000 nm, 40 nm to 5000 nm, 50 nm to 5000 nm, 60 nm to 5000 nm, 70 nm to 5000 nm, 80 nm to 5000 nm, 90 nm to 5000 nm, 100 nm to 5000 nm, 110 nm to 5000 nm, 120 nm to 5000 nm, 130 nm to 5000 nm, 140 nm to 5000 nm, 150 nm to 5000 nm, 160 nm to 5000 nm, 170 nm to 5000 nm, 180 nm to 5000 nm, 190 nm to 5000 nm, 200 nm to 5000 nm, 250 nm to 5000 nm, 300 nm to 5000 nm, 350 nm to 5000 nm, 400 nm to 5000 nm, 450 nm to 5000 nm, 500 nm to 5000 nm, 550 nm to 5000 nm, 600 nm to 5000 nm, 650 nm to 5000 nm, 700 nm to 5000 nm, 750 nm to 5000 nm, 800 nm to 5000 nm, 850 nm to 5000 nm, 900 nm to 5000 nm, 950 nm to 5000 nm, or 1000 nm to 5000 nm, more preferably the isolated ICVs or isolated antigenic ICVs have average diameters from 10 nm to 10,000 nm.

45. The method of aspect 44, wherein the isolated ICVs or isolated antigenic ICVs have average diameters from 150 nm to 5,000 nm.

46. The method of aspect 45, wherein the isolated ICVs or isolated antigenic ICVs have average diameters from 1000 nm to 5,000 nm.

47. The method of aspect 43, wherein the isolated ICVs or isolated antigenic ICVs comprise a cargo selected from biological molecules, therapeutic agents, prodrugs, gene silencing agents, chemotherapeutics, diagnostic agents, components of a gene therapy system and/or components of a gene editing system, preferably wherein the biological molecules are selected from nucleic acids, peptides/proteins, viruses, hormones, carbohydrates, lipids, and vitamins, preferably where the gene silencing agents are selected from siRNA, chRNAs, miRs, ribozymes, morpholinos, and esiRNAs, preferably wherein the components of a gene editing system are selected from CRISPR-Cas systems, zinc finger nucleases, and TALENs.

48. The method of aspect 47, wherein the isolated ICVs or isolated antigenic ICVs are loaded with the cargo by direct membrane penetration, chemical labeling and conjugation, electrostatic coating, adsorption, absorption, sonification, electroporation, use of pH gradients, or any combination thereof.

49. The method of aspect 47, wherein the isolated ICVs or isolated antigenic ICVs are loaded with the cargo by incubating isolated ICVs or isolated antigenic ICVs, or the cells used to produce ICVs or antigenic ICVs, 50. The method of any one of the previous aspects, wherein the cells comprise or have been modified to comprise one or more functional moieties on the cell surface.

51. The method of aspect 40, wherein the one or more functional moieties are one or more targeting ligands.

52. The method of aspect 51, wherein the one or more targeting ligands direct the ICVs or antigenic ICVs to a certain cell, cell type, tissue type, tumor, or organ.

53. The method of aspect 51, wherein the one or more targeting ligands are an antibody or a single-chain variable fragment which binds to a tumor-specific antigen.

54. The method of aspect 51, wherein the tumor-specific antigen is selected from alphafetoprotein (AFP), carcinoembryonic antigen (CEA), CA-125, CA15-3, CA19-9, MUC-1, epithelial tumor antigen (ETA), tyrosinase, melanoma-associated antigen (MAGE), abnormal products of ras or p53, CTAG1B, MAGEA1, and HER2/neu.

55. The method of aspect 50, wherein the cells have been bioorthogonally-conjugated to comprise one or more functional moieties.

56. The method of aspect 55, wherein the one or more functional moieties have been added to the surface of the cells by bioorthogonally-conjugation, comprising:
 (1) treating sialic acid residues on the surface of the cells with an oxidizing agent to form aldehyde groups; then either step (2)(a) and (b), or step (3)(a) and (3)(b):
 (2)(a) ligating, linking or conjugating aminooxy-functionalized molecules to the surface of the cells by forming oxime bonds with the aldehyde groups; and
 (2)(b) inducing production of bioorthogonally-conjugated ICVs or bioorthogonally-conjugated antigenic ICVs by exposing or contacting the cells with the cell blebbing buffer which comprises a sulfhydryl blocking agent or a photosensitizer;
 or
 (3)(a) inducing production of ICVs or antigenic ICVs from the cells by exposing or contacting the cells with the cell blebbing buffer which comprises a sulfhydryl blocking agent or a photosensitizer; and
 (3)(b) producing bioorthogonally-conjugated ICVs or bioorthogonally-conjugated antigenic ICVs by ligating, linking or conjugating aminooxy-functionalized molecules to the surface of the ICVs by forming oxime bonds with the aldehyde groups.

57. The method of aspect 56, wherein the oxidizing agent is either sodium periodate or lead tetraacetate.

58. The method of aspect 57, wherein the cells are treated with 1 mM sodium periodate for 30 min at 4° C.

59. The method of aspect 56, wherein the aminooxy-functionalized molecules comprise a detecting agent, and/or cell-, tumor-, or tissue-targeting ligands.

60. The method of aspect 59, wherein the detecting agent is an enhanced fluorophore-based dye.

61. The method of aspect 56, wherein the aminooxy-functionalized molecules are ligated, linked or conjugated to the aldehyde groups in the presence of a catalyst.

62. The method of aspect 56, wherein the catalyst is p-anisidine.

63. The method of aspect 62, wherein the aminooxy-functionalized molecules are ligated, linked or conjugated to the aldehyde groups in the presence of 10 mM p-anisidine for 90 min at 4° C.

64. Bioorthogonally-conjugated ICVs produced by the method of any one of aspects 55 to 63.

65. The bioorthogonally-conjugated ICVs of aspect 64, wherein the bioorthogonally-conjugated ICVs comprise oxime-linked detecting agents.

66. The bioorthogonally-conjugated ICVs of aspect 64, wherein the bioorthogonally-conjugated ICVs are loaded with one or more small molecule therapeutic compounds or agents.

67. Isolated antigenic ICVs produced by the method of any one of aspects 1 to 55.

68. The isolated antigenic ICVs of aspect 67, wherein the antigenic ICVs are loaded with one or more small molecule therapeutic compounds or agents.

69. Isolated ICVs produced by the method of any one of aspects 1 to 55.

70. A pharmaceutical composition comprising the bioorthogonally-conjugated antigenic ICVs of aspect 66, the isolated antigenic ICVs of aspect 67, or the isolated ICVs of aspect 69; and a pharmaceutically acceptable carrier, excipient, and/or diluent.

71. A method of stimulating an immune response to a cancer in a subject in need thereof, comprising:
administering the pharmaceutical composition of aspect 70 to the subject.

72. The method of aspect 71, wherein the cancer is selected from squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulvar cancer, thyroid cancer, hepatic carcinoma, leukemia and other lymphoproliferative disorders, and various types of head and neck cancers.

73. The method of aspect 71, wherein the pharmaceutical composition is administered by intravenous administration, intertumoral administration, intraperitoneal administration, intramuscular administration, intracoronary administration, intraarterial administration, subcutaneous administration, transdermal delivery, intratracheal administration, subcutaneous administration, intraarticular administration, intraventricular administration, inhalation, or intracerebral administration.

74. The method of aspect 71, wherein the pharmaceutical composition is administered to the subject concurrently or sequentially with one or more anticancer agents or chemotherapeutics.

75. A method of treating a disease or disorder in a subject in need thereof, comprising:
administering the pharmaceutical composition of aspect 70.

76. A method of stimulating an immune response to a cancer in a subject in need thereof, comprising:
(a) obtaining antigen presenting cells;
(b) pulsing the antigen presenting cells with an antigen associated with cancer cells;
(c) inducing cell membrane blebbing by use of a sulfhydryl blocking agent;
(d) collecting antigenic micrometer sized ICVs (mICVs) induced by cell membrane blebbing; and
(e) administering said antigenic mICVs to the subject in need of immunotherapy.

77. The method of aspect 76, wherein the cancer is selected from squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, valvar cancer, thyroid cancer, hepatic carcinoma, leukemia and other lymphoproliferative disorders, and various types of head and neck cancers.

78. The method of aspect 76, wherein the antigen presenting cells are dendritic cells, macrophages, monocytes, Langerhans cells, B cells, genetically modified cells, and mesenchymal stem cells.

79. The method of aspect 77, wherein the antigen presenting cells are immature dendritic cells that are pulsed with an antigen to produce semimature or mature dendritic cells.

80. The method of aspect 79, where the immature dendritic cells are derived from bone marrow of a human subject.

81. The method of aspect 76, wherein the antigen presenting cells are obtained from the subject to be treated by immunotherapy.

82. The method of aspect 76, wherein the sulfhydryl blocking agent is paraformaldehyde.

83. The method of aspect 76, wherein the antigenic mICVs have diameters from 1 micrometer to 5 micrometers.

84. The method of aspect 76, wherein the antigenic mICVs are administered by intravenous administration, intertumoral administration, intraperitoneal administration, intramuscular administration, intracoronary administration, intraarterial administration, subcutaneous administration, transdermal delivery, intratracheal administration, subcutaneous administration, intraarticular administration, intraventricular administration, inhalation, or intracerebral administration, preferably wherein the antigenic mICVs are administered by intravenous administration, or intertumoral administration.

85. The method of aspect 76, wherein the antigenic mICVs are administered concurrently or sequentially with one or more anticancer agents or chemotherapeutics.

86. A cell-free cell therapy comprising the pharmaceutical composition of aspect 69 for use in treating a subject having a disease or disorder.

87. The cell-free cell therapy of aspect 86, wherein the subject has cancer. 88. A vaccine comprising the pharmaceutical composition of aspect 70 for prevention of an infection in a subject by an infectious agent.

89. The vaccine of aspect 88, wherein the infectious agent is a bacterium, a virus, a fungus, or a protozoon.

90. A therapeutic vaccine comprising the pharmaceutical composition of aspect 70 for use in treating a subject having cancer.

The following examples are intended to illustrate but not limit the disclosure. While they are typical of those that might be used, other procedures known to those skilled in the art may alternatively be used.

EXAMPLES

Cell culture. HeLa cells were obtained from American Type Culture Collection (ATCC) and cultured in DMEM (Thermo Fisher Scientific, Waltham, MA), 10% FBS (Gemini Bio Products, West Sacramento, CA) and 1% penicillin-streptomycin (Thermo Fisher Scientific, Waltham, MA). A mouse lymphoma cell line (EL4) was obtained from ATCC and grown in DMEM (Thermo Fisher Scientific, Waltham, MA) supplemented with 10% FBS (Gemini Bio Products, West Sacramento, CA) and 1% penicillin streptomycin (Thermo Fisher Scientific, Waltham, MA). An OVA expressing derivative of EL4 (E.G7-OVA) was obtained from the American Type Culture Collection (ATCC) and grown in RPMI (Thermo Fisher Scientific, Waltham, MA) supplemented with 0.40 mg/mL Geneticin (Thermo Fisher Scientific, Waltham, MA), 10% FBS (Gemini Bio Products, West Sacramento, CA) and 1% penicillin-streptomycin (Thermo Fisher Scientific, Waltham, MA). Obtained B3Z CD8$^+$ T hybridomas were grown in RPMI (Thermo Fisher Scientific, Waltham, MA) supplemented with 1 mM sodium pyruvate (Thermo Fisher Scientific, Waltham, MA), 2 mM L-glutamine (Thermo Fisher Scientific, Waltham, MA), 0.055 mM 2-mercaptoethaol (Thermo Fisher Scientific, Waltham, MA), 10% FBS (Gemini Bio Products, West Sacramento, CA) and 1% penicillin-streptomycin (Thermo Fisher Scientific, Waltham, MA). Cells were incubated at 37° C. with 5% $CO_2$ and 100% humidity.

Example 1

Protocol for N-ethylmaleimide induced cell vesicle production: HeLa cells were plated at 70% confluency ($6\times10^6$ cells/100 mm cell culture plate) and incubated for 4 h at 37° C. and 5% $CO_2$. Media was removed and cells were washed three times with 10 mL of 1×DPBS. Then, 2 mM N-ethylmaleimide in 6 mL of 1×DPBS was added to each 100 mm plate and plates were incubated at 37° C. and 5% $CO_2$ for 24 h. Cells were imaged using a standard inverted light microscope and DPBS solution containing ICVs were collected, isolated, and analyzed by dynamic light scattering (DLS) for size.

Protocol for nano- and microscale induce cell vesicle isolation: Cells and debris were removed by centrifugation at 1200 rpm for 5.5 min, repeated three times, each time collecting supernatant into a clean tube. Then, mICVs were isolated from the supernatant by centrifugation at 16,000×g for 10 min. After the first spin, supernatant was collected for nICV isolation while micro ICV pellets were washed with 1×DPBS. This was repeated two additional times, discarding supernatant and washing the mICV pellet with 1×DPBS. nICVs were isolated using 100 kDa Amicon® ultrafiltration at 3300×g for 15 min, repeated three times with 1×DPBS washes. Final mICVs and nICVs collected were suspended in 100 uL 1×DPBS and then characterized.

Characterization of mICVs and nICVs: mICVs and nICVs were imaged using a bright field microscope and inverted light microscope. The sizing of produced ICVs were measured by using dynamic light scattering (DLS). Use of transmission electron microscopy can also be used to size the produced ICVs.

Figure 4:
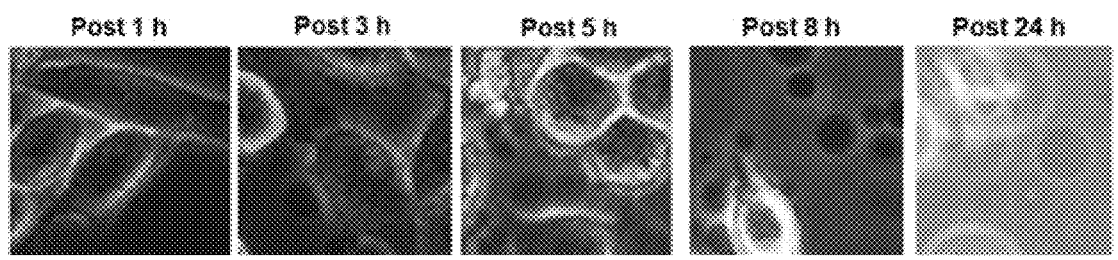
FIG. 4 shows light microscope images of HeLa cells which were exposed to 2 mM NEM in 1×DPBS cell blebbing buffer for varying periods of time (1 h, 3 h, 5 h, 8 h, and 24 h).
Figure 5:
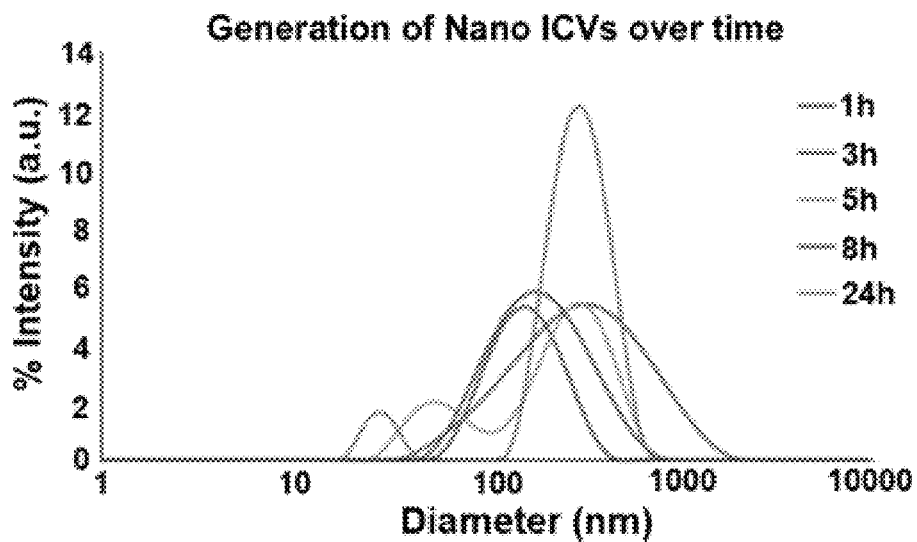
FIG. 5 provides a graph presenting the size distribution of nanometer sized ICVs from FIG. 4 using dynamic light scattering.
Figure 6:
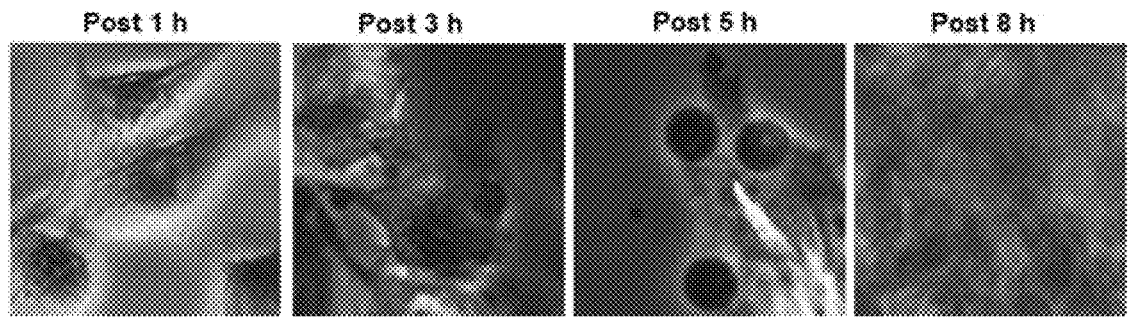
FIG. 6 show light microscope images of HeLa cells which were exposed to 2 mM NEM in 5×DPBS cell blebbing buffer for varying periods of time (1 h, 3 h, 5 h, 8 h, and 24 h).
Figure 7:
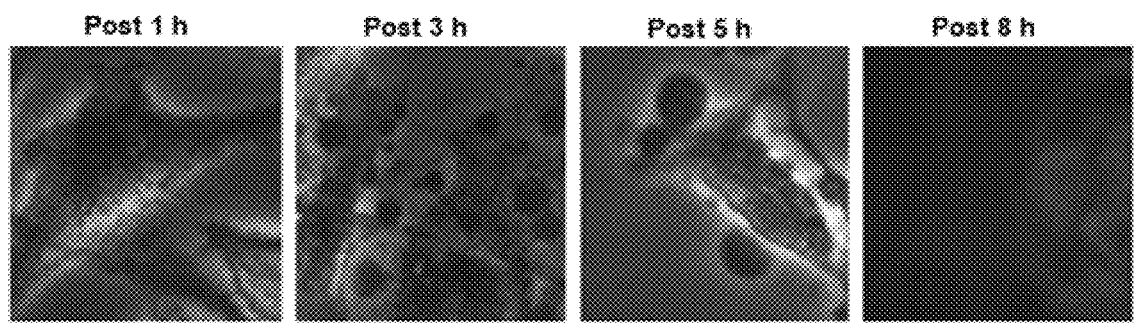
FIG. 7 show light microscope images of HeLa cells which were exposed to 2 mM NEM in 4×DPBS cell blebbing buffer for varying periods of time (1 h, 3 h, 5 h, 8 h, and 24 h).
Figure 8:
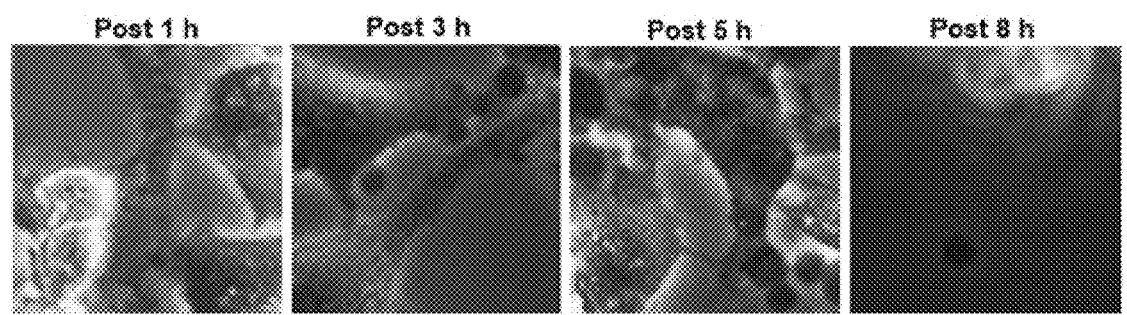
FIG. 8 show light microscope images of HeLa cells which were exposed to 2 mM NEM in 3×DPBS cell blebbing buffer for varying periods of time (1 h, 3 h, 5 h, 8 h, and 24 h).
Figure 9:
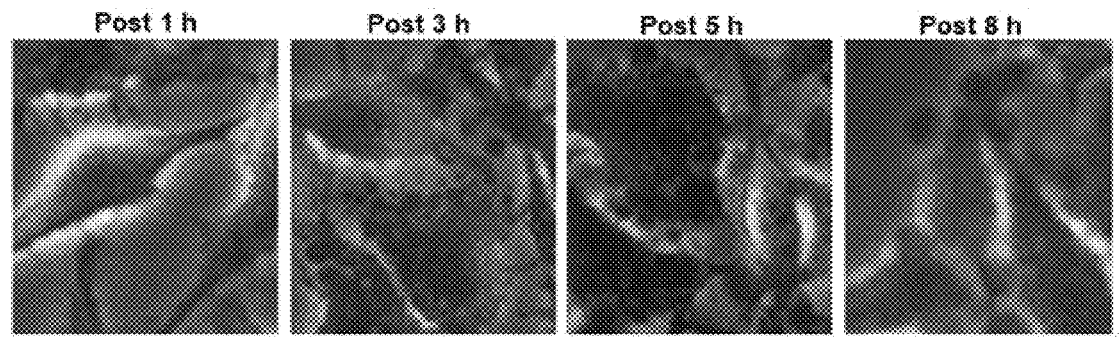
FIG. 9 show light microscope images of HeLa cells which were exposed to 2 mM NEM in 2×DPBS cell blebbing buffer for varying periods of time (1 h, 3 h, 5 h, 8 h, and 24 h).
Figure 10:
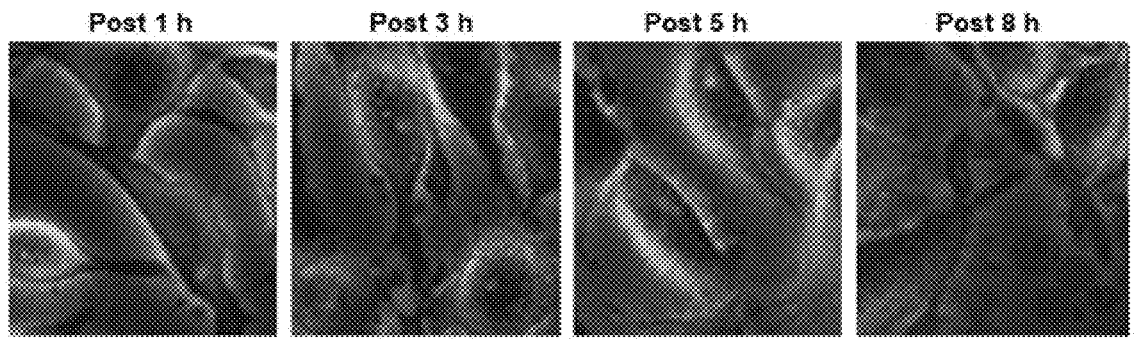
FIG. 10 show light microscope images of HeLa cells which were exposed to 2 mM NEM in 1×DPBS cell blebbing buffer for varying periods of time (1 h, 3 h, 5 h, 8 h, and 24 h).
Figure 11:
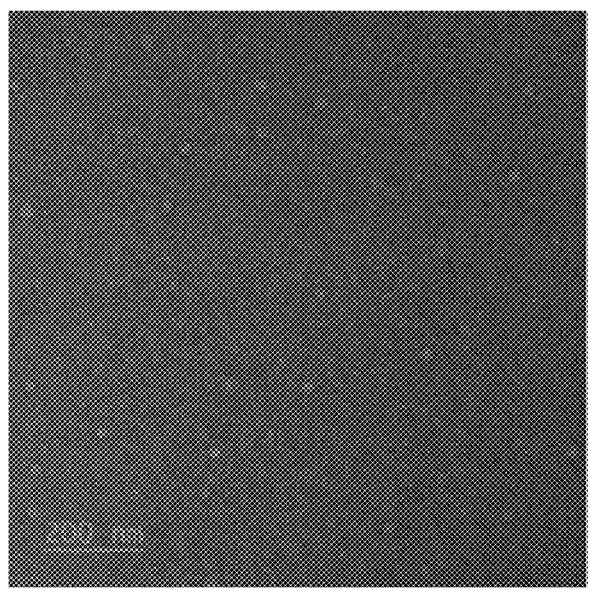
FIG. 11 provides a transmission electron microscopy (TEM) image of nanometer sized ICVs produced by a method of the disclosure.
Figure 12:
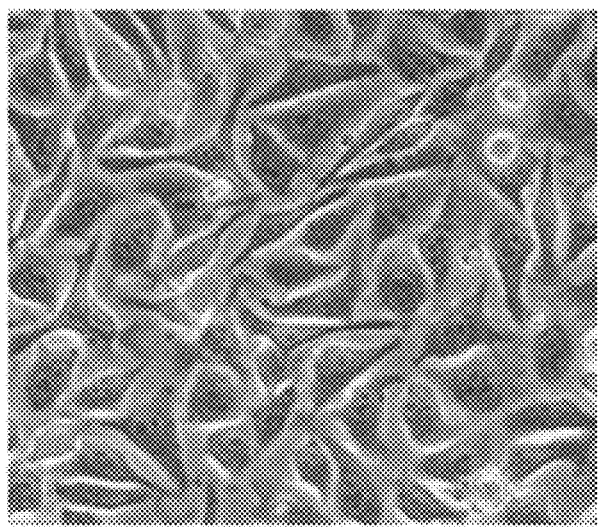
FIG. 12 shows a light microscope image of HeLa cells that were preincubated with photosensitive media prior to being subjected to light generated from a 670 nm laser.
Figure 13:
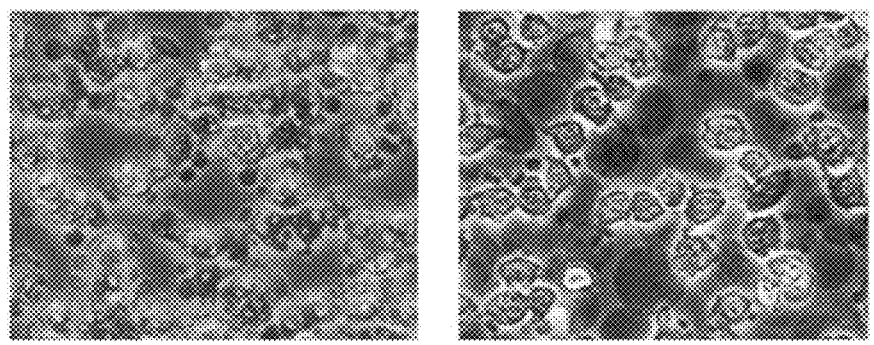
FIG. 13 provides light microscope images of HeLa cells that were incubated with photosensitive media and subjected to light generated from a 670 nm laser for 10 minutes. Left photo: image of HeLa cells that was taken right after laser light exposure. Right photo: image of HeLa cells that was taken 18 hours after laser light exposure.
Figure 14:
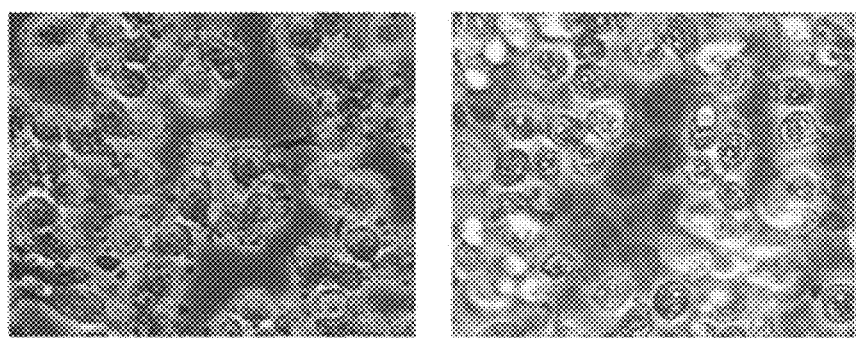
FIG. 14 provides light microscope images of HeLa cells that were incubated with photosensitive media and subjected to light generated from a 670 nm laser for 5 minutes. Left photo: image of HeLa cells that was taken right after laser light exposure. Right photo: image of HeLa cells that was taken 18 hours after laser light exposure.
Figure 15:
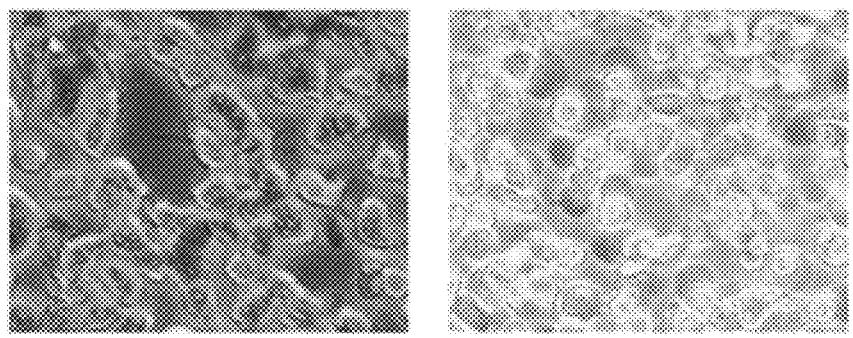
FIG. 15 provides light microscope images of HeLa cells that were incubated with photosensitive media and subjected to light generated from a 670 nm laser for 2.5 minutes. Left photo: image of HeLa cells that was taken right after laser light exposure. Right photo: image of HeLa cells that was taken 18 hours after laser light exposure.
Figure 16:
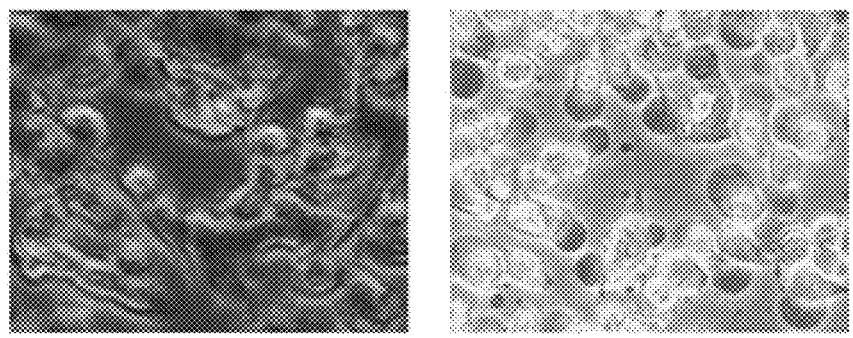
FIG. 16 provides light microscope images of HeLa cells that were incubated with photosensitive media and subjected to light generated from a 670 nm laser for 1.25 minutes. Left photo: image of HeLa cells that was taken right after laser light exposure. Right photo: image of HeLa cells that was taken 18 hours after laser light exposure.

Time course study looking at nICV production by use a cell blebbing buffer comprising NEM over time. In order to better understand the timing for nICV production, a time course study was performed using a cell blebbing buffer comprising N-ethylmaleimide (NEM). In the experiment, HeLa cells were exposed to a cell blebbing buffer comprising 2 mM NEM in 1×DPBS for varying periods of time (1 h, 3 h, 5 h, 8 h, and 24) and imaged by light microscope (e.g., see FIG. 4). Then, mICVs were removed and nICVs were analyzed for size distribution by dynamic light scattering (e.g., see FIG. 5 or by TEM (e.g., see FIG. 11). It was found that the cell blebbing buffer comprising NEM induced the formation of nICVs at each time point.

Time course study looking at the effects of osmotic pressure in conjunction with a cell blebbing buffer comprising NEM on inducing cell vesicle production over time. HeLa cells were plated at 70% confluence in 24-well plates and subjected to a cell blebbing buffer comprising NEM prepared in 1×, 2×, 3×, 4×, or 5×DPBS. Cells were imaged and vesicles were collected at 1 h, 3 h, 5 h, or 8 h after addition of a quenching solution for NEM (e.g., see FIGS. 6 to 10). Based on imaging, a trend of decreasing mICV size was seen by going from 5× to 1×DPBS, indicating that osmotic pressure could potentially play a significant role in assisting in size control. Additionally, a trend of increased mICV size over time was seen within each DPBS concentration, indicating that the time of collection can also play a role in size control of the mICVs. It is expected that nICVs will follow a similar trend, as all vesicles are induced by the same mechanism and membrane blebbing.

Example 2

Protocol for Photoinitiated induced cell vesicle production: HeLa cells were plated at 70% confluency ($6\times10^6$ cells/100 mm cell culture plate) and incubated for 4 h at 37° C. and 5% $CO_2$. Cells were then imaged to confirm adherence to the plate and, in the dark, media was changed to media containing 1 ug/mL of the photosensitizer aluminum disulfonated phthalocyanine ($AlPcS_{2A}$) (10 mL of photosensitizer media per 100 mm each plate). Plates were wrapped in tinfoil and allowed to incubate for 24 h at 37° C. and 5% $CO_2$. In the dark, the photosensitive media was removed and cells were washed three times with 10 mL of 1×DPBS. Then, 6 mL of 1×DPBS was added to each 100 mm plate and the plates were subjected to a 670 nm laser for varying time doses (10 min, 5 min, 2.5 min, 1.25 min). Cells were imaged using a standard inverted light microscope, and the DPBS solution containing ICVs was collected. 6 mL of fresh 1×DPBS was added to each 100 mm plate and the plates were incubated at 37° C. and 5% $CO_2$ for 18 h to investigate ICV formation effects over time. Cells were imaged using a standard inverted light microscope and the DPBS solution containing ICVs was collected.

Protocol for nano- and microscale induced cell vesicle isolation: Cells and debris were removed by centrifugation at 1200 rpm for 5.5 min, repeated three times, each time collecting supernatant into a clean tube. Then, mICVs were isolated from the supernatant by centrifugation at 16,000×g for 10 min. After the first spin, supernatant was collected for nICV isolation while micro ICV pellets were washed with 1×DPBS. This was repeated two additional times, discarding supernatant and washing the mICV pellet with 1×DPBS. nICVs were isolated using 100 kDa Amicon® ultrafiltration at 3300×g for 15 min, repeated three times with 1×DPBS washes. Final mICVs and nICVs collected were suspended in 100 uL 1×DPBS and then characterized.

Characterization of mICVs and nICVs: mICVs and nICVs were imaged using a bright field microscope and inverted light microscope. The sizing of produced ICVs were measured by using dynamic light scattering (DLS). Use of transmission electron microscopy can also be used to size the produced ICVs.

Effects of the duration of light exposure on $AlPcS_2A$ photoinitiated induced cell vesicle production from HeLa cells. In order to better understand the effects of the duration of light exposure on ICV production, a time course study was performed using a 670 nm laser with varying time doses (10 min, 5 min, 2.5 min, and 1.25 min). In the experiment, HeLa cells were first incubated with media containing 1 ug/mL of the photosensitizer $AlPcS_{2A}$ for 24 h, the cells were washed and taken up in 1×DPBS, and then exposed to light from a 670 nm laser.

Figure 17:
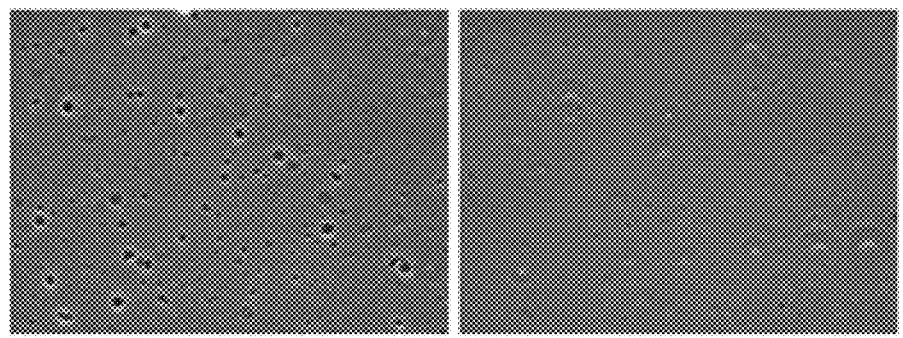
FIG. 17 provides inverted light microscope images of micrometer sized induce cell vesicles produced by incubated with photosensitive media comprising the photosensitizer AlPcS$_{2A}$ and subjected to light generated from a 670 nm laser for 10 min (left photo) or for 5 min (right photo).
Figure 18:
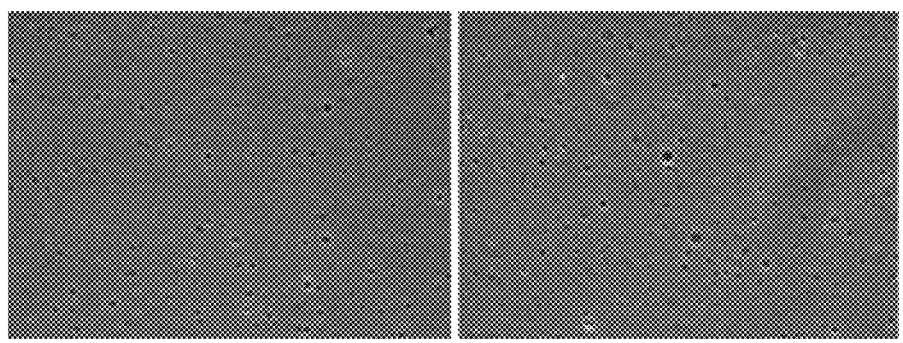
FIG. 18 provides inverted light microscope images of micrometer sized induced cell vesicles produced from HeLa cells which were incubated with photosensitive media comprising the photosensitizer AlPcS$_{2A}$ and subjected to light generated from a 670 nm laser for 2.5 min (left photo) or for 1.25 min (right photo).

It was found that for all of tested light exposure doses (10 min, 5 min, 2.5 min, and 1.25 min), mICVs were produced 18 h after post light exposure. Moreover, it was found that mICVs were produced immediately after 10 min and 5 min light exposure doses (e.g., see FIGS. 13-16; see also FIG. 17 and FIG. 18).

Figure 19:
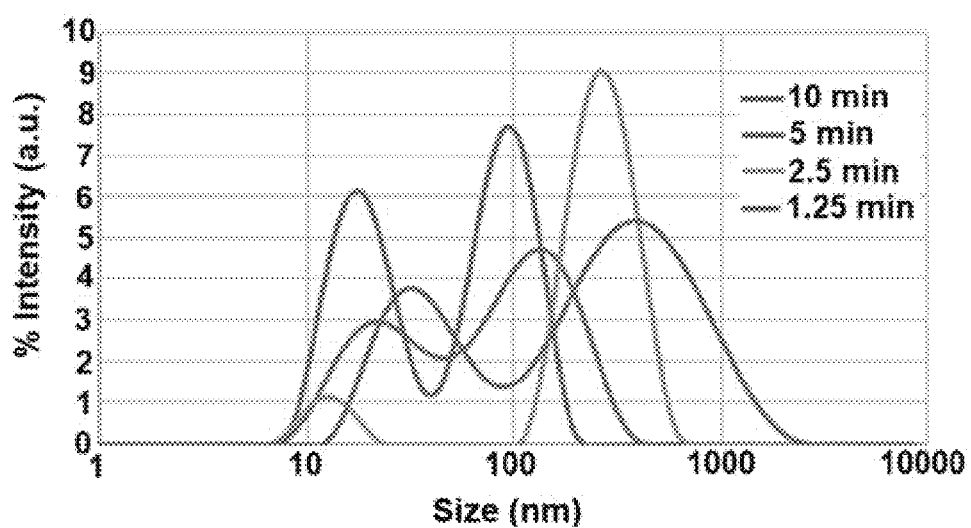
FIG. 19 provides dynamic light scattering (DLS) analysis of nanometer sized induced cell vesicles that were produced immediately after HeLa cells, which were incubated with photosensitive media comprising the photosensitizer AlPcS$_{2A}$, were subjected to light generated from a 670 nm laser for 10 min, 5 min, 2.5 min or 1.25 min.

In regards to nICVs, it was found with dynamic light scattering that all light exposure doses (10 min, 5 min, 2.5 min, and 1.25 min) provided for nICVs with average diameters between 10-600 nm immediately after photoinitiation (e.g., see FIG. 19) and after 18 h post photoinitiation, averages diameters between 40 to 1000 nm (e.g., see FIG.

Figure 20:
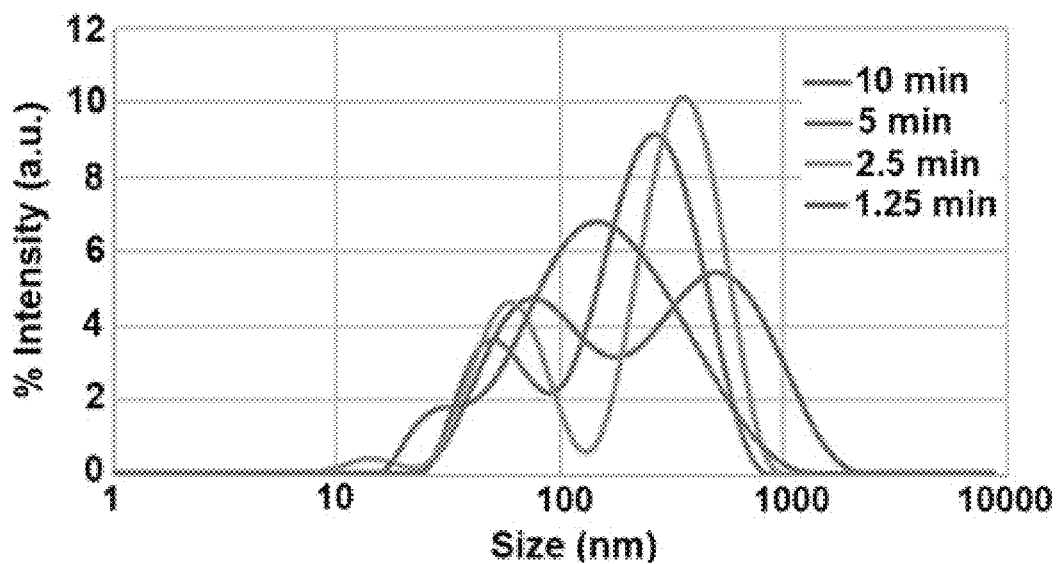
FIG. 20 provides dynamic light scattering (DLS) analysis of nanometer sized induced cell vesicles that were produced 18 h after HeLa cells, which were incubated with photosensitive media comprising the photosensitizer AlPcS$_{2A}$, were subjected to light generated from a 670 nm laser for 10 min, 5 min, 2.5 min or 1.25 min.
Figure 21:
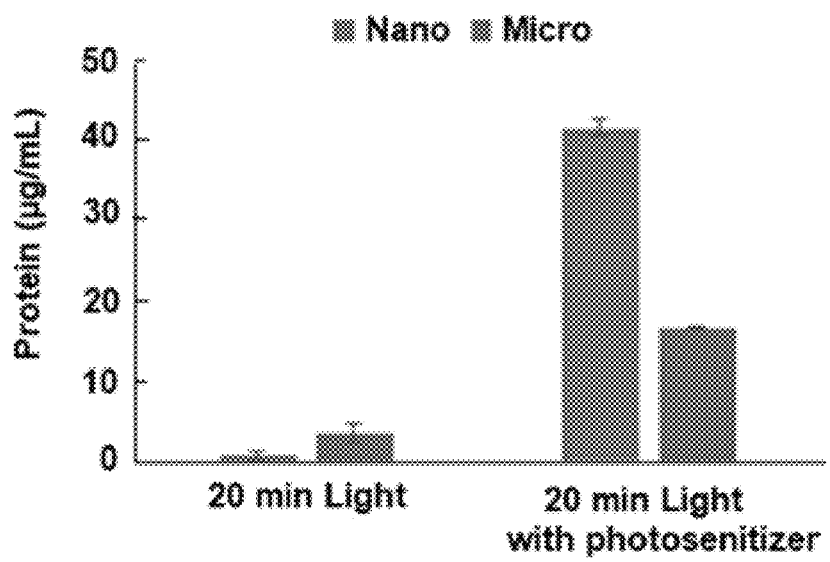
FIG. 21 demonstrates the photo-initiated yield of nanometer sized induced cell vesicles and micrometer sized induced cell vesicles when the cells were exposed to light for 20 min without preincubation with a photosensitizer v. cells preincubated with a photosensitizer and exposed to light for 20 min.

20). Moreover, it was observed that there were clear differences in the size allocation of the nICVs based upon the light exposure dose (e.g., see FIG. 19 and FIG. 20). In control experiment, HeLa cells were incubated with a vehicle control or with media containing 1 ug/mL of the photosensitizer AlPcS$_{2A}$ for 24 h and then exposed to light. It was found that incubation of the cells with the photosensitizer AlPcS$_{2A}$ prior to light exposure greatly increased the yield of nICVs and mICVs v. just exposing the cells to light alone (e.g., see FIG. 21).

Example 3

Protocol for AAV Producer *Cell* Production: To create ICVs loaded with AAV, it was found that it was important for the AAV producer cells to reach a level of about 70% confluence when vesiculation is induced in order to maximize vesicle yield. For production purposes, cells were seeded at ~15% confluence, and after 24 hours, the triple plasmid transfection was delivered to cells. After an additional 24 hours, media was exchanged for fresh media. After a 1-hour incubation, a full dose of the triple plasmid transfection was applied to each plate. After 24 hours, media was exchanged for fresh media. Then, after another 24 hours (48 hours after the second treatment) the cells were either collected and lysed for AAV isolation or treated with the vesiculation components. Three 10 cm plates comprising 1.8×10$^7$ of cells were used for each vesiculation treatment. In the studies the AAV produced was serotype 2 expression GFP.

Figure 33:
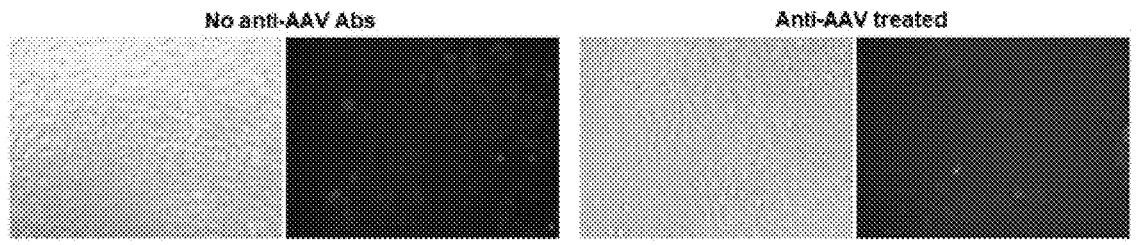
FIG. 33 provides light microscope and fluorescent imaging for supernatant collected from virus producer cells without blebbing or lysis. Anti-AAV antibodies affected transduction efficiency of the control supernatant.

Supernatant collected from AAV producer cells without blebbing or lysis. Producer cells were prepared and triple plasmid transfection was performed in order to make AAV. 48 hours after production began, cells were washed with PBS then DMEM media with FBS was added to the cells. After 24 hours the DMEM was collected and isolated through 100 kDa Amicon filtration (washed three times). This is essentially the control supernatant. As shown in FIG. 33, anti-AAV antibodies affected transduction efficiency of the control supernatant.

Figure 34:
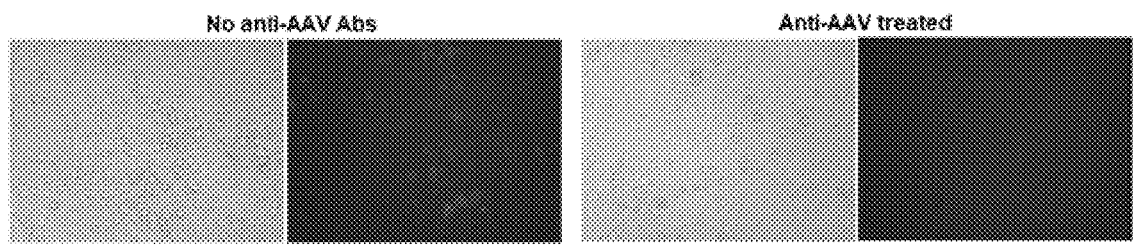
FIG. 34 provides light microscope and fluorescent imaging for supernatant collected from virus producer cells using traditional vesicle formation conditions. Anti-AAV antibodies drastically reduced the transduction efficiency of traditionally produced AAV vesicles, suggesting that very few AAV are actually encapsulated in these vesicles.

Supernatant collected from virus producer cells with traditional extracellular vesicle conditions. Producer cells were prepared and triple plasmid transfection was performed in order to make AAV. 48 hours after production began, cells were washed with PBS then DMEM media without FBS was added to the cells. After 24 hours the DMEM was collected and isolated through 100 kDa Amicon filtration (washed three times). This is the "natural extracellular vesicle production" control. As shown in FIG. 34, anti-AAV antibodies drastically reduced the transduction efficiency of traditionally produced AAV extracellular vesicles, suggesting that very few AAV are actually encapsulated in these extracellular vesicles.

Protocol for the production of induced cell vesicles containing AAV:

(1) AlPCS2A Photosensitizes Initiated Production of ICVs containing AA Vs. Adeno-associated virus producer cells were grown to 70% confluence. Media was then changed to media containing 1 ug/mL AlPCS2A photosensitizer (10 mL of photosensitizer media per 100 mm each plate). Plates were wrapped in tinfoil and allowed to incubate for 24 h at 37° C. and 5% CO$_2$. In the dark, photosensitive media was removed and cells were washed three times with 10 mL of 1×DPBS. Then, 6 mL of 1×DPBS was added to each 100 mm plate and plates were subjected to a 670 nm laser for 10 min or approximately 3 Joules of energy. Cells were then imaged using a standard inverted light microscope, and the DPBS solution containing ICVs was collected. 6 mL of fresh 1×DPBS was added to each 100 mm plate and plates were incubated at 37° C. and 5% CO$_2$ for 24 h to investigate ICV formation effects over time. Cells were imaged using a standard inverted light microscope and DPBS solution containing ICVs was collected.

(2) N-ethylmaleimide Initiated Production of ICVs containing AA Vs. Adeno-associated virus producer cells were grown to 70% confluence. Media was removed and cells were washed three times with 10 mL of 1×DPBS. Then, 2 mM N-ethylmaleimide in 6 mL of 1×DPBS was added to each 100 mm plate. The plates were incubated at 37° C. and 5% CO$_2$ for 24 h. Cells were then imaged using a standard inverted light microscope and DPBS solution containing ICVs was collected. Free-AAV was also exposed to identical vesicle production and isolation methods and included as controls.

Figure 45:
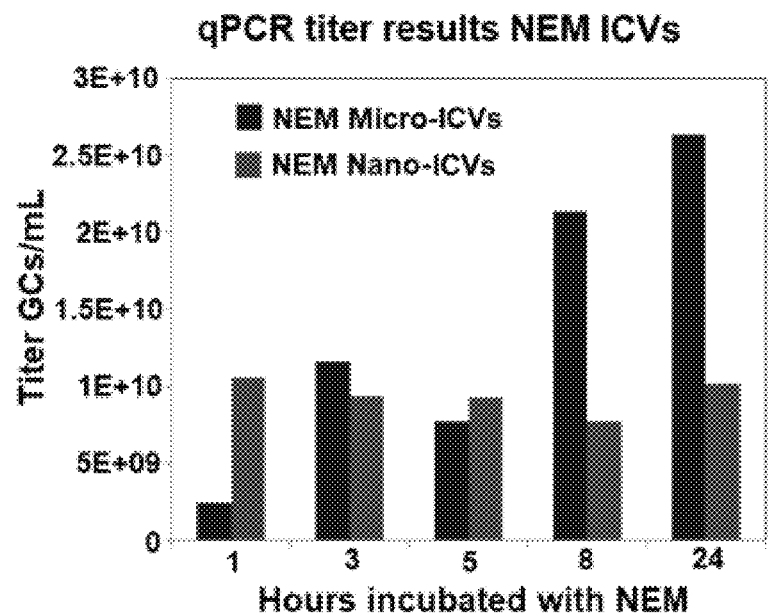
FIG. 45 provides for the optimization of NEM incubation blebbing times. This data was not normalized by number of ICVs and therefore could also be representative of greater yields of AAV containing ICVs over time.

Optimizing NEM Incubation Times for AAV production: HEK293T cells were blebbed in NEM blebbing buffer for 1, 3, 5, 8, or 24 hours. Micro and nano ICVs were isolated as previously described, lysed, and analyzed by QPCR for AAV content. QPCR data demonstrated that nano ICVs generated over time contained the same amount of AAV while micro ICVs contained the most AAV at 8-24 hours. This data was not normalized by number of ICVs and therefore could also be representative of greater yields of ICVs containing AAV over time (see FIG. 45).

Protocol for isolation of ICVs containing AAVs: Cells and debris were removed by centrifugation at 1200 rpm for 5.5 min, repeated three times, each time collecting supernatant and moving to a clean tube. Then, micro ICVs were isolated from the supernatant by centrifugation at 16,000×g for 10 min. After the first spin, supernatant was collected for nano ICV isolation while micro ICV pellets were washed with 1×DPBS. This was repeated two additional times, discarding supernatant and washing micro ICV pellet with 1×DPBS. Nano ICVs were isolated using 100 kDa Amicon filtration at 3300×g for 15 min, repeated three times with 1×DPBS washes. Final micro ICVs and nano ICVs collected were suspended in 100 uL 1×DPBS and then characterized.

Figure 24:
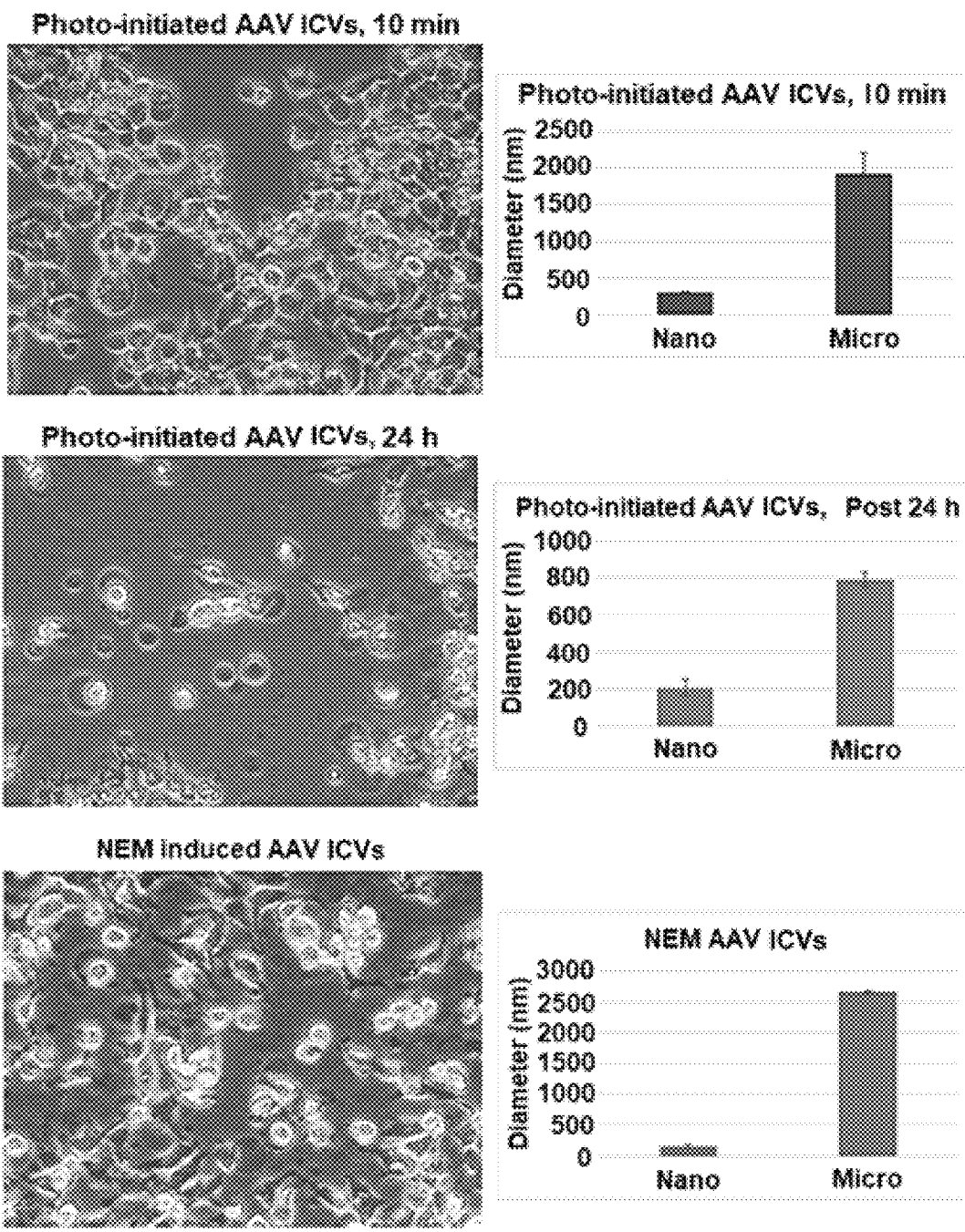
FIG. 24 provides for light microscope imaging and size analysis of photo-initiated induced AAV cell vesicles after 10 min (top), after 24 hours (middle) and NEM AAV cell vesicles (bottom). Micro scale ICVs are visible in these images as circular ICVs with darker contrast compared to cells.
Figure 25:
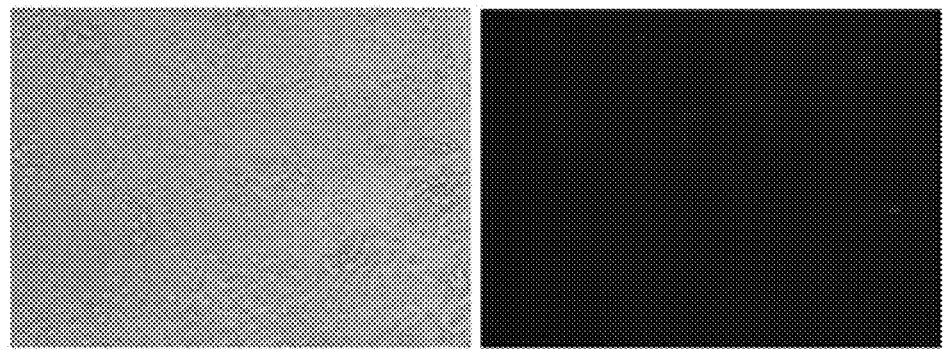
FIG. 25 provides light microscope and fluorescent imaging of supernatant that was collected from virus producer cells without blebbing or lysis. Very weak fluorescence in the cells was observed.
Figure 26:
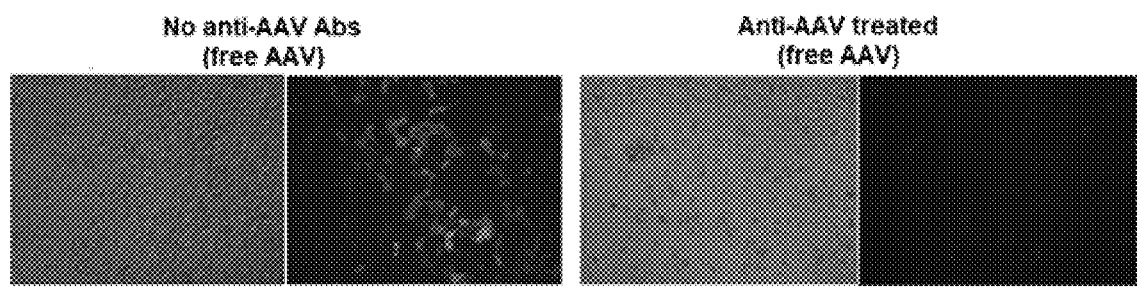
FIG. 26 provides light microscope and fluorescent imaging of transduction tracking for free AAV from cells using a conventional method. As shown, AAVs were inactivated by anti-AAV antibodies.
Figure 27:
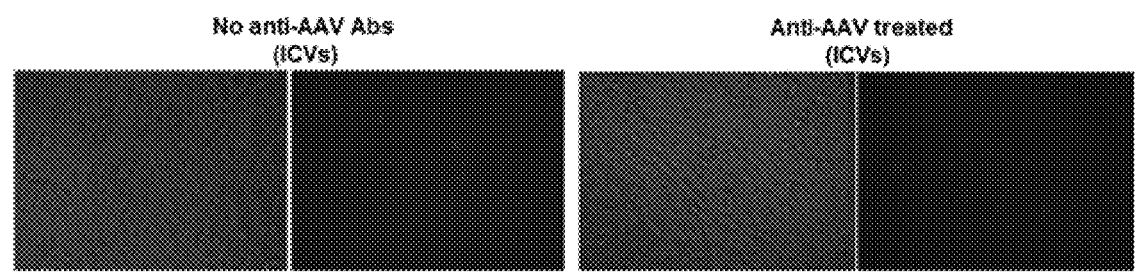
FIG. 27 provides light microscope and fluorescent imaging of transduction tracking for N-ethylmaleimide (NEM) induced nano-sized cell vesicles containing AAV. As shown, there were no effects on AAVs by anti-AAV antibodies, thereby confirming encapsulation of AAVs in ICVs.
Figure 28:
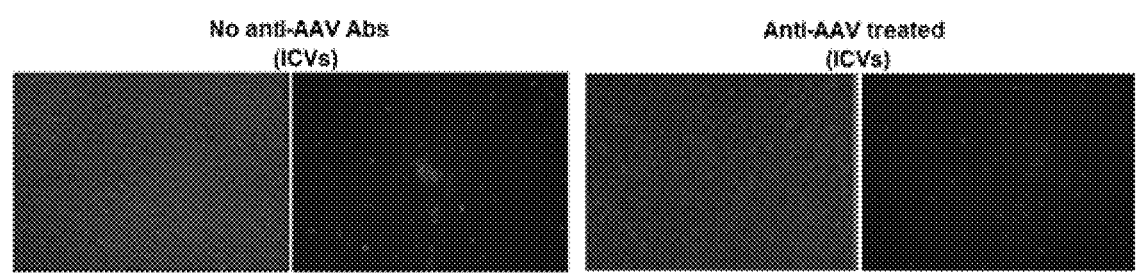
FIG. 28 provides light microscope and fluorescent imaging of transduction tracking for N-ethylmaleimide (NEM) induced micron-sized cell vesicles containing AAV. As shown, there were only negligible effects on AAVs by anti-AAV antibodies, thereby confirming encapsulation of AAVs in ICVs.
Figure 29:
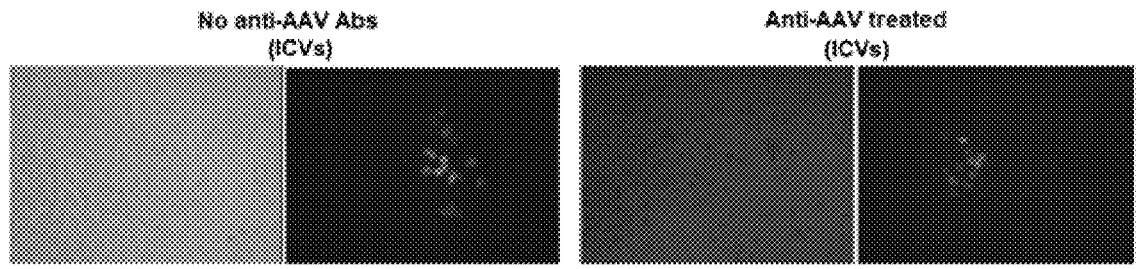
FIG. 29 provides light microscope and fluorescent imaging of transduction tracking for photoinitiated induced nano-sized cell vesicles containing AAV, post 10 min. As shown, there were only negligible effects on AAVs by anti-AAV antibodies, thereby confirming encapsulation of AAVs in ICVs.
Figure 30:
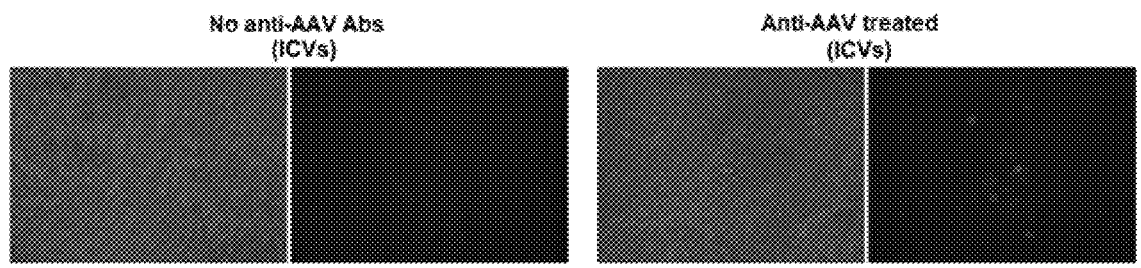
FIG. 30 provides light microscope and fluorescent imaging of transduction tracking for photo-initiated induced micron-sized cell vesicles containing AAV, post 10 min. As shown, there were only negligible effects on AAVs by anti-AAV antibodies, thereby confirming encapsulation of AAVs in ICVs.
Figure 31:
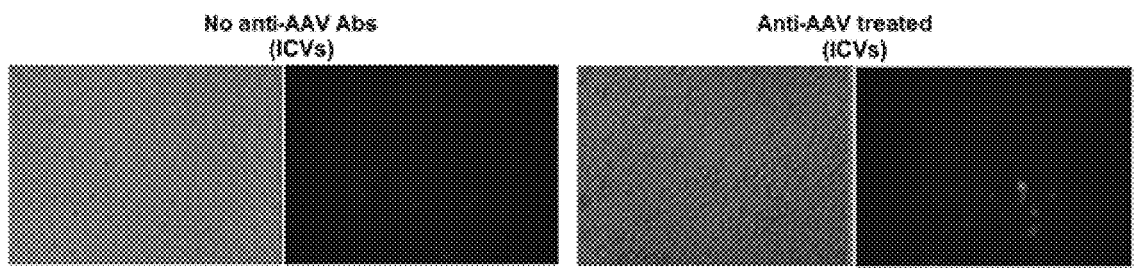
FIG. 31 provides light microscope and fluorescent imaging of transduction tracking for photo-initiated induced nano-sized cell vesicles containing AAV, post 24 h. As shown, there were only negligible effects on AAVs by anti-AAV antibodies, thereby confirming encapsulation of AAVs in ICVs.
Figure 32:
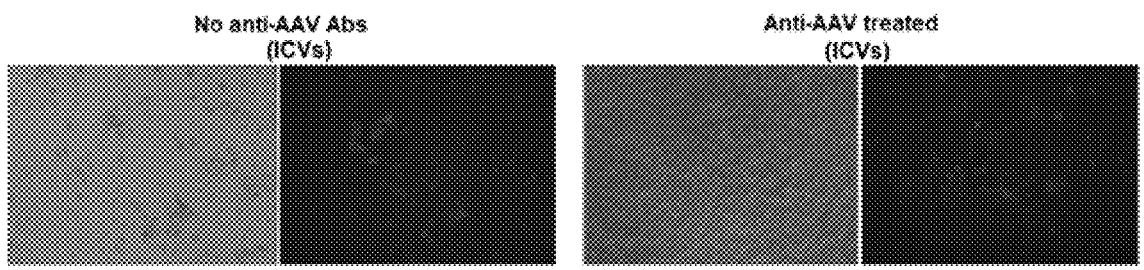
FIG. 32 provides light microscope and fluorescent imaging of transduction tracking for photo-initiated induced micron-sized cell vesicles containing AAV, post 24 h. As shown, there were only negligible effects on AAVs by anti-AAV antibodies, thereby confirming encapsulation of AAVs in ICVs.

Characterization of Micro and Nano-scale ICVs containing AAVs: Light microscope images of AAV producer cells were acquired. ICVs were then isolated and analyzed by dynamic light scattering (DLS) measurements for size. As shown in FIG. 24, there was quite a divergence in the size of induce cell vesicles produced using the various blebbing conditions, with the largest induced cell vesicles being produced by using NEM or photoinitiation for 10 minutes. As shown in the images for FIG. 25, only weak fluorescence was seen in the supernatant from virus producer cells without blebbing. While free AAVs were inactivated by anti-AAV antibodies (see FIG. 26), there was only minimal inactivation by anti-AAV antibodies either nanometer sized ICVs containing AAVs or micrometer sized ICVs containing AAVs from using NEM (see FIG. 27 and FIG. 28). Similar minimal inactivation by anti-AAV antibodies for ICVs containing AAVs produced by using photoinitiation, post 10 min (see FIG. 29 and FIG. 30) and post 24 h. (see FIG. 31 and FIG. 32).

Protocol for ICVs containing AAVs purification using Sucrose gradients. Hek293T cells were plated at 15% confluency, 24 hours later they were given a triple plasmid transfection to produce AAV. After 48 hours incubation, cells were either lysed and AAV collected for the AAV group, or treated with NEM to produce ICVs containing AAVs. These were collected after 8 hours and NEM was removed through filtration. AAVs from lysate and ICVs containing AAVs were separately run on a sucrose gradient and ultracentrifuged to determine which fractions contain free AAVs and which contain ICVs containing AAVs. These were then tittered through qPCR.

AAV from lysate and ICVs containing AAVs were treated with DNase solution for 15 minutes at 37 C to digest any free DNA, then samples were heated to 95° C. for 10 minutes to inactivate DNase. Then samples were treated with a viral lysate solution that lyses the virus and the ICV membrane. Samples were then prepared using qPCR Adeno-Associated Virus Titration (Titer) Kit from Applied Biological Materials Inc. according to kit instructions. Samples were run for qPCR. Resulting data was analyzed according to kit instructions.

Figure 35A:
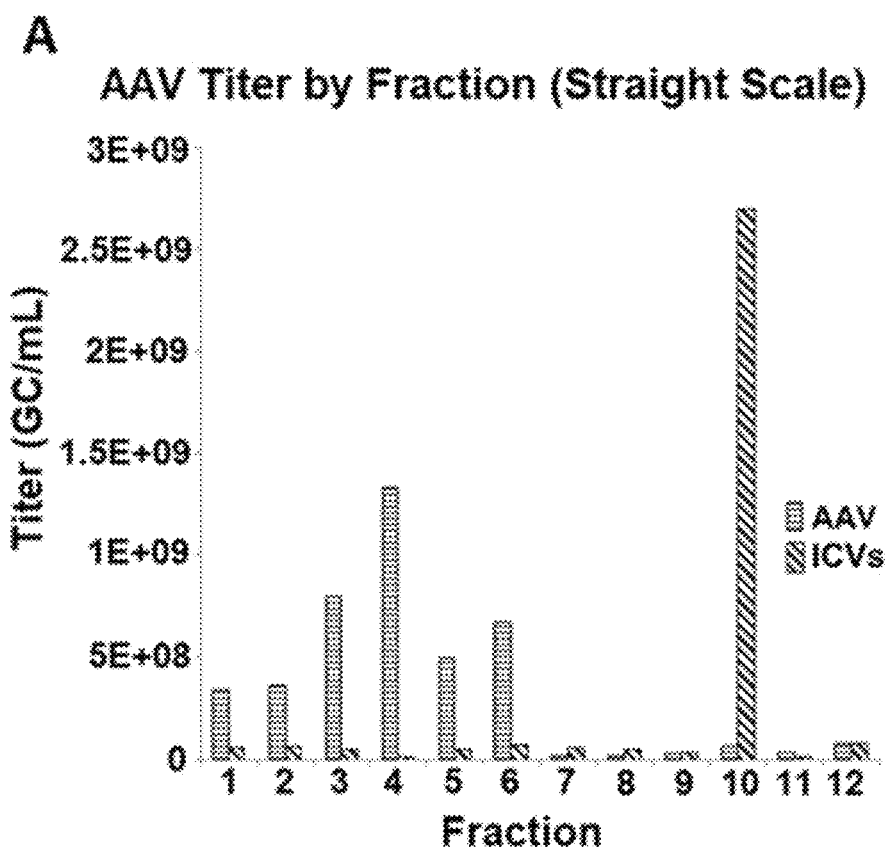
FIG. 35A-B provides free AAV titer and AAV containing ICVs titer from sucrose gradient fractions: (A) straight scale; (B) Log scale. The data shows a clear divide between where AAVs congregate in the sucrose gradient, with AAV fractions in 1-6, (most being in fractions 3-6) and AAV containing ICVs almost solely appearing in fraction 10. This clear division allows for separation of AAV containing ICVs from free AAV, as well as from cellular organelles and debris.
Figure 35B:
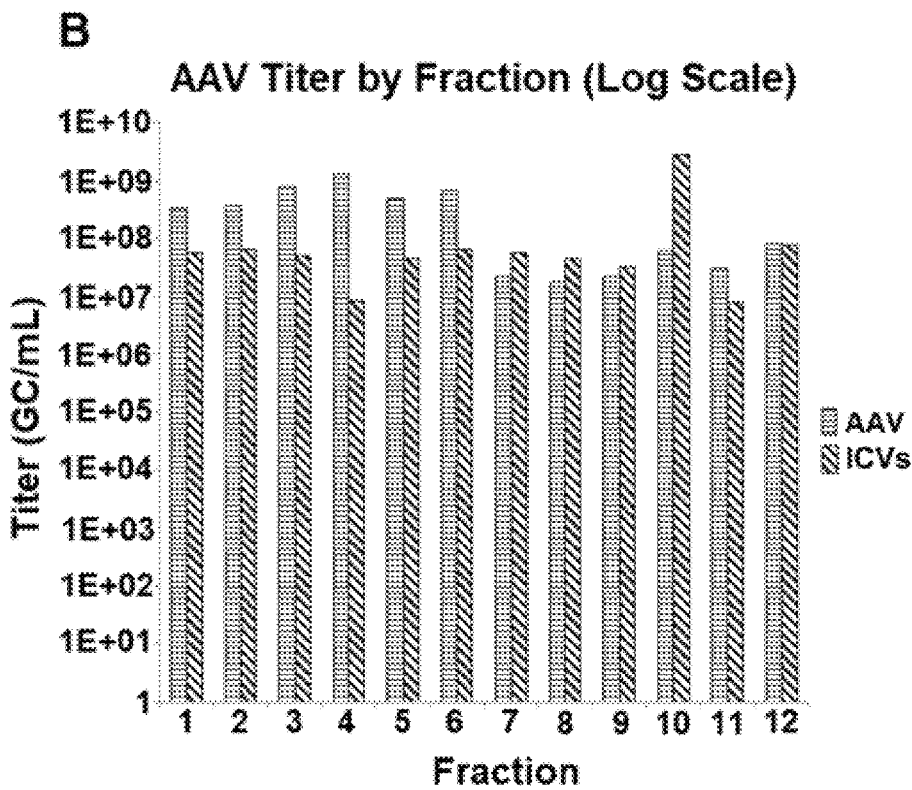
Figure 36A:
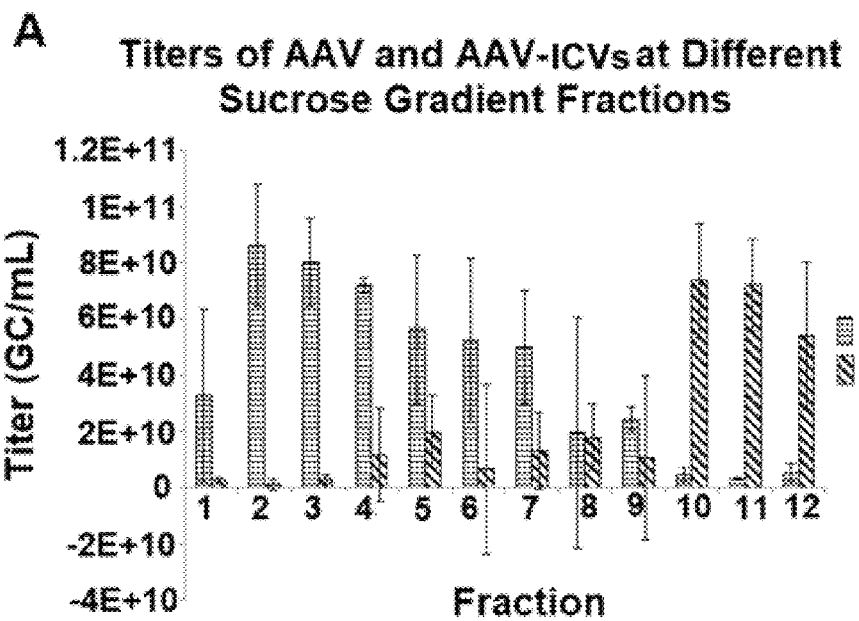
FIG. 36A-B provides free AAV titer and AAV containing ICVs titer from sucrose gradient fractions: (A) straight scale; (B) Log scale. The data shows a clear divide between where AAVs congregate in the sucrose gradient, with AAV fractions in 1-7, (most being in fractions 2-6) and AAV containing ICVs appearing in fractions 10 to 12. This clear division allows for separation of AAV containing ICVs from free AAV, as well as from cellular organelles and debris.
Figure 36B:
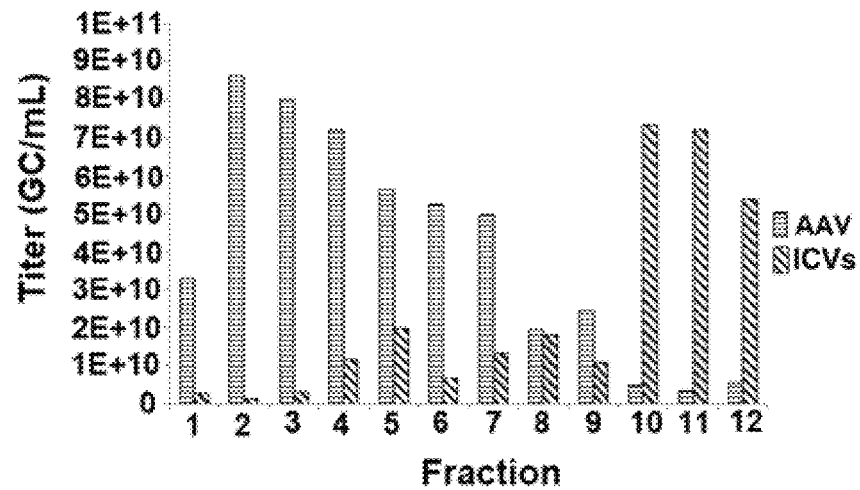
Figure 37:
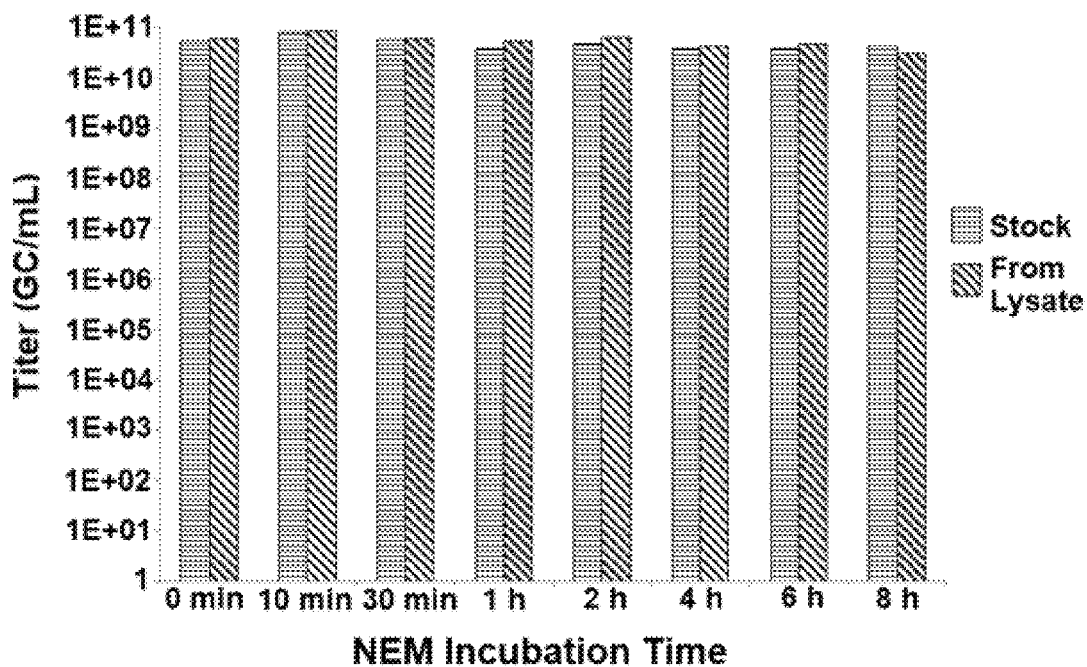
FIG. 37 provides for the determination of titers of AAV stock and AAV from cell lysate treated with NEM. The goal of this experiment was to determine how NEM affected free AAVs versus intracellular AAVs (from producer cells). All titers appeared to be about the same, suggesting that NEM did not cause DNA damage. This data was also used to determine dosing for the next experiment (FIG. 38).

The data shows a clear divide between where AAVs congregate in the sucrose gradient, with AAV fractions in 1-6, (most being in fractions 3-6) and ICVs containing AAVs being mostly in fraction 10 (e.g., FIG. 35A-B) or fractions 10 to 12 (e.g., FIG. 36. A-B). This clear divide between where each species is found, allows for purification of ICVs containing AAVs from any free AAV that may appear in solution, as well as removing any organelles, nucleic acids, and extra protein.

Determining titers of AAV stock and AAV from cell lysate (treated with NEM). The goal of this experiment was to determine how NEM affected free AAVs versus intracellular AAVs (from producer cells). For the stock group, AAVs purchased from Abm® (AAV2-GFP). 6e10 GCs of AAV was incubated in NEM for various timepoints (0 minutes, 10 minutes, 30 minutes, 1 hours, 2 hours, 4 hours, 6 hours, and 8 hours). There titer was determined using qPCR to determine if there was any DNA damage and to find dosing. For the from lysate group, hek293T cells were plated at 15% confluency, 24 hours later they were given a triple plasmid transfection to produce AAV. After 48 hours incubation, cells were lysed and AAV was collected and purified. The resulting AAVs were treated with DNase solution for 15 minutes at 37 C to digest any free DNA, then samples were heated to 95 C for 10 minutes to inactivate DNase. Then samples were treated with a viral lysate solution that lyses the virus and the ICV membrane. Samples were then prepared using qPCR Adeno-Associated Virus Titration (Titer) Kit from Applied Biological Materials Inc according to kit instructions. Samples were run for qPCR. Resulting data was analyzed according to kit instructions. All titers appeared to be about the same, suggesting that NEM did not cause DNA damage. This data was also used to determine dosing for the next experiment.

Quantitative results using AAV stock and AAV producer cell derived AAV treated with NEM. Stock AAV transduction was greatly affected by NEM, reducing the transduction efficiency after just 10 minutes, and leading to almost no transduction after incubation for 2 hours. However, the AAV isolate from lysate showed that the cells had a protective effect (see FIG. 38A-B). There was only a minimal drop in transduction until they had been exposed to NM for 4 hours, and the 8 hours timepoint only showed about half the transduction that the 0-minute timepoint showed (see FIGS. 39 and 40). This demonstrated that any AAV that is free during the blebbing process should be neutralized by the presence of NEM. It also demonstrates that the cell membrane protects AAVs from NEM, and this should translate to the ICVs. Lastly, after seeing minimal DNA damage in a previous experiment, it is clear that the NEM affects protein, affecting the transduction efficiency of the AAVs.

Flow cytometry on cells treated with AAV from stock and lysate and photo-induced cell vesicles (5 minutes). Hek293T cells were plated at 15% confluency, 24 hours later they were given a triple plasmid transfection to produce AAV. After 48 hours incubation, AAV cells groups were lysed and AAV was purified or a photo-initiator was delivered and exposed to a laser. After 5 minutes these were collected and the nICVs and mICVs were separated according to size. Stock AAV was purchased from Applied Biological Materials Inc. HeLa cells were plated and after 24 hours 20 uL of the resulting AAV or ICVs containing AAVs were delivered to each well, with antibody dilutions of 1:16,000, 1:4,000, and 1:1,000 (Ab:AAV). After three days these cells were imaged and run through flow cytometry to analyze fluorescence. Free AAVs were silenced by the neutralizing antibodies (see FIG. 41A). Light induced ICVs containing AAVs were also silenced at a similar amount (see FIG. 41B). This system appeared not to be protective from nAbs.

Flow cytometry on cells treated with NEM initiated ICVs containing AAVs and cells treated with photoinitiated ICVs containing AAVs (24 hours) demonstrating their resistance to nABs. Hek293T cells were plated at 15% confluency, 24 hours later they were given a triple plasmid transfection to produce AAV. After 48 hours incubation, cells were treated with NEM or a photo-initiator and exposed to a laser. After 24 hours these were collected and the nICVs and mICS containing AAVs. were separated according to size. HeLa cells were plated and after 24 hours 20 uL of the resulting ICVs were delivered to each well, with antibody dilutions of 1:16,000, 1:4,000, and 1:1,000 (Ab:AAV). After three days these cells were imaged and run through flow cytometry to analyze fluorescence.

NEM initiated ICVs containing AAVs showed far greater transduction efficiency and were able to resist neutralization by neutralizing antibodies for AAV. The nICVs containing AAVs appeared to resist neutralization but showed insignificant transduction (see FIG. 42A). Photoinitiated ICVs containing AAVs showed a similar profile to the NEM initiated ICVs containing AAVs, except the mICVs containing AAVs did show a response to the neutralizing antibody based on the concertation (see FIG. 42B). However, they resisted being completely neutralized. This is due to the protective effect of the membrane around ICVs protecting AAVs from neutralization.

Figure 44:
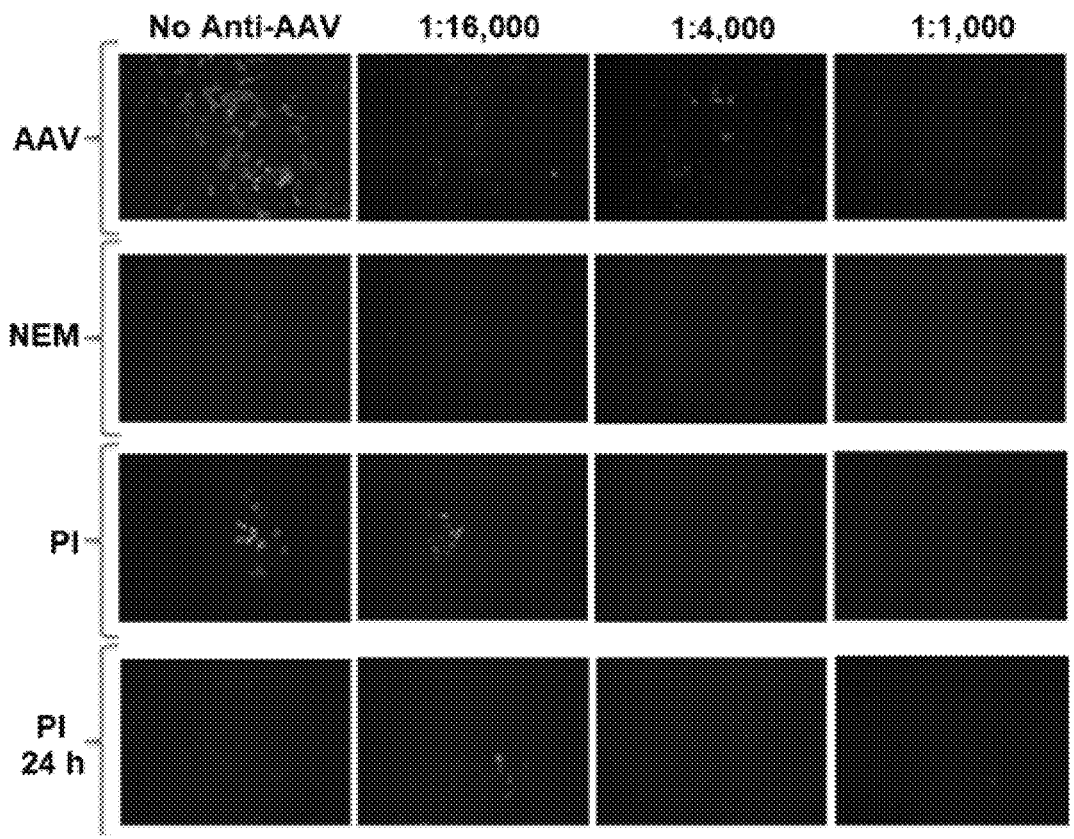
FIG. 44 provides fluorescent images looking at whether nanometer sized AAV containing ICVs can protect from neutralizing antibodies. As shown, nanometer sized AAV containing ICVs were susceptible to neutralization by anti-AAV antibodies.

Protocol for AAV and ICVs containing AAVs Dosing and Transduction Tracking: ICVs containing AAVs and free AAVs were introduced to HeLa cells using 20% of the final volume for each well (40 μL of sample into 100 μL of media). Wells were also treated with no neutralizing antibodies, or antibodies with dilutions in the final volume (i.e., media, sample, and antibody solution). The wells comprised a ratio of virus particles to antibodies of 1:1,000, 1:4,000, and 1:16,000 (virus particles: antibody). After 24 h, the media was switched for fresh media. Images were taken every day after transduction, with the contained images coming from day four post-transduction (e.g., FIG. 43 and FIG. 44).

Example 4

Figure 46:
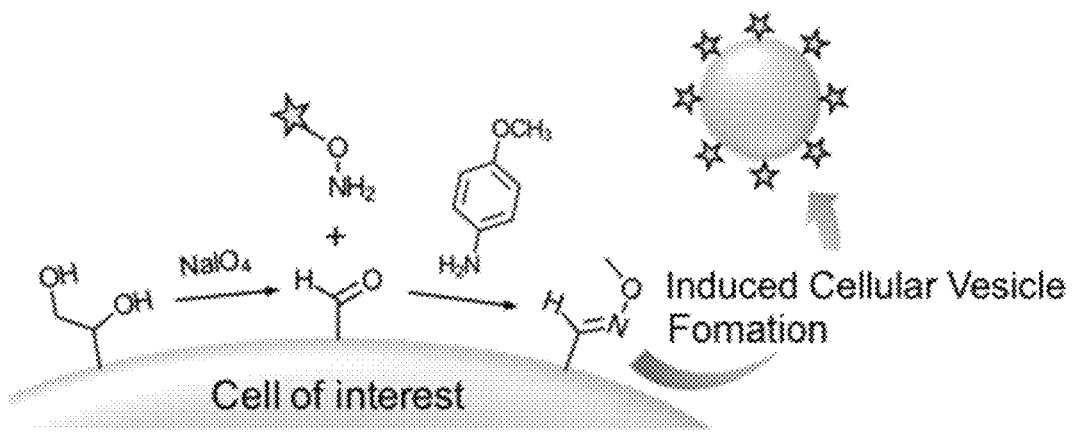
FIG. 46 provides a diagram for the bioorthogonal modification of vesicle-producing cells. Cells are modified by oxime ligation of aminooxy-functionalized molecules with aldehyde groups of oxidized sialylated glycoproteins. ICVs produced from the modified cells retain the bioorthogonally-conjugated molecules of interest on the ICV surface.

Synthetically modifying retroviral surface using bioorthogonal ligation. Both enveloped virus (e.g., influenza virus, retrovirus, and herpes virus) and ICVs are wrapped by phospholipid bilayer membrane that is derived from producer cells. Therefore, enveloped viruses are ICR-like, biologically active nanomaterials and molecular modification of enveloped viral surface is a good model for engineering ICRs. In order to explore the possibility of synthetically modifying retroviral surface, a highly efficient and specific conjugation under biological conditions ("bioorthogonal" ligation) was used. Aminooxy-functionalized molecules can be oxime ligated with aldehyde groups of oxidized sialylated glycoproteins by use of sodium periodate. Since mammalian cells, including retroviral producing cells, display sialic acids on their surface, bioorthogonal cell surface modification generates chemically functionalized retroviral particles in a simple, fast, and efficient way (e.g., see FIG. 46).

293GPG/EGFP cells producing EGFP-expressing VSV-G pseudotyped Molony murine leukemia viruses (MoMLVs) were treated with 1 mM sodium periodate to oxidize the sialic acid on the glycosylated membrane proteins and the resulting aldehyde groups were conjugated with aminooxy-activated biotin in the presence of 10 mM p-anisidine. The retroviral supernatant collected at 24 h after bioorthogonal biotinylation of virus producing cells was conjugated with anti-biotin magnetic particles at the pre-determined optimized ratio. The magnetically labeled retroviral particles were incubated with NIH 3T3 cells on a tissue culture dish where a patterned magnet was applied underneath. Transduced cells (neomycin-resistant cells) survived and were selected to proliferate for one week before visualization with methylene blue staining.

Figure 47A:
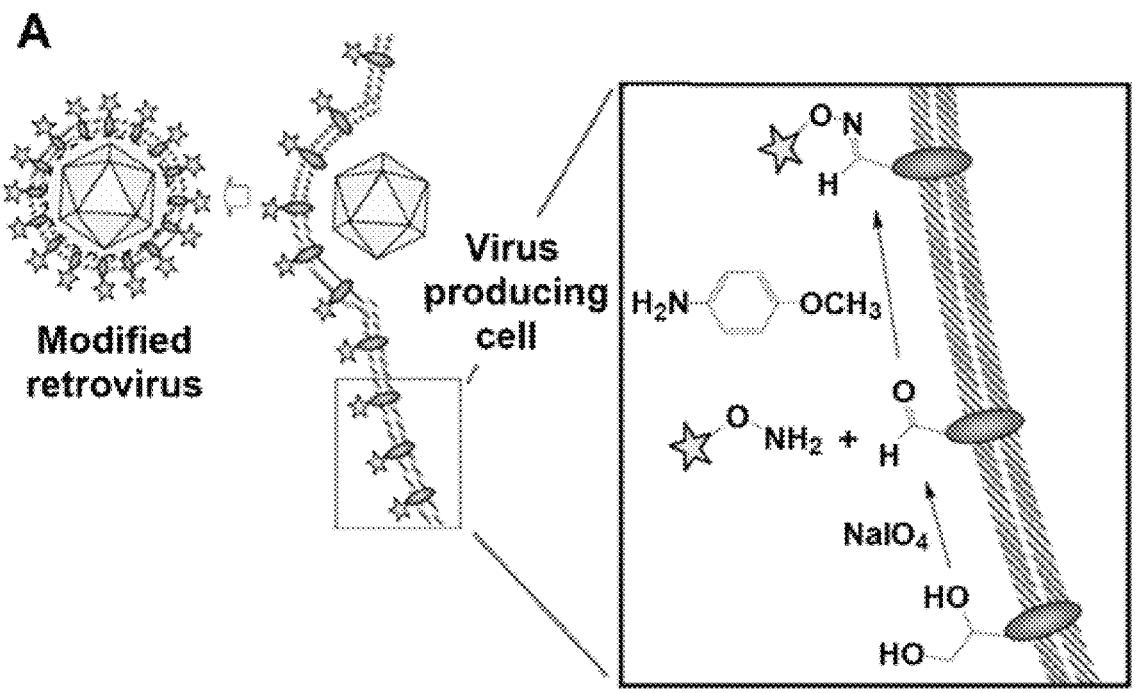
Figure 49:
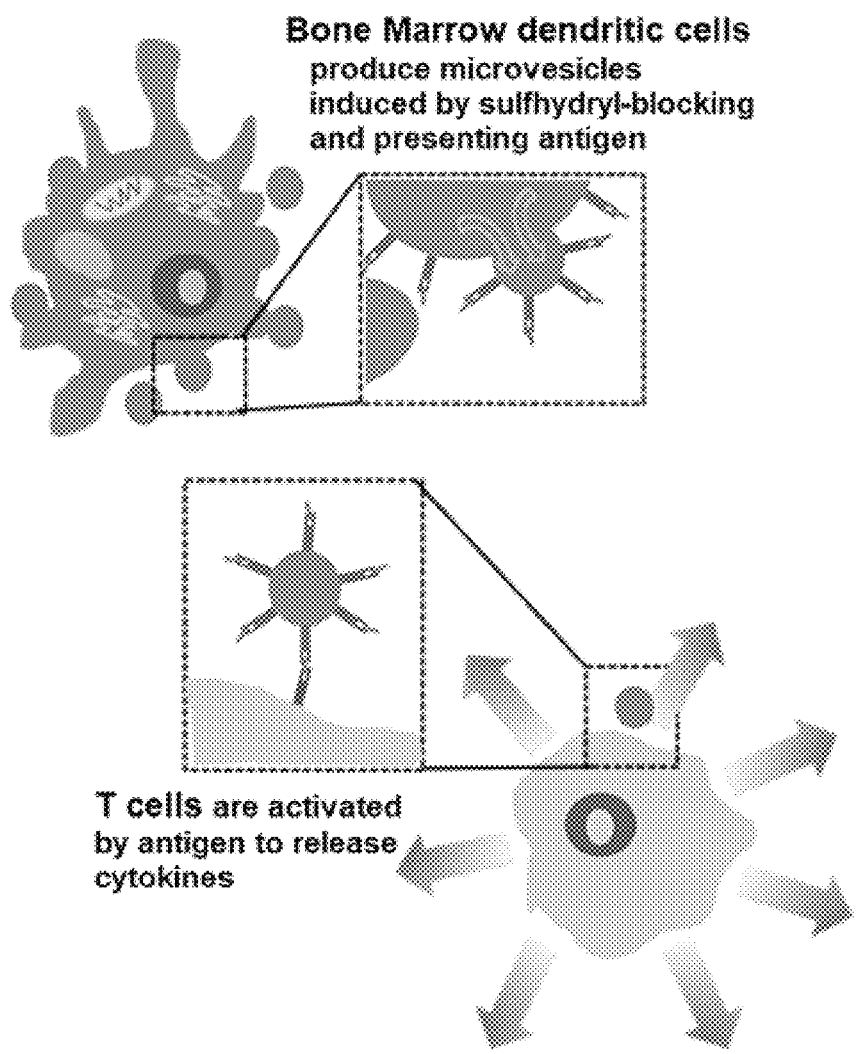
FIG. 49 provides a diagram of the activation of T cells with BMDC-derived ICVs. ICVs induced from BMDCs using the methods of the disclosure present the same antigens as parent cells. They are able to activate T cells in vitro and in vivo to induce anti-tumor immunity. BMDC-derived ICVs have utility for a broad range of biomedical applications since their antigens can be modified easily and they can also be loaded with additional therapeutic cargo.

The results clearly demonstrated that significantly more cells were transduced in the areas where magnetic forces were applied than other areas without magnetic forces (e.g., see FIG. 47B). This confirms that most magnetically labeled retroviral particles were directed to transduce the cells where the external magnetic force was applied. Therefore, magnetically labeled retroviral particles can be used for targeted gene delivery by applying magnetic forces in desired target tissues for localization of significant quantities of viral particles. Magnetic particles are also potent contrast agents for magnetic resonance imaging (MRI).

Magnetically labeling retroviral particles by bioorthogonally functionalizing virus producing cell surfaces is a promising approach to prepare novel viral vectors for gene delivery in combination with in vivo imaging of vector biodistribution by MRI. The retrovirus producing cells were also bioorthogonally modified with a synthetic molecule (aminooxy-ketal-PEG-folic acid [FA])) that is designed to protect the virus during circulation (PEG) but specifically bind to folic acid receptor (FAR)-expressing cancer cells (e.g., see FIG. 47C). FARs are overexpressed by many kinds of cancer cells. The molecules were also designed to cleave (ketal linkage) when the modified virus reaches the mildly acidic endosome/lysosome for full exposure of the VSV-G envelope proteins for rapid release into the cytoplasm upon membrane fusion of viral and endosomal membrane. The resulting viral particles were significantly more efficient in transducing FAR-overexpressing HeLa human cervical cancer cells than FAR-negative NIH 3T3 mouse fibroblasts. Thus, confirming the successful, synthetic engineering of retroviral particles for targeted transduction. The results shown in FIG. 47 demonstrate that the surfaces of virus producing cells were bioorthogonally functionalized to produce retroviral particles carrying functionalized envelope for magnet-directed transduction and cancer cell-targeted transduction.

Bioorthogonal modification of ICVs: In furtherance of the evidence presented in FIG. 47, experiments were performed to confirm whether bioorthogonally labeled cells would produce ICVs with the same modification (e.g., see FIG. 48). As a simple and convenient model, HeLa cells were treated with sodium periodate for sialic group oxidation and conjugated with CF488 as described earlier. The cells were very efficiently labeled with fluorescence (e.g., see FIG. 48A) and the mICVs produced by sulfhydryl-blocking produced from the CF488-labeled HeLa were also fluorescent (e.g., see FIG. 48B). These results confirmed ICVs can be easily engineered by bioorthogonally modifying the surface of the producer cells.

Example 5

Bone-marrow isolation and bone marrow dendritic cell (BMDC) culture. Bone marrow was isolated from femurs of 12-week of C57BL/6 mice (Charles River Laboratories, Wilmington, MA). After mice were euthanized, the femurs were isolated and the bone marrow flushed out with a 25-guage needle using RPMI (Thermo Fisher Scientific, Waltham, MA) supplemented with 10% FBS (Gemini Bio Products, West Sacramento, CA). Red blood cells were lysed using Red Blood Cell Lysis Buffer (Thermo Fisher Scientific, Waltham, MA). Remaining cells were cultured in RPMI (Thermo Fisher Scientific, Waltham, MA) supplemented 10% FBS (Gemini Bio Products, West Sacramento, CA) and 20 ng/mL rmGM-CSF (R&D Systems, Minneapolis, MN). On day 7 of culture, the percentage of BMDCs in the population was assessed with anti-mouse CD11c antibody (BioLegend, San Diego, CA). Cells were then incubated with 20 ng/mL lipopolysaccharide (Sigma Aldrich, St. Louis, MO) for 24 h to induce maturation. The percentage of mature BMDCs (mBMDCs) in the population was assessed with anti-mouse CD40 antibody (BioLegend, San Diego, CA).

Figure 50A:
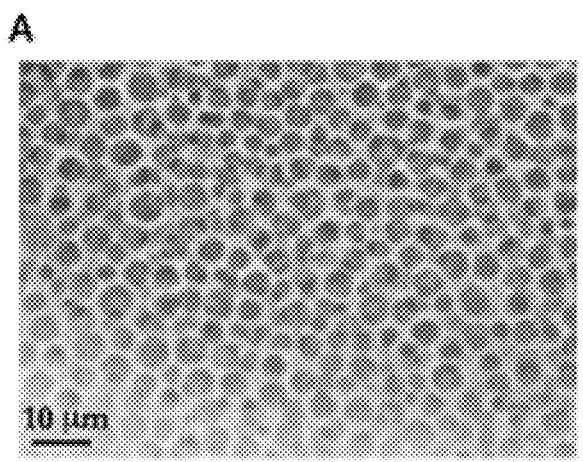
FIG. 50A-B indicates that BMDC-derived ICVs can be effectively produced by chemical crosslinking while maintaining antigen-presenting capabilities. (A) Inverted microscope image of SIINFEKL antigen presenting ICVs. (B) Results of an immunoassay using a fluorescently labeled anti-H-2 kb antibody that binds to SINFEKL labelling.
Figure 50B:
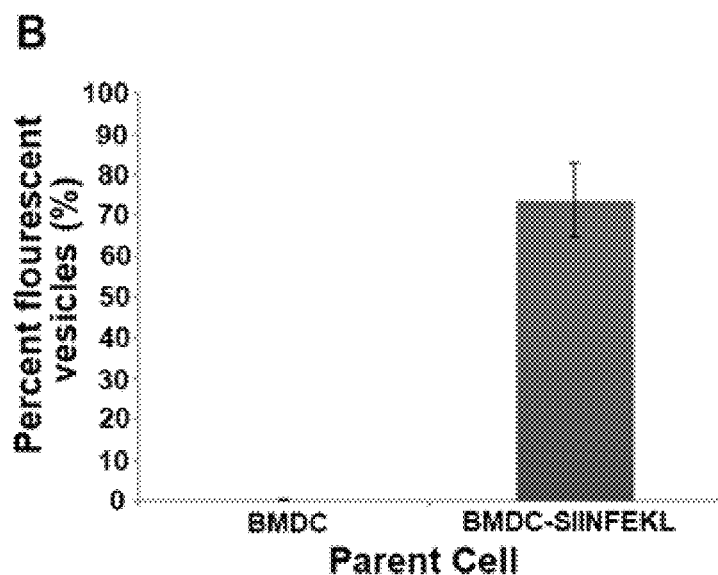

Preparation and isolation of SIINFEKL presenting mICVs. Immature BMDCs (imBMDCs) were incubated with 50 µM SIINFEKL for 1 h prior to maturation. $10^6$ BMDCs/mL in the culture media were centrifuged at 200×g and for 5.5 min and the cell pellet was resuspended and incubated with 25 mM paraformaldehyde (Thermo Fisher Scientific, Waltham, MA) in DPBS for 12 h at 37° C. with 5% $CO_2$. To isolate SIINFEKL-presenting mICVs, cells in the cell blebbing buffer were removed by centrifugation at 200×g for 5 min at room temperature followed by concentration of SIINFEKL-presenting mICVs at 9,300×g for 10 min at room temperature. SIINFEKL-presenting mICVs were washed three times with 10 mL of DPBS. SIINFEKL-presentation was assessed with anti-mouse H-2Kb bound to SIINFEKL antibody (BioLegend, San Diego, CA). As shown in FIG. 50A-B, large numbers of SIINFEKL-presenting mICVs can be produced by using the foregoing method.

Figure 51:
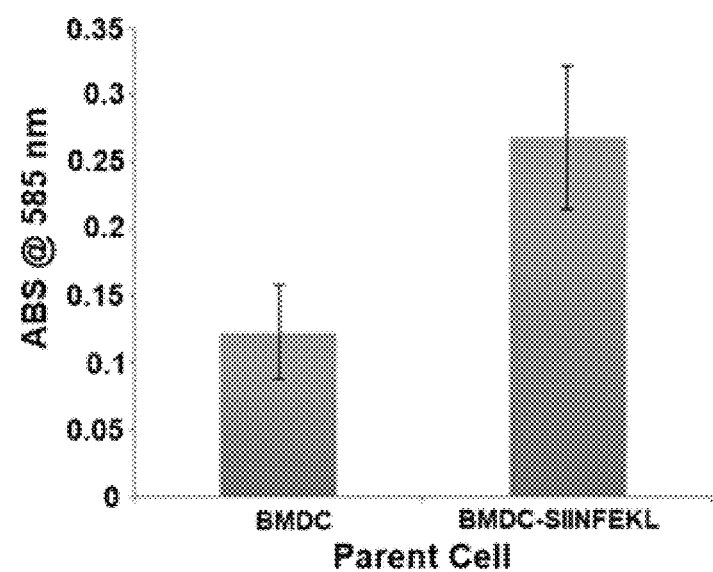
FIG. 51 presents the results of a study looking at T cell activation using a (3-Galactosidase (CPRG) assay and B3Z, a T cell hybridoma line. The greater absorbance in the case of B3Z exposure to antigen-presenting BMDC-derived ICVs indicates that antigen-presenting ICVs are able to activate T cells in vitro.

T cell hybridoma activation assay. T cell activation was assessed using a (3-Galactosidase (CPRG) assay and B3Z, T cell hybridoma line. 10 µL of SIINFEKL-presenting mICVs derived from BMDCs in DPBS were incubated with 30,000 B3Z cells in 100 µL/well of RPMI supplemented with 10% FBS for 24 h at 37° C. with 5% $CO_2$. After 24 h, the plate was spun down and the supernatant removed. Cells were resuspended in CPRG buffer consisting of 90% DPBS, 10% NP-40 (Sigma Aldrich, St. Louis, MO), and 0.6 mg/mL chlorophenol red-β-D-galactopyranoside (Sigma Aldrich, St. Louis, MO) and incubated at room temperature for 12 h. The assay was assessed by measuring absorbance at 595 nm compared to set standards of B3Z cells incubated with BMDCs and known SIINFEKL concentration. As shown in FIG. 51, the greater absorbance in the case of B3Z exposure to antigen-presenting BMDC-derived mICVs indicates that antigen-presenting mICVs are able to activate T cells in vitro.

Figure 52:
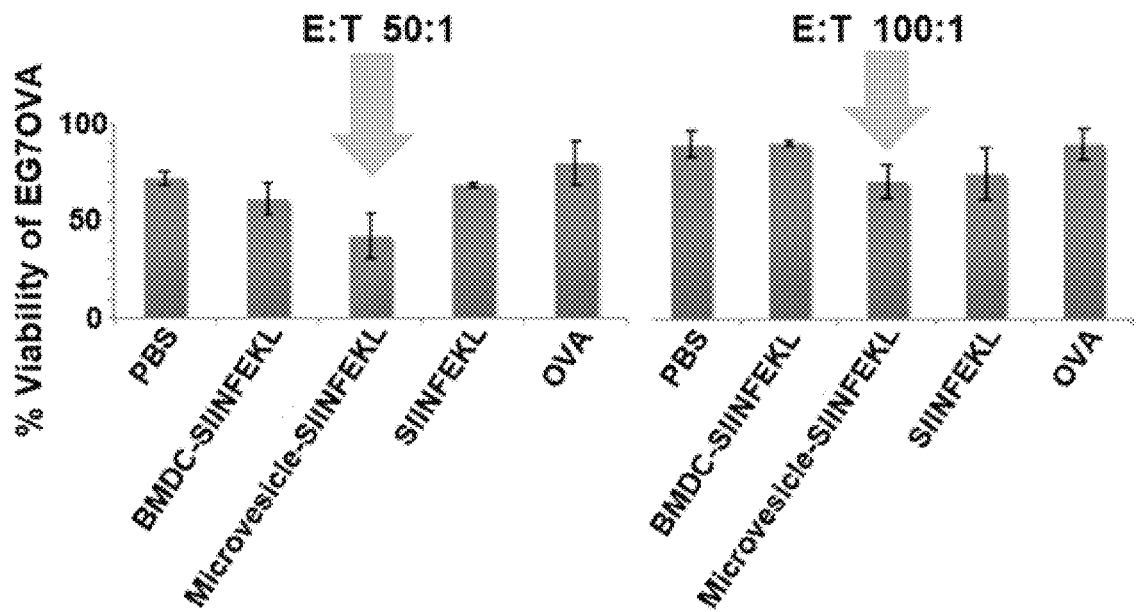
FIG. 52 presents the results of efficacy experiments in mice demonstrating that SINFEKL-presenting ICVs had greater efficacy at stimulating the CTL response then controls at a target ratio of 50:1 or 100:1.
Figure 53:
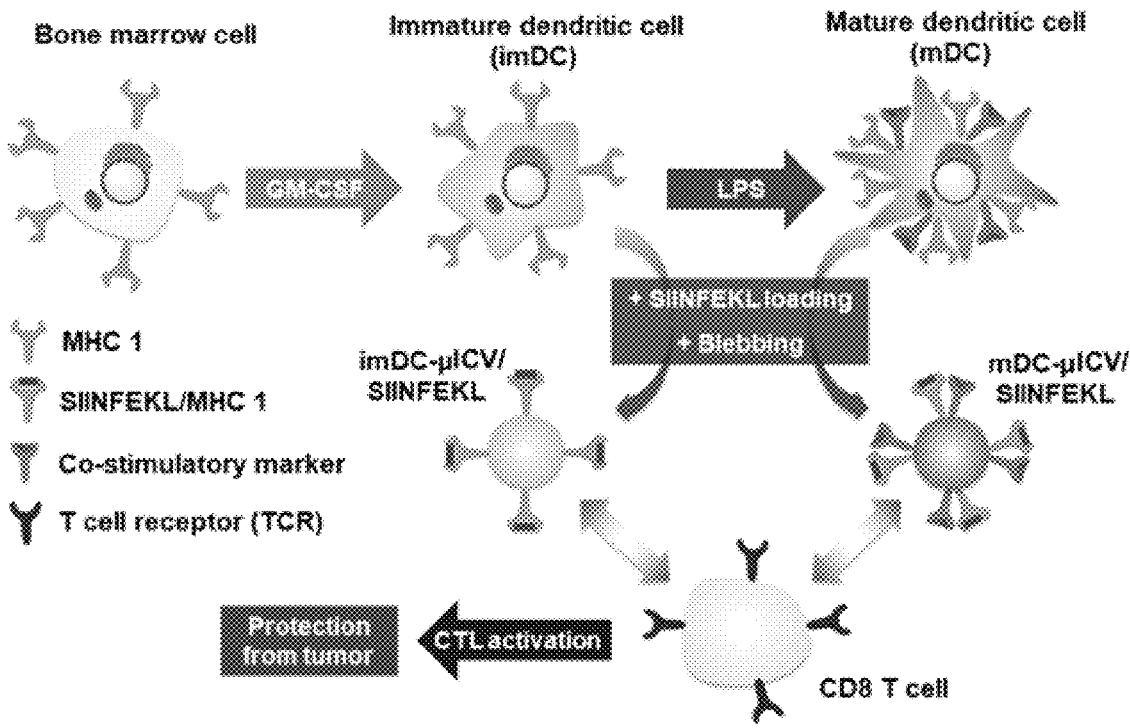
FIG. 53 provides a diagram showing how bone marrow dendritic cells can be used to produce ICVs as a cancer vaccine.

Cytotoxic T lymphocyte assay. In order to evaluate whether immunization with antigen-presenting microvesicles could induced cytotoxic T lymphocyte activation in vivo, a cytotoxic T lymphocyte (CTL) assay was completed. 12 wk.-old C57BL/6 mice (Charles River Laboratories, Wilmington, MA) were vaccinated by s.c. injection with DPBS, OVA protein, SIINFEKL peptide, SIINFEKL-presenting BDMCs, or SIINFEKL-presenting BMDC mICVs. With the exception of the control (DPBS) group, each group received vaccinations that were equivalent to a dosage of 100 µL of 50 µM SIINFEKL as quantified by CPRG assay. Vaccinations were given twice 14 days apart. 7 days after the second injection, mice were sacrificed, spleen cells were isolated, and spleen cells were incubated in various E:T with PKH26 (Sigma Aldrich, St. Louis, MO)-stained E.G7-OVA cells. After 4 h, cells were stained with 1 mM YoPro1 (Thermo Fisher Scientific, Waltham, MA) and viability of the EG7.OVA cells was assessed at two effector to target ratios, 50:1 and 100:1 by flow cytometry. As shown in FIG. 52, antigen-presenting microvesicles show the greatest efficacy at stimulation of CTL response at the 50:1 E:T ratio. At the larger E:T ratio, the difference is less drastic. This may be a result of overloading target cells with effector cells.

Tumor challenge study. 12 wk.-old C57BL/6 mice (Charles River Laboratories, Wilmington, MA) were vaccinated by s.c. injection with DPBS, OVA protein, SIINFEKL peptide, SIINFEKL-presenting BDMCs, or SIINFEKL-presenting BMDC mICVs. With the exception of the control (DPBS) group, each group received vaccinations that were equivalent to a dosage of 100 µL of 50 µM SIINFEKL as quantified by CPRG assay. Vaccinations were given twice 14 days apart. 7 days after the second injection, mice were injected s.c. with 300,000 E.G7-OVA cells in the right flank. Tumor growth was monitored by measuring the tumor size with calipers every 48 h.

Figure 54:
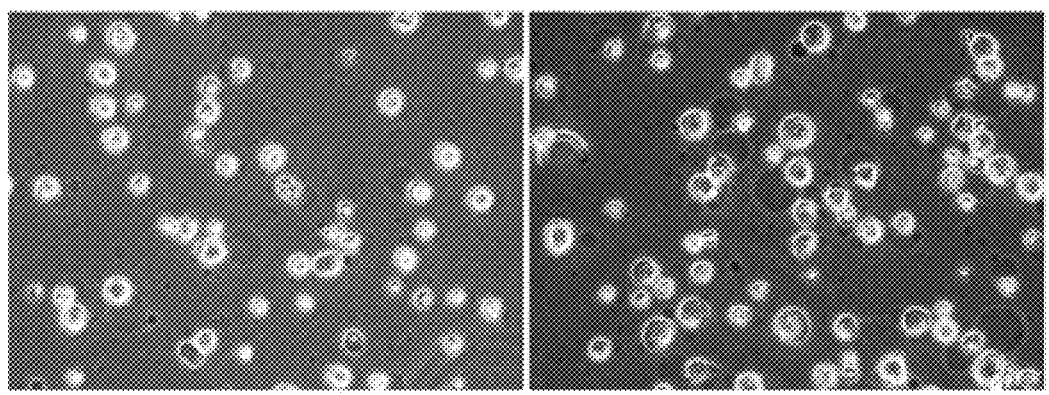
FIG. 54 presents bright field microscope images of BMDC cells undergoing blebbing after 24 h using either 25 mM PFA (left panel) or 25 mM PFA with 2 mM DTT blebbing buffer (right panel). Bone marrow was isolated from C57BL/6 mice and differentiated into BMDCs and matured as previously described. Mature BMDCs were treated with 25 mM PFA, or 25 mM PFA with 2 mM DTT, blebbing buffers for 24 hours, then observed by bright field microscope. Mature BMDC ICVs were prepared in PFA or PFA/DTT blebbing buffers, isolated, and compared for antigen presentation and T cell stimulation.
Figure 55A:
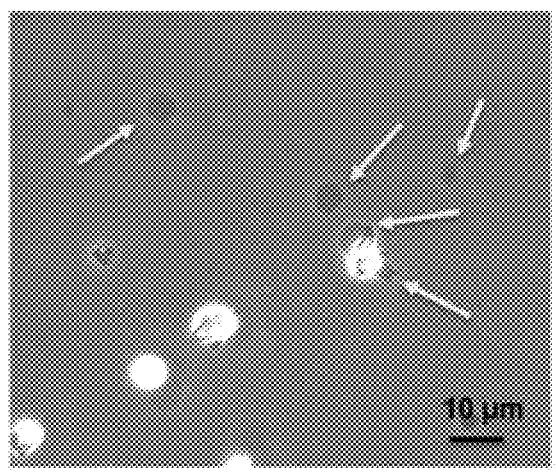
FIG. 55A-C provides for the characterization of ICVs derived from dendritic cells. Immature or mature BMDCS were blebbed in 25 mM PFA blebbing buffer for 24 hours.
Figure 55B:
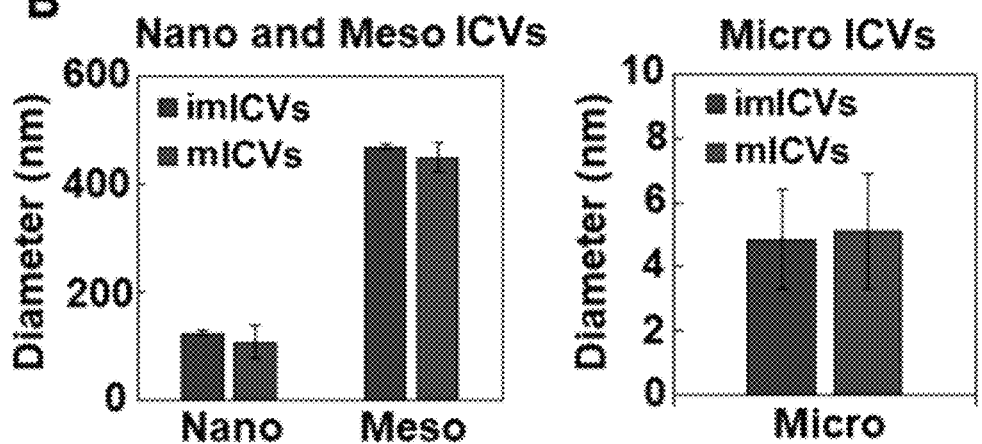
Figure 55C:
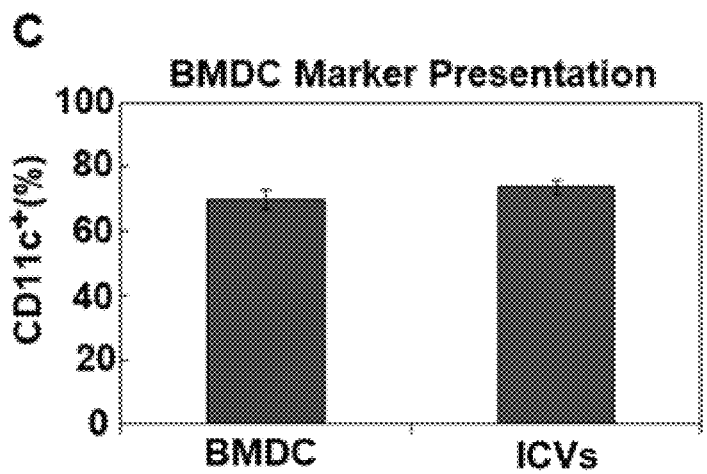

Production and characterization of antigenic mICVs derived from BMDCs. mICVs were efficiently produced from BMDCs in culture by blocking sulfhydryl groups with paraformaldehyde (PFA) or with PFA/DTT (e.g., see FIG. 54). Sulfhydryl-blocking led to rapid ICV production (e.g., see FIG. 55A). This is favorable to natural vesicle production, which requires several days of cell culture and results in significant levels of impurities including proteins and cell debris. The resulting antigenic mICVs were isolated by centrifugation and range in size from 0.05 µm to 5 µm (e.g., see FIG. 55B). Although previous studies have primarily focused on using nano-scale exosomes as vaccines, the studies presented herein assess vesicles of various discrete size ranges. Antigenic mICVs were assessed for CD11c, a specific marker of bone marrow derived dendritic cells (BMDCs). Culture of cells in granulocyte-macrophage colony-stimulating factor (GM-CSF) led to relatively high levels of CD11c expression on antigenic mICVs (e.g., see FIG. 55C). The percentage of CD11c positive antigenic mICVs agrees with the percentage of CD11c positive cells from which they were derived. This is an indication that antigenic mICVs maintain surface protein expression of their parent cells. Although other studies have shown that extracellular vesicles express proteins found on their parent cells, this is the first study to show that ICVs produced via sulfhydryl-blocking maintain a surface protein expressed on their parent cells. The antigenic ICVs were also assessed to see if the antigen presentation was similar to parent dendritic cells. It was found that the antigenic ICVs had similar antigen presentation to parent dendritic cells but with superior stability (e.g., see FIG. 63A-B).

Determining whether the PFA and PFA/DTT blebbing agents interfere with antigenic presentation and T-cell stimulation. It was further determined as to whether use of chemical agents to induce cell blebbing of antigen-presenting cells, impaired antigens and other proteins expressed on the surface of the ICVs. While antigen presentation levels were similar using both PFA and PFA/DTT, it was further found that ICVs produced using PFA were capable of stimulating T cells by nearly 2-fold over ICVs produced using PFA/DTT (e.g., see FIG. 56A-C). This indicated that PFA was the preferred method for inducing BMDC ICV formation, as functionality of ICVs was improved.

Control of maturation properties of antigenic mICVs. While immature BMDCs (imBMDCs) are known to induce tolerance, mature BMDCs (mBMDCs) prime immune cells, and studies have shown that ICVs derived from mBMDCs to be more effective at stimulating T cells. As shown in FIG. 57, mature BMDCs were stained with PKH26 (red membrane stain) and DAPI (blue nuclear stain) and exposed to PFA blebbing buffer. Cells and induced cell vesicle production were observed over time by confocal microscope imaging. Mature BMDCs produced larger ICVs over time, with complete use of cell membrane accomplished at 24 hours post-incubation. Similar blebbing dynamics were seen when immature BMDCs were tracked (e.g., see FIG. 57). Further, both micro and nano ICVs from mature BMDCs and immature BMDCs showed similar size distributions over time (e.g., see FIG. 58A-C).

With the aim of producing antigenic mICVs from a range of immature to mature BMDCs, the cells were assessed for CD40, a costimulatory molecule that is upregulated in mBMDCs. Immature BMDCs were matured in 20 ng/mL lipopolysaccharide (LPS) for 0, 6, and 12 hours to generate BMDCs at different stages of maturation. BMDCs from these time points were blebbed in 25 mM PFA blebbing buffers and mICVs were isolated as previously described. BMDCs from the varying time points and ICVs subsequently produced were labeled with fluorescent anti-CD40 (BMDC maturation marker) and analyzed by flow cytometry. BMDCs and ICVs from varying maturation states showed similar levels of CD40 presentation, a BMDC maturation marker (e.g., see FIG. 60A-B). This indicated that ICVs can have controlled levels of maturation, similar to their parent cells. However, unlike cells, ICVs cannot continue to undergo changes, locking their stage of maturation into place. Additionally, imaging confirmed that antigenic mICVs from mBMDCs expressed CD40 unlike naturally occurring extracellular vesicles (e.g., see FIG. 61). Since it has been shown that mBMDCs are more favorable for applications in immunotherapy, this result is of particular interest, demonstrating that sulfhydryl-blocking offers a means to achieve "mature" antigenic mICVs. It is believed that this is the first report demonstrating precise control over ICV properties based on cell stage.

The antigenic mICVs from a range of immature to mature BMDCs were further assessed for costimulatory marker presentation of CD-80 and CD-86. Immature BMDCs were matured in LPS for 0, 6, and 12 hours to generate BMDCs at different stages of maturation. BMDCs from these time points were blebbed in 25 mM PFA blebbing buffers and mICVs were isolated as previously described. BMDCs from the varying time points and ICVs subsequently produced were labeled with fluorescent anti-CD80 or anti-CD86 (BMDC costimulatory molecules) and analyzed by flow cytometry. Similar to CD40 presentation, ICVs produced from cells of varying stages of maturation presented increased levels of costimulatory molecules that mirrored those of the parent cells (e.g., see FIG. 62A-D). This indicated that ICVs likely mirror many of the parent cell presentation qualities, with the unique feature that ICV presentation is locked and cannot undergo further changes.

The antigenic mICVs from a range of immature to mature BMDCs were also assessed for MHC1 expression. Immature BMDCs were matured in LPS for 0, 6, and 12 hours to generate BMDCs at different stages of maturation. BMDCs from these time points were blebbed in 25 mM PFA blebbing buffers and mICVs were isolated as previously described. Immature and mature BMDCs were labeled with fluorescent anti-MHC1 and compared for MHC1 presentation by flow cytometry. It was found that while percentages of MHC1 positive cells were similar between mature BMDCs and immature BMDC's, density of MHC1 on mature cells was increased by nearly 2-fold (e.g., see FIG. 64A-B). This indicated that mature BMDCs are superior at antigen presentation.

Comparing the molecular contents of BMDCs, ICVs derived from mature BMDCs, and ICVs derived from immature BMDCs. Mature BMDCs or BMDC derived ICVs were lysed in RIPA buffer, vortexed, and run on 12% agarose gels at 100 V for 60 min, then visualized by UV lamp (e.g., see FIG. 65). It was found that mature BMDCs and ICVs display similar RNA profiles, with DNA from the cells displaying at the top of the lane. When ICVs derived from mature BMDCs, and ICVs derived from immature BMDCs were compared on 12% agarose gels after lyses in RIPA buffer with or without RNase treatment, it was found that immature and mature ICVs showed similar RNA profiles (e.g., see FIG. 66).

Identification of RNA from ICVs produced from mature BMDCs using singe-cell RNA sequencing. To further investigate ICV contents, were analyzed by single-cell RNA sequencing analysis. Clusters of particles by similarity in RNA content showed two main clusters (e.g., see FIG. 67B). The main contents of the heat maps are identified in FIG. 68. Many identified RNAs are known to be upregulated in immune cells during maturation/activation. In particular, the following 19 genes of interest were identified:

GM42418: Predicted non-coding gene for C57BL/6 mice.

Fth1 (Ferritin heavy chain 1): Protein coding gene; Gene for cell oxidoreductase, proliferation, establishment of localization and homeostasis processes; Found in mitochondria and vacuole.

AY036118: Non-coding RNA; Involved in cell proliferation, immune system process and system development.

Saa3 (Serum amyloid A 3): Protein coding gene; For signaling receptor binding, protein metabolic process, response to stimulus, signaling; Found in extracellular region.

Mt-Co2 (Mitochondrially encoded cytochrome c oxidase II): Protein coding gene; For oxidoreductase, carbohydrate derivative metabolism, cell death; Found in mitochondria and organelle envelope.

Mt-Co1 (Mitochondrially encoded cytochrome c oxidase I): Protein coding gene; For oxidoreductase and transporter, establishment of localization and response to stimulus; Found in mitochondrion and organelle envelope.

Mt-Co3 (Mitochondrially encoded cytochrome c oxidase III): Protein coding gene; For oxidoreductase, transporter, cellular component organization; Found in mitochondria and organelle envelope.

Ubc (Ubiquitin C): Protein coding gene; For protein metabolic process; Found in nucleus Rpl19 (Ribosomal protein L19): Protein coding gene; For RNA binding, protein metabolic processing; Found in cytosol, non-membrane bounded, synapse.

Vezt (Vezatin): Adherens junction transmembrane protein; protein coding gene; For cytoskeletal protein binding; Found in cell projection, cytoplasmic vesicle, cytosol, nucleus, organelle lumen, plasma membrane.

Snap91 (Synaptosomal-associated protein 91): Protein coding gene; For protein lipid binding, cell differentiation, cell component organization, establishment of localization, signaling, system development; Found in cell projection, cytoplasmic vesicle, cytosol, endosome, plasma membrane, synapse.

Ctbs (Chitiobiase): Protein coding gene; For carbohydrate derivative binding, hydrolase, carbohydrate derivative metabolism; Found in vacuole.

Mont (MON2 homology: regulator of endosome to Golgi trafficking; Protein coding gene; For establishment of localization.

Hif1an (Hypoxia-inducible factor 1): Protein coding gene; For oxidoreductase, signaling receptor binding, cell differentiation, nucleic acid-templated transcription, protein metabolic process, response to stimulus, signaling; Found in cytosol, nucleus, organelle lumen.

Nbas (Neuroblastoma amplified sequence): Protein coding gene; For establishment of localization; Found in the endoplasmic reticulum.

Rock2 (Rho-associated coiled-coil containing protein kinase 2): Protein coding gene; For carbohydrate derivative binding, cell death, cell differentiation, cellular component organization, protein metabolic process, response to stimulus, signaling, system development; Found in cytoskeleton, cytosol, non-membrane-bounded organelle, nucleus, plasma membrane, synapse.

Rap1b (RAS related protein 1b): Protein coding gene; For carbohydrate derivative binding, hydrolase, cell differentiation, cell proliferation, cell component organization, establishment of localization; Found in cytosol, non-membrane bound organelle, plasma membrane.

Tmed7 (Transmembrane p24 trafficking protein 7): Protein coding gene; For cell component organization, establishment of localization; Found in cytoplasmic vesicle, ER, Golgi.

Fbll1 (Fibrillarin-like 1): Protein coding gene; For RNA binding, transferase, cell component organization, protein metabolic process; Found in non-membrane-bounded organelle, nucleus, organelle lumen.

Dosing and T-Cell stimulation between groups of ICVs from immature BMDCs, immature BMDCs, ICVs from mature BMDCs, and mature BMDCs. A dosing protocol based on equivalent surface area of materials was developed for comparisons between groups of ICVs from immature BMDCs, immature BMDCs, ICVs from mature BMDCs, and mature BMDCs. BMDCs were labeled with PKH26, a red fluorescent membrane stain, lysed and read by plate reader for fluorescent intensity. BMDCs were also labeled and blebbed in 25 mM PFA blebbing buffer for 24 hours. mICVs were collected, lysed, and read for fluorescent signal by plate reader.

Comparing equivalent numbers of immature or mature BMDCs, mature BMDCs had nearly 3-fold greater surface area based on PKH membrane signal (e.g. see FIG. 70A-B). Furthermore, mature BMDCs produced 3-fold the amount of ICVs. It is therefore likely that amount of ICVs produced is correlated with surface area of membrane.

Based on equivalent PKH signal, and therefore material surface area, immature or mature BMDCs and ICVs produced therefrom were dosed to T cells and evaluated for T cell stimulation ability by CPRG assay. Based on dosing by equivalent surface area, T cell stimulation had the following trend: ICVs from mature BMDCs>mature BMDCs>immature BMDCs and ICVs from immature BMDCs (e.g., see FIG. 71). When dosing based on surface area, there are more ICVs from BMDCs:T cells than BMDCs:T cells, generating greater likelihood of interactions and stimulation.

Protective immunity in tumor challenge study by mICVs vaccination. While ICVs have a variety of benefits including ease of production, size and lack of whole-cell components, it was important to investigate whether antigenic ICVs had efficacy in generating protective immunity in a tumor challenge scenario. While mature BMDCs are known to induce protective immunity, antigenic ICVs produced by sulfhydryl blocking have not previously been assessed for this potential.

Mice received a single vaccination followed by a booster vaccination two weeks later). Seven days after completion of a vaccination schedule. mice were challenged with E.G7-OVA cells and tumor growth was assessed over four weeks. FIG. 72 provides images from Day 30 of the tumor challenge with mice by vaccine category. PBS, OVA, and SIINFEKL groups all rapidly developed tumors. Immature and mature BMDC vaccine groups developed small tumors by day 15 and went into complete remission. ICVs from immature BMDCs developed tumors at a slowed rate, indicating a low immune response, but not potent enough to prevent tumor growth. ICVs from mature BMDCs developed small tumors, larger than those of the cell vaccine group, and later went into total remission. This data suggests that immature cells likely matured after administration in order to achieve a similar response to the mature cell group. This demonstrates the need for a cell-free vaccine, as cell maturation and state and therefore resulting immune response could not be accurately controlled. However, ICVs from immature BMDCs had a tolerant effect while ICVs from mature BMDCs performed similarly to mature cells. So, while antigenic ICVs were found to be as effective as BMDCs in generating protective immunity in a tumor challenge scenario (e.g., see FIG. 73A), antigenic ICVs exhibit notable technical features over BMDCs, such as scalability, size, and cell-free aspect. The foregoing tumor challenge result indicates promise for use of antigenic ICVs as effective cancer vaccines. Beyond reducing tumor growth, antigenic ICVs also performed as well as BMDCs in increasing survival rates (e.g., see FIG. 73B). BMDC or antigenic ICV treatment led to complete remission in half of the animals treated.

It will be understood that various modifications may be made without departing from the spirit and scope of this disclosure. Accordingly, other embodiments are within the scope of the following claims.

What is claimed is:

1. A method to produce induced cell vesicles (ICVs) or antigenic ICVs, comprising:
    inducing cell vesicle production from cells by exposing or contacting the cells with a cell blebbing buffer which comprises a sulfhydryl blocking agent;
    wherein the cell blebbing buffer does not contain any small molecule redox reagents or reducing agents.

2. The method of claim 1, wherein the cells are from a subject that has a disorder or disease that is to be treated with ICVs or antigenic ICVs produced therefrom.

3. The method of claim 1, wherein the cells are selected from epithelial cells, fibroblast cells, tumor cells, mast cells, T and B lymphocytes, dendritic cells, and Langerhans cells.

4. The method of claim 1, wherein the induced cell vesicles comprise viruses, viral particles, or viral vectors, by being produced from cells comprising the same.

5. The method of claim 4, wherein the viruses, viral particles, or viral vectors are selected from recombinant retroviruses, adenoviruses, adeno-associated viruses (AAV), alphaviruses, and lentiviruses.

6. The method of claim 5, wherein the viruses, viral particles, or viral vectors are AAV.

7. The method of claim 6, wherein the AAV expresses a heterologous transgene that is used for gene therapy.

8. The method of claim 1, wherein the sulfhydryl blocking agent is selected from the group consisting of and N-ethylmaleimide, mercury chloride, p-chloromercuribenzene sulfonic acid, auric chloride, p-chloromercuribenzoate, chlormerodrin, meralluride sodium, and iodoacetamide.

9. The method of claim 8, wherein the sulfhydryl blocking agent is N-ethylmaleimide (NEM) or maleimide.

10. The method of claim 9, wherein the cell blebbing buffer comprises from 0.5 mM to 100 mM of NEM.

11. A method to produce induced cell vesicles (ICVs) or antigenic ICVs, comprising:
    incubating cells in the absence of light with a photosensitive media comprising a photosensitizer having a concentration of 0.1 ug/mL to 10.0 ug/mL;
    exposing the cells to light generated from a laser to generate ICVs or antigenic ICVs; and
    isolating or collecting the ICVs or the antigenic ICVs.

12. The method of claim 11, wherein the photosensitizer is selected from $AlPc S_{2A}$, $AlPc S_4$, lutrin, 5-aminolevulinic acid (ALA), hypericin, silicon phthalocyanine zinc (II) phthalocyanine (ZnPc), silicon phthalocyanine, mono-L-aspartyl chlorin e6, benzoporphyrin derivative monoacid ring A, chlorin photosensitizer tin etiopurpurin, tetra(m-hydroxyphenyl)chlorin, lutetium texaphyrin, 9-acetoxy-2,7,12,17-tetrakis-($\beta$-methoxyethyl)-porphycene, naphthalocyanines, and Azadipyrromethenes.

13. The method of claim 12, wherein the photosensitizer is $AlPc S_{2A}$.

14. The method of claim 11, wherein the cells are exposed to light having a wavelength selected from 600 nm to 850 nm that is generated by the laser.

15. The method of claim 1, wherein the method further comprises the step of:
    purifying/isolating the ICVs or the antigenic ICVs, wherein the purified/isolated ICVs or antigenic ICVs have average diameters from 10 nm to 10,000 nm.

16. The method of claim 15, wherein the isolated ICVs or isolated antigenic ICVs comprise a cargo selected from biological molecules, therapeutic agents, prodrugs, gene silencing agents, chemotherapeutics, diagnostic agents, components of a gene therapy system and/or components of a gene editing system.

17. The method of claim 16, wherein the isolated ICVs or isolated antigenic ICVs are loaded with the cargo by direct membrane penetration, chemical labeling and conjugation, electrostatic coating, adsorption, absorption, sonification, electroporation, use of pH gradients, or any combination thereof.

18. The method of claim 1, wherein the cells comprise or have been modified to comprise one or more functional moieties on the cell surface.

19. The method of claim 18, wherein the cells have been bioorthogonally-conjugated to comprise one or more functional moieties.

20. The method of claim 19, wherein the one or more functional moieties have been added to the surface of the cells by bioorthogonally-engineering, comprising:

(1) treating sialic acid residues on the surface of the cells with an oxidizing agent to form aldehyde groups; then either step (2)(a) and (b), or step (3)(a) and (3)(b):

(2)(a) ligating, linking or conjugating aminooxy-functionalized molecules to the surface of the cells by forming oxime bonds with the aldehyde groups; and (2)(b) inducing production of bioorthogonally-conjugated ICVs or bioorthogonally-conjugated antigenic ICVs by exposing or contacting the cells with the cell blebbing buffer which comprises a sulfhydryl blocking agent; or (3)(a) inducing production of ICVs or antigenic ICVs from the cells by exposing or contacting the cells with the cell blebbing buffer which comprises a sulfhydryl blocking agent; and (3)(b) producing bioorthogonally-conjugated ICVs or bioorthogonally-conjugated antigenic ICVs by ligating, linking or conjugating aminooxy-functionalized molecules to the surface of the ICVs by forming oxime bonds with the aldehyde groups.

21. Bioorthogonally-conjugated ICVs produced by the method of claim 20.

22. A method of stimulating an immune response to a cancer in a subject in need thereof, comprising:

(a) obtaining antigen presenting cells;

(b) pulsing the antigen presenting cells with an antigen associated with cancer cells;

(c) inducing cell membrane blebbing by contacting the pulsed antigen presenting cells with a cell blebbing buffer which comprises a sulfhydryl blocking agent, wherein the cell blebbing buffer does not contain any small molecule redox reagents or reducing agents;

(d) collecting antigenic ICVs induced by cell membrane blebbing; and (e) administering said antigenic ICVs to the subject in need of immunotherapy.

23. The method of claim 22, wherein the antigenic ICVs are administered by intravenous administration, intertumoral administration, intraperitoneal administration, intramuscular administration, intracoronary administration, intraarterial administration, subcutaneous administration, transdermal delivery, intratracheal administration, subcutaneous administration, intraarticular administration, intraventricular administration, inhalation, or intracerebral administration.

24. The method of claim 22, wherein the antigenic ICVs are administered concurrently or sequentially with one or more anticancer agents or chemotherapeutics.

25. A cell-free cell therapy comprising a pharmaceutical composition comprising the bioorthogonally-conjugated ICVs of claim 21 for use in treating a subject having a disease or disorder.

26. A vaccine comprising a pharmaceutical composition comprising the bioorthogonally-conjugated ICVs of claim 21 for prevention of an infection in a subject by an infectious agent.

* * * * *